United States Patent
Khanna

(10) Patent No.: US 9,018,173 B2
(45) Date of Patent: Apr. 28, 2015

(54) MATERIALS AND METHODS FOR SUPPRESSING INFLAMMATORY AND NEUROPATHIC PAIN

(75) Inventor: Rajesh Khanna, Indianapolis, IN (US)

(73) Assignee: Indiana University Research and Technology Corp., Indianapolis, IN (US)

( * ) Notice: Subject to any disclaimer, the term of this patent is extended or adjusted under 35 U.S.C. 154(b) by 0 days.

(21) Appl. No.: 13/703,181

(22) PCT Filed: Jun. 10, 2011

(86) PCT No.: PCT/US2011/040100
§ 371 (c)(1),
(2), (4) Date: Apr. 30, 2013

(87) PCT Pub. No.: WO2012/009075
PCT Pub. Date: Jan. 19, 2012

(65) Prior Publication Data
US 2013/0210698 A1 Aug. 15, 2013

Related U.S. Application Data

(60) Provisional application No. 61/353,373, filed on Jun. 10, 2010, provisional application No. 61/454,436, filed on Mar. 18, 2011.

(51) Int. Cl.
| | |
|---|---|
| A61K 38/16 | (2006.01) |
| A61K 38/10 | (2006.01) |
| A61K 38/00 | (2006.01) |
| A61K 47/00 | (2006.01) |
| A61P 25/02 | (2006.01) |
| A61P 23/00 | (2006.01) |
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |
| C07K 14/005 | (2006.01) |
| C07K 14/47 | (2006.01) |

(52) U.S. Cl.
CPC ........... *C07K 14/005* (2013.01); *C07K 14/4702* (2013.01); *A61K 38/00* (2013.01); *C07K 2319/00* (2013.01)

(58) Field of Classification Search
None
See application file for complete search history.

(56) References Cited

U.S. PATENT DOCUMENTS

2009/0068148 A1* 3/2009 Garry et al. .................. 424/93.2
2009/0176713 A1* 7/2009 Tymianski et al. ............. 514/15

OTHER PUBLICATIONS

Brittain et al., "An Atypical Rolse for Collapsin Response Mediator Protein 2 (CRMP-2) in Neurotransmitter Release via Interaction with Presynaptic Voltage-gated Calcium Channels," J. Biol. Chem. 284:313175-313190 (2009).*
NCBI Database, GeneBank Accession No. NM_009955, 7 pages (2007).*
Brittain et al., "An Atypical Role for Collapsin Response Mediator Protein 2 (CRMP-2) in Neurotransmitter Release via Interaction with Presynaptic Voltage-gated Calcium Channels," J. Biol. Chem. 284:31375-31390 (2009).*
NCBI Database, GeneBank Accession No. NM_009955, 7 pages (2007).*
Young, L.W., International Search Report for PCT/US11/40100, Nov. 30, 2011, pp. 1-3, ISA/US.
Young, L.W., Written Opinion of the International Searching Authority for PCT/US11/40100, Nov. 30, 2011, pp. 1-5, ISA/US.
European Search Opinion for EP App. No. 11807221.4, Nov. 12, 2013, pp. 1-2.
Wang et. al.: "Emerging roles of collapsin response mediator proteins (CRMPs) as regulators of voltage-gated calcium channels and synaptic transmission", Commun Integr Biol., May 1, 2010, pp. 172-175.
Schmidt E.F. et. al.: "The CRMP family of proteins and their role in Sema3A signaling", Advances in Experimental Medicine and Biology, Jan. 1, 2007, pp. 1-14, vol. 600.
Brittain Joel M et al: "Suppression of inflammatory and neuropathic pain by uncoupling CRMP-2 from the presynaptic Ca2+ channel complex", Nature Medicine, Jul. 2011, pp. 1-19, vol. 17, No. 7.
Young, C., Supplementary European Search Report for EP App. No. 11807221.4, Oct. 21, 2013, p. 1.

* cited by examiner

*Primary Examiner* — James H Alstrum Acevedo
*Assistant Examiner* — Thea D'Ambrosio
(74) *Attorney, Agent, or Firm* — Faegre Baker Daniels LLP

(57) ABSTRACT

N-type voltage-gated calcium channels (CaV2.2) are critical mediators of neurotransmitter release and are thought to be involved with transmission of nociception. The use of conventional CaV2.2 blockers in pain therapeutics is limited by side effects. Reported herein is a means to suppress both inflammatory and neuropathic pain without directly blocking CaV2.2, but rather by inhibiting the binding of the axonal collapsin response mediator protein 2 (CRMP-2), a protein known to enhance CaV2.2 function. A 15 amino acid peptide of CRMP-2 fused to the protein transduction domain of the HIV tat protein (TAT CBD3) reduced meningeal blood flow induced by activation of the trigeminovascular system, prevented inflammation-induced tactile hypernociception induced by intraplantar formalin and nocifensive behavior following corneal capsaicin application, and reversed neuropathic hypernociception produced by the antiretroviral drug 2',3'-dideoxycytidine. Preventing CRMP-2—mediated enhancement of CaV2.2 function suppressed inflammatory and neuropathic nociception, providing a method for treating pain and inflammation.

18 Claims, 82 Drawing Sheets

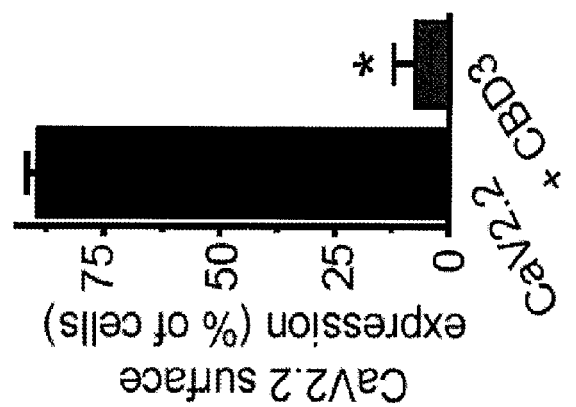

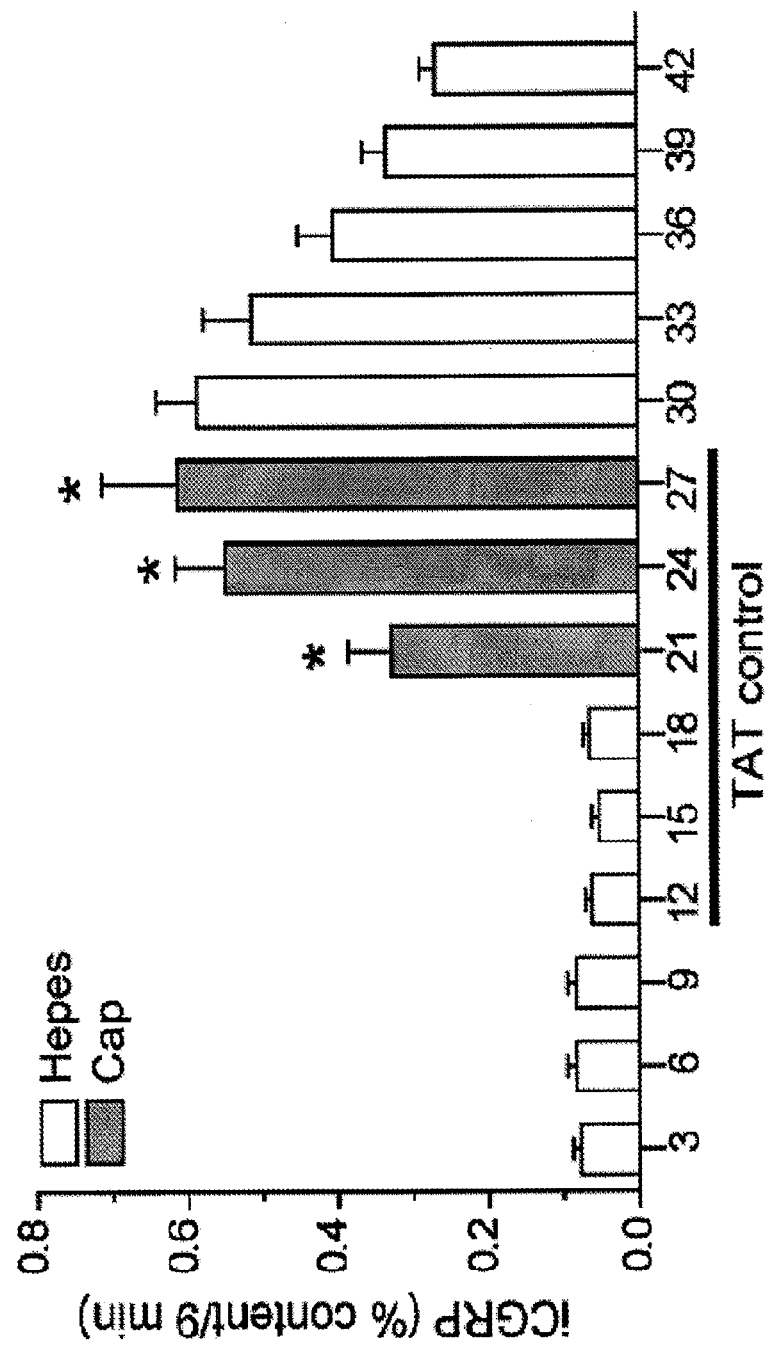

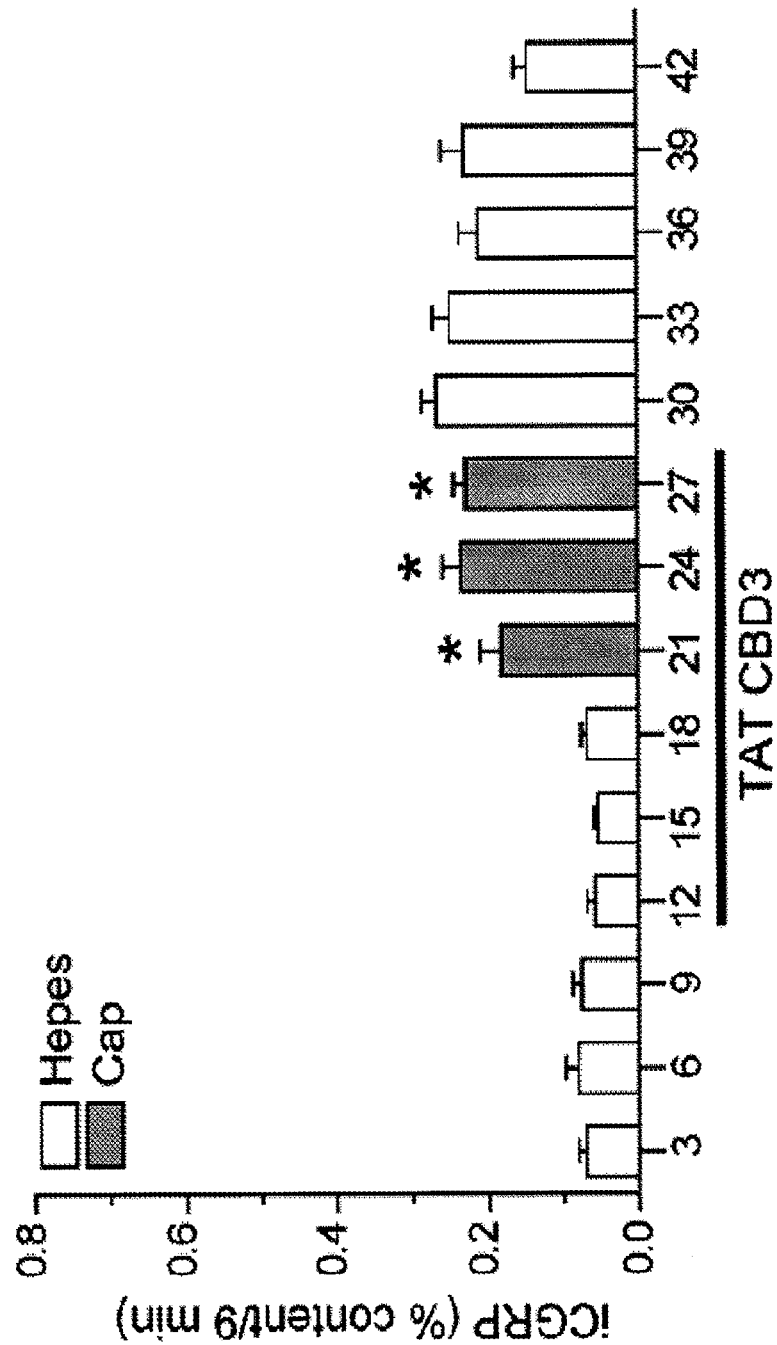

IP: Streptavidin

SEQUENCE LISTING

```
<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: CBD3

<400> SEQUENCE: 1

Ala Arg Ser Arg Leu Ala Glu Leu Arg Gly Val Pro Arg Gly Leu
1               5                   10                  15

<210> SEQ ID NO 2
<211> LENGTH: 26
<212> TYPE: PRT
<213> ORGANISM: Artificial Sequence
<220> FEATURE:
<223> OTHER INFORMATION: control

<400> SEQUENCE: 2

Tyr Gly Arg Lys Lys Arg Arg Gln Arg Arg Trp Glu Ala Lys Glu
1               5                   10                  15

Met Leu Tyr Phe Glu Ala Leu Val Ile Glu
            20                  25
```

```
<210> SEQ ID NO 3
<211> LENGTH: 15
<212> TYPE: PRT
<213> ORGANISM: Artificial Sequence
<220> FEATURE:
<223> OTHER INFORMATION: exemplary polypeptide 2

<400> SEQUENCE: 3

Ala Arg Ser Arg Ala Ala Glu Leu Arg Gly Val Pro Arg Gly Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: exemplary polypeptide 3

<400> SEQUENCE: 4

Ala Arg Pro Arg Leu Ala Glu Leu Arg Gly Val Pro Arg Gly Leu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: exemplary polypeptide 4

<400> SEQUENCE: 5

Ala Arg Pro Arg Arg Ala Glu Leu Arg Gly Val Pro Arg Gly Leu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: exemplary polypeptide 5

<400> SEQUENCE: 6

Ala Arg Ser Arg Leu Ala Glu Leu Arg Arg Val Pro Arg Gly Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: exemplary polypeptide 6

<400> SEQUENCE: 7

Ala Arg Ser Arg Leu Ala Glu Leu Arg Gly Val Pro Arg Phe Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: exemplary polypeptide 7

<400> SEQUENCE: 8

Ala Arg Ser Arg Leu Lys Glu Leu Arg Gly Val Pro Arg Gly Leu
1               5                   10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: exemplary polypeptide 8

<400> SEQUENCE: 9

Ala Arg Ser Arg Leu Ala Asp Leu Arg Gly Val Pro Arg Gly Leu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: exemplary polypeptide 9

<400> SEQUENCE: 10

Ala Arg Ser Trp Leu Ala Glu Leu Arg Gly Val Pro Arg Gly Leu
1               5                   10                  15

<210> SEQ ID NO 11
<211> LENGTH: 26
<212> TYPE: PRT
<213> ORGANISM: Artificial Sequence
<220> FEATURE:
<223> OTHER INFORMATION: TAT plus CBD3

<400> SEQUENCE: 11

Tyr Gly Arg Lys Lys Arg Arg Gln Arg Arg Ala Arg Ser Arg Leu
1               5                   10                  15

Ala Glu Leu Arg Gly Val Pro Arg Gly Leu
            20                  25

<210> SEQ ID NO 12
<211> LENGTH: 12
<212> TYPE: PRT
<213> ORGANISM: Human immunodeficiency virus type 1

<400> SEQUENCE: 12

Gly Arg Lys Lys Arg Arg Gln Arg Arg Arg Pro Gln
1               5                   10

<210> SEQ ID NO 13
<211> LENGTH: 11
<212> TYPE: PRT
<213> ORGANISM: Human immunodeficiency virus type 1

<400> SEQUENCE: 13

Tyr Gly Arg Lys Lys Arg Arg Gln Arg Arg
1               5                   10

<210> SEQ ID NO 14
<211> LENGTH: 16
<212> TYPE: PRT
<213> ORGANISM: unknown
<220> FEATURE:
<223> OTHER INFORMATION: penetratin from helix 3 of the antennapedia
      complex

<400> SEQUENCE: 14

Arg Gln Ile Lys Ile Trp Phe Gln Asn Arg Arg Met Lys Trp Lys Lys
1               5                   10                  15
```

MATERIALS AND METHODS FOR SUPPRESSING INFLAMMATORY AND NEUROPATHIC PAIN

CROSS-REFERENCES TO RELATED APPLICATIONS

This application is a National Stage filing of International Application Serial No. PCT/US2011/040100, filed Jun. 10, 2011, which claims the benefit of U.S. Provisional No. 61/353,373 filed Jun. 10, 2010 and U.S. Provisional No. 61/454,436 filed Mar. 18, 2011, the disclosures of which are expressly incorporated herein by reference.

FIELD OF THE INVENTION

Aspects of the invention relate to suppressing pain by uncoupling collapsin response mediator protein 2 (CRMP-2) from the presynaptic calcium channel complex using, for example, a peptide.

BACKGROUND

Inflammatory diseases and nerve injuries can lead to incapacitating pain, which can become chronic and refractory to currently available treatment options. Opioid treatment offers relief but is limited due to considerable side effects. For chronic intractable clinical pain, intrathecal delivery of ziconotide, a synthetic ω-conotoxin that blocks neuronal calcium channels, has been approved, thus identifying the N-type $Ca^{2+}$ channel (CaV2.2) as a critical target for treatment of chronic pain. Saegusa, H., et al., Suppression of inflammatory and neuropathic pain symptoms in mice lacking the N-type Ca2+ channel. *EMBO J.* 20, 2349-2356 (2001). Due in part to an increase in the number of people diagnosed with chronic pain and the lack of effective treatments for many of them. There is a great need for new materials and methods for controlling pain. Some aspects of the present invention seek to address this need.

SUMMARY

Some embodiment of the invention include compounds that uncouple the interaction between CRMP-2 and CaV2.2, these compounds may comprise the formula X-Z, wherein X is a polypeptide having at least 80 percent identify to at least one polypeptide selected from the groups consisting of: SEQ ID NO.: 12 and SEQ ID NO.: 13 and Z is at least one polypeptide having at least 80 percent identity to at least one polypeptide selected from the group consisting: of SEQ. ID NO.: 1, SEQ. ID NO.: 3, SEQ. ID NO., SEQ. ID NO.: 5, SEQ. ID NO.: 6, SEQ. ID NO.: 7, SEQ. ID NO.: 8, SEQ. ID NO.: 9, and SEQ. ID NO.: 10, wherein X and Z are fused to one another. In some of the embodiments the compound are formed by fusing X and Z to one another via a peptide bond.

In some embodiment, X is a polypeptide that has at least 90 percent identity to at least one polypeptide selected from the group consisting of SEQ ID NO.: 11 and SEQ ID NO.: 12. In some embodiments, Z is a polypeptide that has at least 90 percent identity to at least one polypeptide selected from the group consisting of SEQ. ID NO.: 1, SEQ. ID NO.: 3, SEQ. ID NO. 4, SEQ. ID NO.: 5, SEQ. ID NO.: 6, SEQ. ID NO.: 7, SEQ. ID NO.: 8, SEQ. ID NO.: 9, and SEQ. ID NO.: 10. In some embodiments, X in the compound is at least one polypeptide that has at least 95 percent identity to at least one polypeptide selected from the group consisting of SEQ ID NO.: 11 and SEQ ID NO.: 12. In some embodiments, X is a polypeptide having at least 90 percent homology to at least one polypeptide selected from the groups consisting of: SEQ ID NO.: 12 and SEQ ID NO.: 13, and in some embodiments, Z is a polypeptide having at least 90 percent homology to at least one polypeptide selected from the group consisting: of SEQ. ID NO.: 1, SEQ. ID NO.: 3, SEQ. ID NO. 4: SEQ. ID NO.: 5, SEQ. ID NO.: 6, SEQ. ID NO.: 7, SEQ. ID NO.: 8, SEQ. ID NO.: 9, and SEQ. ID NO.: 10, wherein X and Z are fused to one another. While in still other embodiments, X is a polypeptide having at least 95 percent homology to at least one polypeptide selected from the groups consisting of: SEQ ID NO.: 12 and SEQ ID NO.: 13, and in some embodiments, Z is a polypeptide having at least 95 percent homology to at least one polypeptide selected from the group consisting: of SEQ. ID NO.: 1, SEQ. ID NO.: 3, SEQ. ID NO. 4, SEQ. ID NO.: 5, SEQ. ID NO.: 6, SEQ. ID NO.: 7, SEQ. ID NO.: 8, SEQ. ID NO.: 9, and SEQ. ID NO.: 10, wherein X and Z are fused to one another.

In some embodiment, X is at least one polypeptide selected from the group consisting of SEQ ID NO.: 12 and SEQ ID NO.: 13. And, in some embodiments, Z is a polypeptide selected from the group consisting: of SEQ. ID NO.: 1, SEQ. ID NO.: 3, SEQ. ID NO. 4, SEQ. ID NO.: 5, SEQ. ID NO.: 6, SEQ. ID NO.: 7, SEQ. ID NO.: 8, SEQ. ID NO.: 9, and SEQ. ID NO.: 10. In still other embodiments, the inventive compound is SEQ ID NO. 11.

Some embodiments provide methods of treating a patient, comprising the steps: providing at least one compound, for example, a polypeptide that uncouples the interaction between CRMP-2 and CaV2.2. Representative compound include, but are not limited to, compounds such as the polypeptide of SEQ ID No.: 11. In some embodiments, the compound is formulated for administering to a patient. Some embodiments further includes the step of: administering at least one therapeutically effective dose of said compound to a patient. In some embodiments, a single therapeutic dose is between about 1 mg to about 100 mg of said compound per about 1 kilogram of the patient's body weight. And in still other embodiments the dose is between about 1 mg to about 20 mg of said compound per about 1 kilogram of the patient's body weight. While in still other embodiments, the dose may lie outside of these ranges and can be readily determined for individual patients. In some embodiments, the compound is used to treat a mammal such as a mouse, rat or human being.

Some embodiments include kits for treating patients. These kits comprise at least one compound, for example, a polypeptide that uncouples the interaction between CRMP-2 and CaV2.2. Representative compound include, but are not limited to, compounds such as the polypeptide of SEQ ID No.: 11. In some embodiments, the kits include at least one therapeutically effective dose of the compound according to claim 1 or a pharmaceutically acceptable salt thereof. In some embodiments, the compound in the kit is formulated for injection. In some embodiments the kit includes at least one additional material that helps to preserve the activity of said compound. Some aspects of the invention include compounds for treating pain and inflammation, comprising a compound of the formula X-Z, wherein X is a polypeptide having at least 80 percent identify to the polypeptide SEQ ID NO.: 13 and Z is at least one polypeptide having at least 90 percent identity to at least one polypeptide selected from the group consisting of SEQ. ID NO.: 1, SEQ. ID NO.: 3, SEQ. ID NO.: 4, SEQ. ID NO.: 5, SEQ. ID NO.: 6, SEQ. ID NO.: 7, SEQ. ID NO.: 8, SEQ. ID NO.: 9, and SEQ. ID NO.: 10, wherein X and Z are fused to one another.

Some aspects of the invention include compounds that uncouple the interaction between CRMP-2 and CaV2.2. In some embodiments, these compounds comprise at least one peptide, selected from the group of peptides consisting of group A wherein group A includes: SEQ. ID NO.: 1, SEQ. ID NO.: 3, SEQ. ID NO.: 4, SEQ. ID NO.: 5, SEQ. ID NO.: 6, SEQ. ID NO.: 7, SEQ. ID NO.: 8, SEQ. ID NO.: 9, SEQ. ID NO.: 10, and SEQ ID NO.: 11. In some embodiments, the compounds include peptides that have at least 90 percent or 95 percent identity to at least one peptide selected from group A. In some embodiments, the compounds may include peptides that hybridize under stringent conditions to at least one of the peptides selected from the peptides in group A. In some embodiments, the peptides used to practice the invention may include non-standard amino acids.

Some embodiments of the invention include methods of treating either a human or an animal patient by first identifying a patient in need of such treat, and then administering to the patient at least one therapeutically effective dose of at least one compound that at least partially uncouples the interaction between CRMP-2 and CaV2.2. In some of these methods, the compound used to treat the patient is selected from the group of compounds selected from the group of peptides consisting of group A wherein group A includes: SEQ. ID NO.: 1, SEQ. ID NO.: 3, SEQ. ID NO.: 4, SEQ. ID NO.: 5, SEQ. ID NO.: 6, SEQ. ID NO.: 7, SEQ. ID NO.: 8, SEQ. ID NO.: 9, SEQ. ID NO.: 10, and SEQ ID NO.: 11. In some embodiments, the compounds include peptides that have at least 90 percent or 95 percent identity to at least one peptide selected from group A. In some embodiments, the compounds may include peptides that hybridize under stringent conditions to at least one of the peptides selected from the peptides in group A. In some embodiments, the peptides used to practice the invention may include non-standard amino acids.

In some embodiments, the patient being treated has been diagnosed with or is at risk for developing pain related to pathological inflammation. In some patients, the pain may be caused by conditions such a diabetic neuropathy or similar conditions. In some patients the pain may be the result of treatment with other compounds to treat conditions such as cancer, HIV-AIDS and the like. In still other embodiments the inhibitor polypeptide is fused to penetratin from helix 3 of the antennapedia complex (RQIKIWFQNRRMKWKK "SEQ. ID NO.: 14"; Thoren, P. E., Persson, D., Isakson, P., Goksor, M., Onfelt, A. & Norden, B. (2003) Uptake of analogs of penetratin, Tat (48-60) and oligoarginine in live cells. Bioch. Biophys. Res. Comm. 307, 100-107).

BRIEF DESCRIPTION OF THE SEQUENCES

SEQ. ID NO.: 1 provides polypeptide CBD3.

SEQ. ID NO.: 2 provides a polypeptide control (TAT-Scramble) having the modified TAT sequence of SEQ ID NO.: 13 coupled to a random, non-specific polypeptide sequence.

SEQ. ID NO.: 3 provides an exemplary polypeptide sequence according to the instant disclosure.

SEQ. ID NO.: 4 provides another exemplary polypeptide sequence according to the instant disclosure.

SEQ. ID NO.: 5 provides yet another exemplary polypeptide sequence according to the instant disclosure.

SEQ. ID NO.: 6 provides even yet another exemplary polypeptide sequence according to the instant disclosure.

SEQ. ID NO.: 7 provides another exemplary polypeptide sequence according to the instant disclosure.

SEQ. ID NO.: 8 provides another exemplary polypeptide sequence according to the instant disclosure.

SEQ. ID NO.: 9 provides yet another exemplary polypeptide sequence according to the instant disclosure.

SEQ. ID NO.: 10 provides even yet another exemplary polypeptide sequence according to the instant disclosure.

SEQ. ID NO.: 11 provides a polypeptide having the modified TAT sequence of SEQ ID NO.: 13 coupled to the polypeptide CBD3 sequence of SEQ ID NO.: 1.

SEQ. ID NO.: 12 provides the polypeptide sequence of TAT cell membrane transduction domain of the human immunodeficiency virus-type 1.

SEQ. ID NO.: 13 provides a modified TAT sequence for coupling to an exemplary polypeptide sequence according to the instant disclosure.

SEQ. ID NO.: 14 provides the sequence for penetratin from helix 3 of the antennapedia complex.

BRIEF DESCRIPTION OF THE FIGURES

FIG. 1G. Bar graph showing CaV2.2 expression per cell measured with either CaV2.2 or CBD3.

FIG. 3A. Time course of iCGRP released with Capsaicin in the presence of TAT control peptide.

FIG. 3B. Time course of iCGRP released after stimulation with TAT CBD3.

FIG. 19.B. Calcium release versus time measured in untreated cells and cells treated with CBD3.

FIG. 19.C. Bar graph illustrating peak calcium release measured under various conditions.

FIG. 19.D. Bar graph of the normalized maximum change in fluorescence measured after exposure to TAT Scramble or TAT-CBD3.

FIG. 20.B. Graph showing relationship between current and voltage in DRG neurons treated with TAT-Scramble or TAT-CBD3.

FIG. 20.C. Bar graph of current density measured at +5 mV mV in DRG neurons treated with either TAT-Scramble or (5) or TAT-CBD3 (6).

FIG. 20.D. Graph showing normalized channel count as a function of membrane potential.

FIG. 20.E. Deconvolved image of DRG neurons treated with FITC-TAT-CBD3.

FIG. 21.B. Bar graph of percent inhibition of eEPSCs exposed to: TAT-Scramble (6), TAT-CBD3 (11) or ω-CTX (5).

FIG. 21.C. Bar graph of paired pulse ratios measured from neurons prior to and after treatment with TAT-Scramble or TAT-CBD3.

FIG. 22.B. Bar graph illustrating iCGRP release measured in DRG neurons.

FIG. 22.C. Bar graph of iCGRP release measured in DRG neurons measured throughout exposure to high levels of $K^+$.

FIG. 22.D. Bar graph of iCGRP release measured in DRG neurons exposed to high levels of $K^{30}$.

FIG. 22.E. Bar graph showing iCGRP release from spinal cord slices measured under different conditions.

FIG. 22.F. Bar graph of total iCGRP release measured after exposure to either TAT-Scramble or TAT-CBD3.

FIG. 22.G. Bar graph of optical density measured at 490 nm of cells in control group or cells exposed to either TAT-Scramble or TAT-CBD3.

FIG. 23.B. Bar graph of cumulative peak current density measured after capsaicin challenge and various treatments.

FIG. 23.C. Graph of normalized response versus concentration of capsaicin measured after no treatment or treatment with either TAT-Scramble or TAT-CBD3 for 10 minutes.

FIG. 23.D. Graph of normalized response versus concentration of capsaicin measured after no treatment or treatment with either TAT-Scramble or TAT-CBD3 for overnight.

FIG. 23.E. Bar graph showing time required to reach half-peak current in any capsaicin challenges measured upon exposure to no peptides or to TAT-Scramble or TAT-CBD3 for 10 mins.

FIG. 23.F. Bar graph showing time required to reach half-peak current in any capsaicin challenges measured upon exposure to no peptides or to TAT-Scramble or TAT-CBD3 overnight.

FIG. 24.B. FITC analysis of rat brains, CSF or plasma.

FIG. 24.C. Bar graph fold of normalized fluorescence in observed in animal tissue FIG. 24.D. Photograph of rat before intraperitoneal injection of TAT-CBD3.

FIG. 24.E. Photograph of rat after injection with TAT-CBD3.

FIG. 24.F. Photograph of rat after injection with TAT-CBD3.

FIG. 24.G. Photograph of rat 5 min after injection with TAT-CBD3.

FIG. 24.H. Bar graph percent of animals with kinking tails measured after no injection or injection with either TAT-Scramble or TAT-CBD3.

DESCRIPTION

Figure 1A:
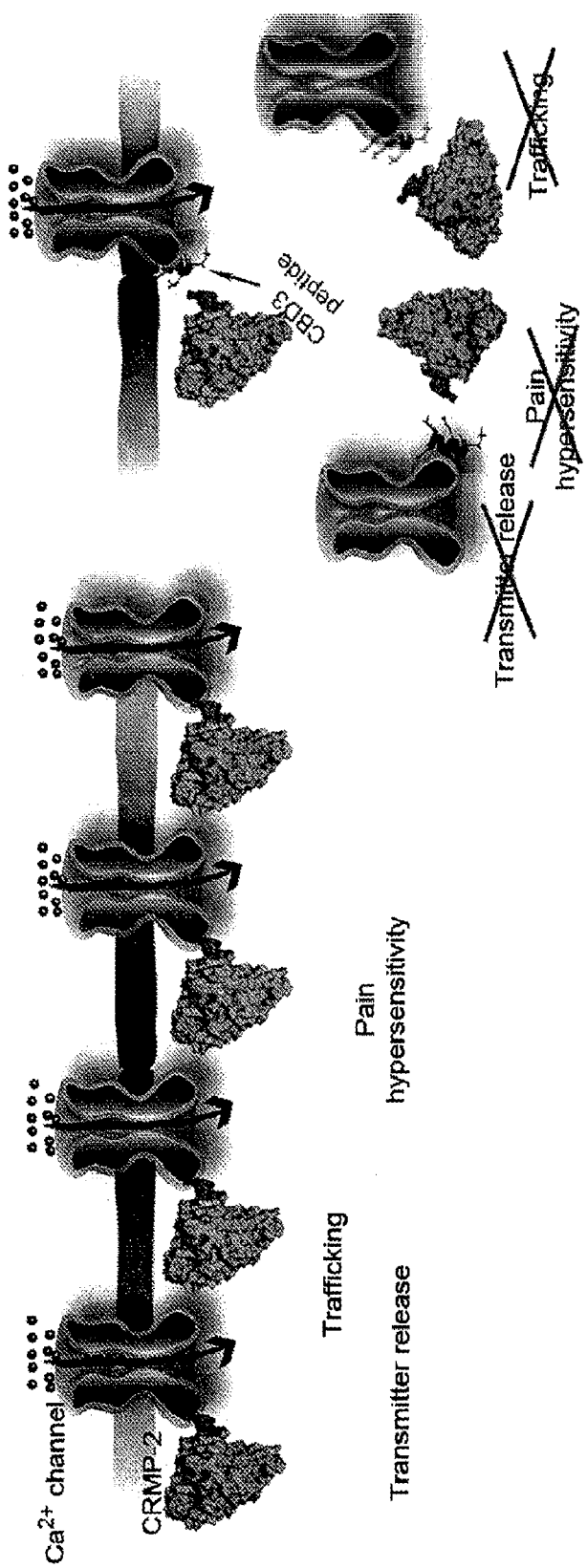
FIG. 1A. Cartoon illustrating interaction between $Ca^{2+}$ channel and CRMP-2
Figure 1B:
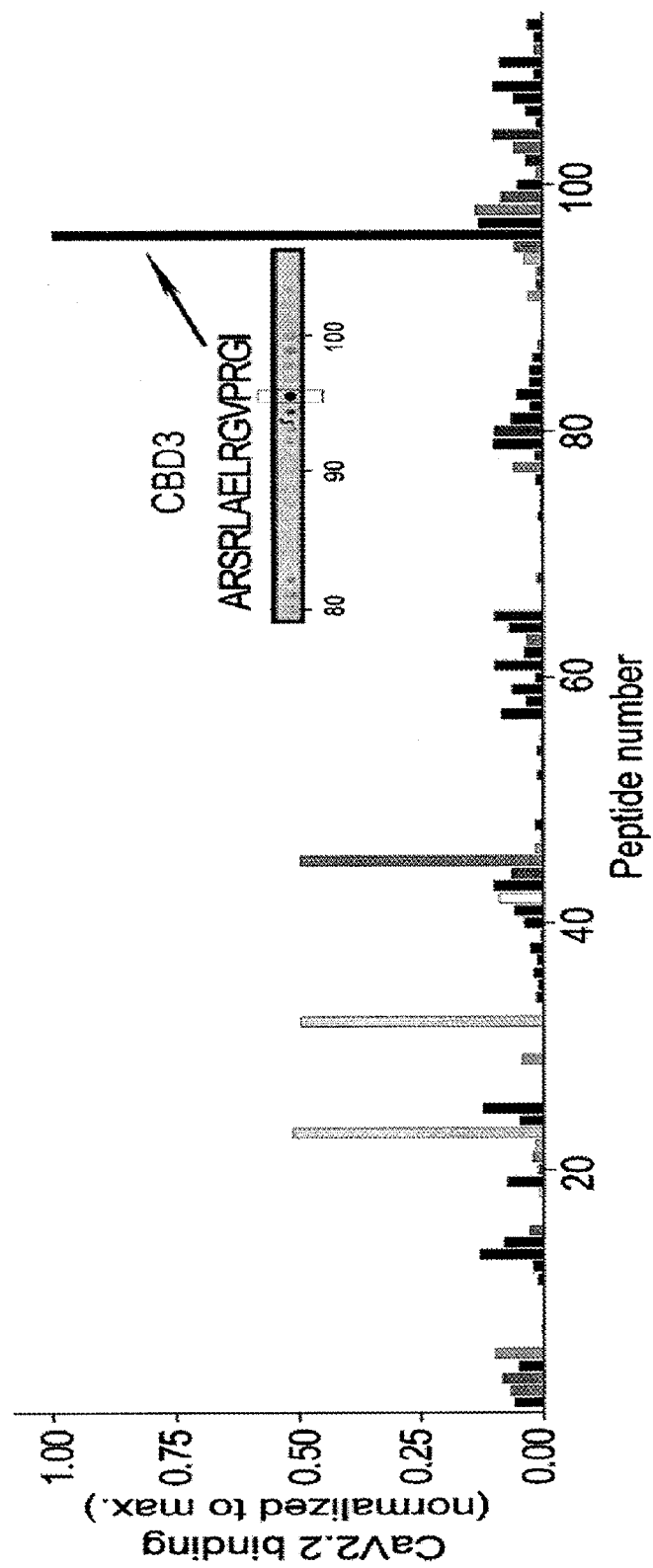
FIG. 1B. Graph of normalized CaV2.2 binding measured in presence of various CRMP-2peptides.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

N-type calcium channels are multiprotein complexes comprised of a pore-forming α-subunits and auxiliary α2/δ, β, and γ subunits. CaV2.2 channels are localized to primary afferent terminals in laminae 1 and 2 of the dorsal horn. Activation of CaV2.2 results in the influx of calcium and release of neurotransmitters such as glutamate, substance P, and calcitonin gene-related peptide (CGRP). CaV2.2 channels are also critical for nociceptive transduction as block of these channels relieves hyperalgesia, mice lacking CaV2.2 show an increased threshold for nociception, and expression of CaV2.2 is upregulated following a chronic constrictive nerve injury. The importance of CaV2.2 in pain is further highlighted by the demonstration of a naturally occurring alternative splice form of CaV2.2 (i.e., exon 37a) in small-diameter nociceptive neurons which are critical for basal thermal nociception, and thermal and mechanical hyperalgesia. In sum, by virtue of their ability to control the regulated release of neurotransmitters, the N-type $Ca^{2+}$ channels are a prime target for the development of novel analgesics. Zamponi, G. W., et al., Scaffold-based design and synthesis of potent N-type calcium channel blockers. *Bioorg. Med. Chem. Lett.* 19, 6467-6472 (2009).

CRMPs are involved in a variety of neurological dysfunctions including, Alzheimer's disease progression, paraneoplastic neurological syndromes, cerebral ischemia and stroke, neuroinflammation, and Down syndrome brain. An alteration in $Ca^{2+}$ homeostasis appears to key in the mechanisms of the neuronal/axonal injury underlying these diseases. For example, $Ca^{2+}$-dependent CRMP-2 proteolysis has been observed in traumatic brain injury and cerebral ischemia and may be a limiting factor for post-injury axonal regeneration. Data shows that CRMP-2 overexpression increases CGRP release in a manner dependent upon $Ca^{2+}$ influx via CaV2.2. Thus, proteins interacting with $Ca^{2+}$ channels, such as CRMP-2, represent a novel target for manipulation of CGRP release for pain regulation and future therapeutics in neurological diseases. The TAT CBD3 peptide, by uncoupling the interaction between CaV2.2 and CRMP-2, may prove useful in the above diseases.

For chronic and neuropathic pain not treatable with conventional analgesics or opiates, exploitation of calcium channels as a therapeutic target has shown some promise. However, channel blockers like ziconotide, are limited by their method of delivery, narrow therapeutic window and adverse effects such as hypotension and memory loss, necessitating the development of better inhibitors. Alternative strategies that target proteins interacting with calcium channels represent a novel route of drug discovery for treatment of clinical pain. For example, the drug gabapentin targets the α2δ1 subunit of voltage-gated calcium channels by impairing channel trafficking, reducing neurotransmitter release and resultant spinal sensitization. Recently CRMP-2 was identified as a novel modulator of CaV2.2. Brittain, J. M., et al., An atypical role for collapsin response mediator protein 2 (CRMP-2) in neurotransmitter release via interaction with presynaptic voltage-gated Ca2+ channels. *J. Biol. Chem.* 284, 31375-31390 (2009).CRMP-2 is a cytosolic phosphoprotein originally identified as a mediator of semaphorin3A growth cone collapse. CRMP-2 has been shown to regulate axon number and length and neuronal polarity. CRMP-2 interacts with CaV2.2 and overexpression of CRMP-2 leads to increased surface expression of CaV2.2 and enhanced $Ca^{2+}$ currents. CRMP-2 overexpression also increases stimulated release of CGRP from dorsal root ganglia (DRG). Furthermore, knockdown of CRMP-2 dramatically reduces $Ca^{2+}$ currents and transmitter release. One plausible inference of these findings is that the biochemical interaction between CRMP-2 and CaV2.2 is required for proper channel trafficking and function. As reported herein, the hypothesis that uncoupling the CRMP-2-CaV2.2 interaction would lead to a physiologically relevant decrease in $Ca^{2+}$ current and neurotransmitter release and may suppress chronic inflammatory and neuropathic nociceptive hypersensitivity was explored.

These findings show that the Transactivator of Transcription TAT CBD3 peptide, but not TAT control, is efficacious in a number of animal models of pain. The pharmacologic block of CaV2.2 induced by TAT CBD3 peptide produced analgesic effects in rodents subjected to formalin-induced tactile hypernociceptive behavior, nocifensive evoked by ocular administration of capsaicin, and neurogenic inflammation of the meninges. TAT CBD3 peptide was similarly effective in reversing the chronic tactile hypernociceptive behavior observed in antiretroviral toxic neuropathy. The analgesic activity of TAT CBD3 across a number of pain models suggests that N-type voltage calcium channels on the presynaptic terminals of afferent sensory neurons are a common link between inflammatory and neuropathic pain behaviors.

The CBD3 peptide was designed for the purpose of blocking the interaction between CRMP-2 and the N-type calcium channel. As previously shown, CRMP2 is involved in trafficking of the channel to the membrane thereby increasing calcium current density. One hypothesis based on these observations is that blocking this interaction would have a negative effect on surface expression of CaV2.2 and current density. As shown here, the effects of CBD3 on the functional interaction between these two proteins ultimately resulted in a marked reduction in neurotransmitter release. Since N-type calcium channels are also present in the presynaptic terminals of primary afferent sensory neurons, notably A-δ and C fibers, CBD3's actions were not limited to the central nervous system.

CaV2.2-containing neurons within the peripheral nervous system are responsible for relaying nociceptive signals primarily through their connections within the spinothalamic tract, in laminae I and II. Calcium influx through these channels is the primary mechanism underlying substance P and CGRP release from these fibers. Pharmacologic block of CaV2.2 not only reduces neurotransmitter release but may also decrease the excitability of the post-synaptic neurons within lamina I of the spinal cord. It was shown previously that CRMP2 modulates CGRP release from primary neurons derived from the dorsal root ganglia. By uncoupling the interaction between CaV2.2 and CRMP2 within the primary afferent sensory neurons, transduction of pain signals may be attenuated. A primary obstacle in the pursuit of this hypothesis was the inability of the CBD3 peptide to cross the plasma membrane. Protein transduction domains such as the human immunodeficiency virus-1 (HIV-1) TAT, can render peptides membrane penetrant. Conjugation of the peptide to HIV-1 TAT led to efficient transduction of CBD3 into cells in vitro, ex vivo and in vivo. Application of TAT CBD3 effectively reduced capsaicin and formalin-induced overt nociception, demonstrating its ability to attenuate acute pain signals.

Expression of CaV2.2 is upregulated in several animal models of chronic and neuropathic pain. Calcium entry through these channels affects the repetitive firing patterns of the A-δ and C fibers. It has been proposed that CaV2.2 is responsible for instigating the increased excitability and neurotransmitter release associated with chronic and neuropathic pain conditions and CaV2.2 has become a prime therapeutic target in the treatment of chronic pain. A synthetic version of the peptide-CaV2.2-selective blocker ω-conotoxin, Prialt®, has recently completed clinical trials. Complete block of Cav2.2, however, is not without side effects. Though slightly dependent upon method of administration, treatment with Prialt® in humans is accompanied by psychiatric symptoms, cognitive impairment, and postural hypotension likely attributable to the importance of CaV2.2 in the central and sympathetic nervous systems. The low therapeutic index of the current N-type blockers propels the search for alternative methods of treatment. TAT CBD3 was effective in abolishing the nociceptive hypersensitivity to tactile stimulation in an animal model of chronic/neuropathic pain. TAT CBD3 may allow the suppression of pain hypersensitivity without directly blocking CaV2.2, but rather by inhibiting the binding of a regulator of CaV2.2 function, CRMP-2.

The discovery of novel small-molecule CaV2.2 inhibitors for use as analgesics may lead to improved therapeutic pharmacology. Previous reports identified CRMP-2 as a novel modulator of CaV2.2. CRMP-2 is a cytosolic phosphoprotein originally identified as a mediator of growth cone collapse and can modify axon number, length, and neuronal polarity.

CRMP-2 interacts with CaV2.2 and that overexpression of CRMP-2 leads to increased surface expression of CaV2.2, enhanced $Ca^{2+}$ currents, and stimulated release of CGRP from DRG. In contrast, knockdown of CRMP-2 dramatically reduces $Ca^{2+}$ currents and transmitter release. As reported herein uncoupling the CRMP-2-CaV2.2 interaction leads to a physiologically relevant decrease in $Ca^{2+}$ current and neurotransmitter release (FIG. 1A) and, in turn, suppresses persistent inflammatory and neuropathic hypersensitivity.

Characterization of a CRMP-2-$Ca^{2+}$ channel uncoupling peptide.

Figure 12A:
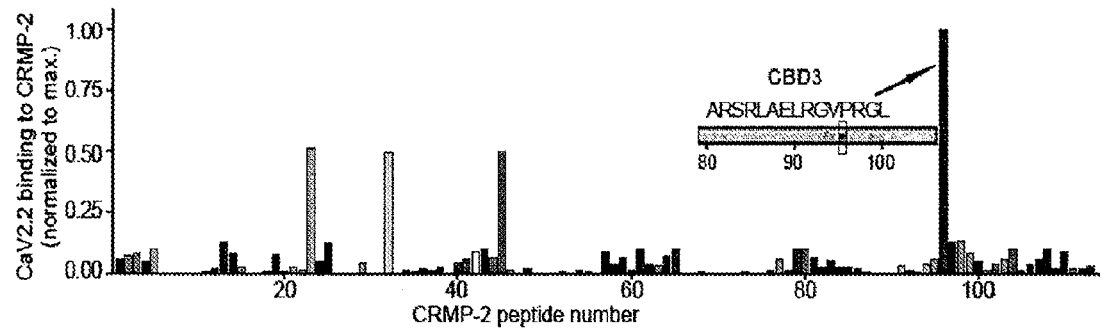
FIG. 12A. Normalized binding between CaV2.2 and CRMP-2 measured at different CRMP-2 peptides.
Figure 12B:
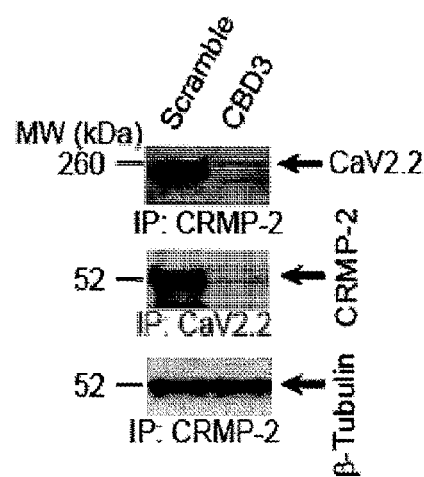
FIG. 12B. Immunoprecipitations with either CRMP-2 or CaV2.2 antibody.
Figure 12C:
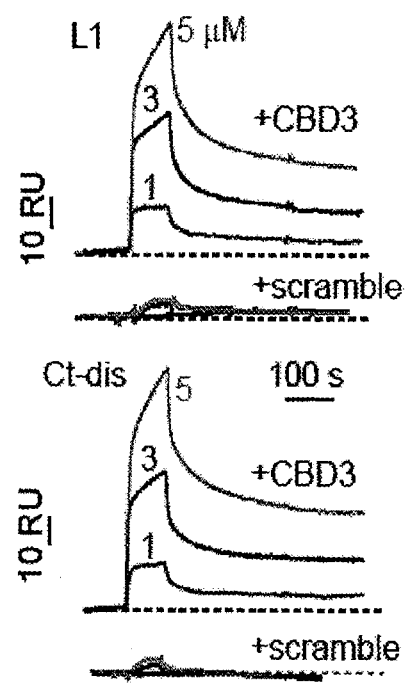
FIG. 12C. Sensogram of CBD3, or scramble peptide binding to CaV2.2.
Figure 12D:
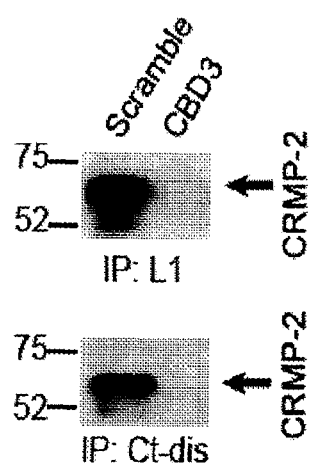
FIG. 12D. Antibody analysis of the binding of L1-GST and Ct-dis-GST fusion proteins to CRMP-2 measured in presence of either TAT Scramble or CRMP-2.
Figure 12E:
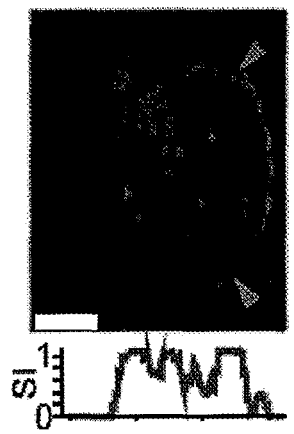
FIG. 12E. Image showing CaV2.2 on surface of CAD cells.
Figure 12F:
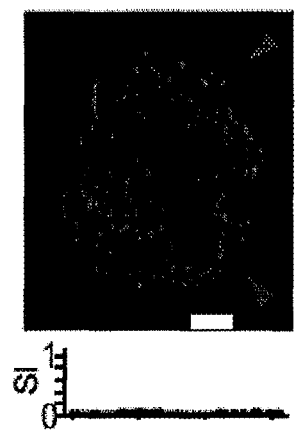
FIG. 12F. Image showing CaV2.2 is not detected on cell surface when CBD2 is over expressed.

In order to disrupt the interaction of CRMP-2 with the CaV2.2 complex in vivo, peptides covering the entire length of CRMP-2, including three CaV binding domains (CBDs1-3) previously identified as crucial for the CRMP-2-CaV2.2 interaction was synthesized. Referring now to (FIG. 12). A CRMP-2 peptide suppresses CaV2.2-CRMP-2 interaction. (FIG. 12A) Normalized binding of CaV2.2 to 15-mer peptides (overlapping by 12 amino acids) encompassing full-length CRMP-2 overlaid with spinal cord lysates. Sequence of peptide #96, designated CBD3, is shown. (FIG. 12B) Immunoprecipitation (IP) with recombinant CRMP-2 or CaV2.2 antibody from spinal cord lysates in the presence of scramble or CBD3 peptides failed to pull-down CaV2.2 (top) and CRMP-2 (middle) but not β-tubulin (bottom). (FIG. 12C) Sensorgram of CBD3 (1/3/5 µM; solid traces) or scramble peptide (1/3/5 µM; dotted traces) binding to CaV2.2 cytosolic loop 1 (L1) and distal C-terminus (Ct-dis). Dissociation was monitored for 4 min. RU, resonance units. (FIG. 12D) Binding of L1-GST and Ct-dis-GST fusion proteins to CRMP-2 in the presence of scramble or CBD3 peptides (10 µM). CRMP-2 bound to L1 and Ct-dis was probed with a CRMP-2 antibody. CaV2.2 is detected on surface of CAD cells (FIG. 12E) but not when CBD3 is over-expressed (FIG. 12F). Scale bars: 10 µm om in FIGS. 12E and 12F. Below, normalized surface intensity (SI) between arrows demarcating surface of cells shown. (FIG. 12H) Summary of percent of cells exhibiting surface CaV2.2 expression (n>100). (FIG. 12I) Immunoblots of biotinylated (surface) fractions of CAD cells expressing vector (scramble), an N-terminal region of CRMP-2 (CBD1), or CBD3 probed with CaV2.2 antibody (n=3). (FIG. 12J) Top, voltage protocol. Bottom, exemplar traces from hippocampal neurons overexpressing vector (EGFP), CRMP-2 or CRMP-2+CBD3. (FIG. 12K) Peak current density (pA/pF), at +10 mV, for CRMP-2– and CRMP-2+CBD3– transfected neurons. *, p<0.05 versus CRMP-2, Student's t-test. It was found that a CRMP-2 peptide (residues 484-498), CBD3, bound to CaV2.2 (FIG. 12A). Immunoprecipitations from spinal cord lysates demonstrated that CBD3 peptide inhibited the CRMP-2–CaV2.2 interaction (FIG. 12B; top, middle) but did not affect the interaction between tubulin and CRMP-2 (FIG. 12B, bottom). Since CRMP-2 binds the first intracellular loop (L1) and the distal C-terminus (Ct-dis) of CaV2.2, whether CBD3 bound these regions was investigated.

Figure 18A:
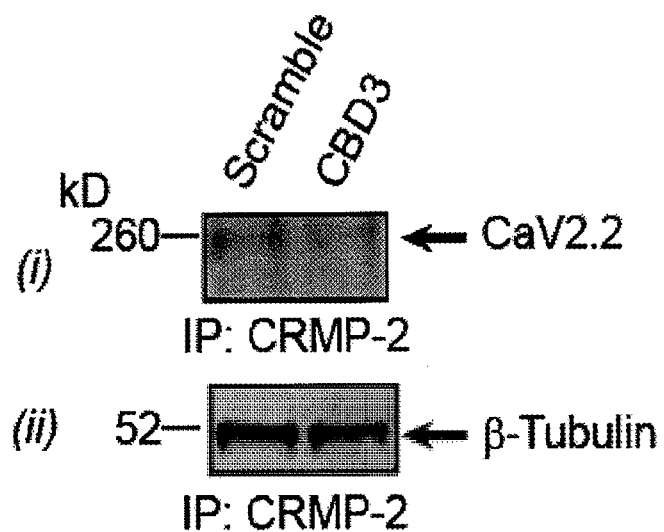
FIG. 18A. Immunoprecipitation of recombinant CRMP-2-His in the presence of TAT-Scramble or CBD3.
Figure 18B:
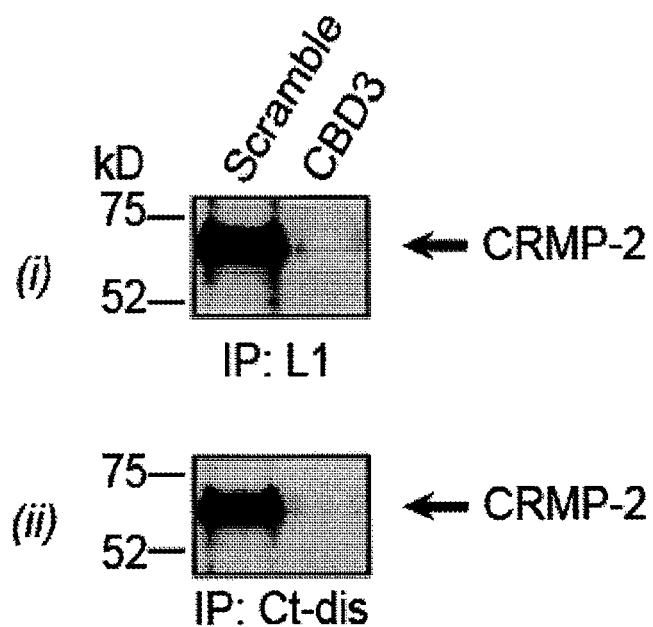
FIG. 18.B. Immunoprecipitation: in vitro binding of Li-GST and Ct-dis-GST fusion proteins to CRMP-2.

Referring now to FIG. 18. CBD3 peptide inhibits the binding between CRMP-2 and CaV2.2. (FIG. 18.A) Immunoprecipitation (IP) with recombinant CRMP-2-His protein in the presence of scramble or CBD3 peptides reduced the amount of CaV2.2 (i) but not β-tubulin (ii) that could be captured from rat brains. Peptides (10 µM each) were added for 30 min prior to addition of the CRMP-2-His protein. Representative blot from 12 separate experiments is shown. (FIG. 18.B) In vitro binding of L1-GST and Ct-dis-GST fusion proteins to CRMP-2 in the presence of scramble or CBD3 peptides (10 µM). The purification of the L1 and Ct-dis regions of CaV2.2 has been described by us previously. CRMP-2 bound to L1 and Ct-dis was probed with a CRMP-2 antibody. Representative blot from 4 separate experiments are shown. Similar results were obtained in experiments with spinal cord lysates (FIGS. 18.B and 18D). Using surface plasmon resonance, it was determined that CBD3 peptide, but not a scramble peptide, bound to immobilized L1 and Ct-dis proteins (FIG. 12C). Moreover, the CBD3 peptide disrupted the interaction between CRMP-2 and L1 or Ct-dis regions (FIG. 12.D. and FIGS. 18B and 18C).

Figure 12G:
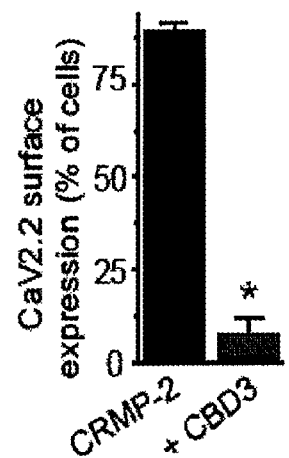
FIG. 12G. Bar graph CaV2.2 surface expression measured after exposure to either CRMP-2 or CBD3.
Figure 12H:
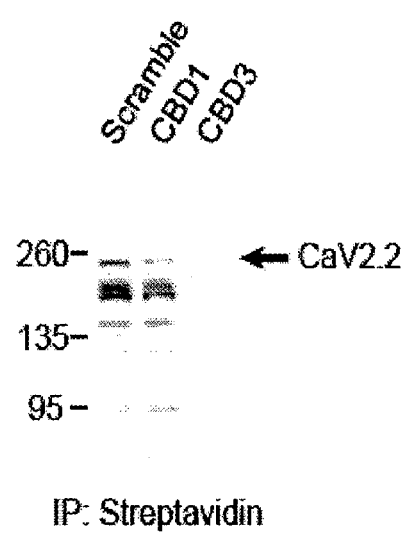
FIG. 12H. Gel showing level of CaV2.2 measured in presence of one of the following: Scramble or CBD3.
Figure 12I:
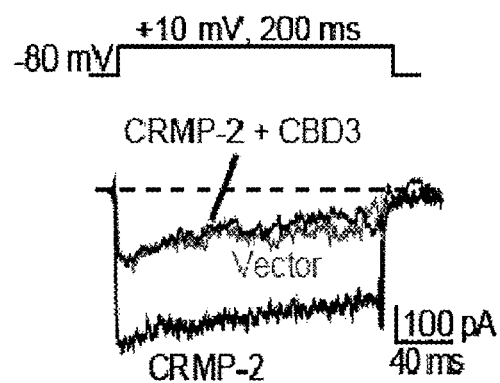
FIG. 12I. Ca2+ currents from neurons transfected with vector, CRMP-2 or CRMP2+CBD3.
Figure 12J:
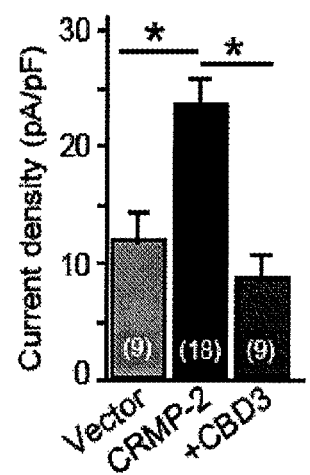
FIG. 12J. Bar graph current density measured after treatment with one of the following: vector, CRMP-2 or CRMP-2+CBD3.
Figure 19A:
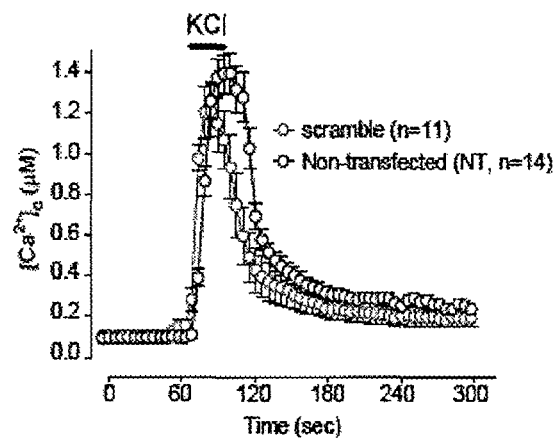
FIG. 19.A. Calcium release versus time measured in untreated cells and cells treated with Scramble.
Figure 19B:
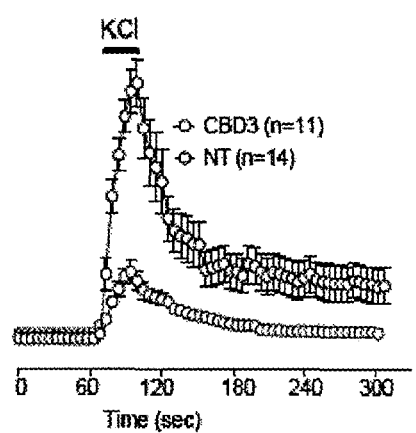
Figure 19C:
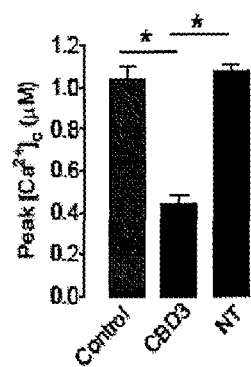

Because CRMP-2 facilitates surface CaV2.2 trafficking, CBD3 was tested to determine if could uncouple CRMP-2 from CaV2.2 to affect trafficking, surface expression, CaV2.2 activity, and $Ca^{2+}$ influx. Co-expression of CaV2.2 with CBD3 in the CAD neuronal cell line resulted in almost complete retention of the channel in cytoplasmic aggregates (FIGS. 12E-12G). Surface biotinylation in CAD cells showed expression of CBD3, but not scramble or CBD1, prevented surface expression of co-expressed CaV2.2 (FIG. 12H). Further, co-expression of CRMP-2 with CBD3 in hippocampal neurons eliminated the CRMP-2-mediated increase in CaV2.2 current density (FIGS. 12I and 12J) and expression of CBD3, but not a scramble control, reduced depolarization-induced calcium influx in hippocampal neurons FIGS. 19A to 19C). Thus, it appears that in vitro, CBD3 disrupts the CRMP-2-CaV2.2 interaction, affects CaV2.2 trafficking, and $Ca^{2+}$ current density.

Referring now to FIG. 19. Overexpressed CBD3 or TAT-CBD3 reduces $Ca^{2+}$ influx predominantly via N-Type $Ca^{2+}$ channels. (FIGS. 19.A and 19.B) hippocampal neurons cultured for 5 days in vitro were transfected with DNA constructs encoding CBD3 or a scramble sequence using Lipofectamine, and then loaded with the ratiometric $Ca^{2+}$-sensitive dye Fura-2AM (3 µM). Changes in $[Ca^{2+}]c$, in response to plasma membrane depolarization with potassium chloride (KCl, 30 mM), were recorded using time-lapse, wide-field fluorescence microscopy. Averaged $[Ca^{2+}]c$, responses obtained from neurons expressing plasmid encoding a scramble sequence (scramble) or the CBD3 sequence (CBD3) and from neurons not transfected (NT). In both panels, n indicates the number of neurons from which Fura-2 fluorescence was recorded. (FIG. 19.C) Summary of average peak c responses from control (n=11) and CBD3 (n=11) or NT (n=14 per condition) neurons. (FIG. 19.D) $Ca^{2+}$ influx was monitored in DRG neurons using Fura-2AM. Neurons were loaded with Fura-2AM for 25 minutes at room temperature before being treated with vehicle (0.05% DMSO), 10 µM TAT-Scramble, or TAT-CBD3 for 10 minutes. DRGs were then bathed in the presence of the L-type channel blocker Nifedipine (10 µM; left two bars) or in the presence of L- and N-type blockers (10 µM Nifedipine+2 µM ω-CTX; right two bars) for the duration of the imaging experiments. Changes in the Fura-2 $F_{340}/F_{380}$ were monitored for 10 min following stimulation with 45 mM KCl. Values represent the average max $\Delta(F_{340}/F_{380})$ normalized to vehicle treated cells (either Nifedipine treated or Nifedipine+ω-CTX)±SEM for n>100 cells from 4 separate experiments, statistical significance is indicated by an asterisk (p<0.05; Student's t-test).

Referring now to FIG. 13. TAT-CBD3 reduces $Ca^{2+}$ currents in DRGs and excitatory synaptic transmission in lamina II neurons from spinal cord slices. (FIG. 13A) Representative differential interference contrast/fluorescence images showing robust penetration of FITC-TAT-CBD3 into DRGs (arrowheads) but not other cells (arrows). Nuclei are stained with Hoechst dye in lower panel. Scale bars: 10 µm. (FIG. 13B) Representative current traces from a DRG incubated for 15 min with TAT-Scramble (10 µM; green) or TAT-CBD3 (10 µM; purple) in response to voltage steps illustrated above the traces. (FIG. 13C) Current-voltage relationships for the currents shown in b fitted to a b-spline line. Peak currents were normalized to the cell capacitance. (FIG. 13D) Peak current density (pA/pF) measured at −10 mV for DRGs incubated with TAT-Scramble, TAT-CBD3 or TAT-CBD3+1 μM ω-CTX. The numbers in parentheses represent numbers of cell tested. *, p<0.05 versus TAT-Scramble. (FIG. 13E) Representative traces of spontaneous EPSCs (sEPSCs) in lamina II neurons in spinal cord slices before treatment (left traces), after application of 10 μM TAT-Scramble peptide (middle traces) or 10 μM TAT-CBD3 peptide (right traces). Lower panels are enlarged traces. Voltage-clamp recordings (holding voltage=−70 mV) were used to record synaptic responses. (FIG. 13F) Ratio of sEPSC frequency and amplitude. *, p<0.05, compared with baseline. Note the significant decrease in the frequency but not amplitude of sEPSCs after the application of TAT-CBD3 peptide.

Figure 13A:
FIG. 13A. Differential interference contrast/fluorescence image illustration of the penetration of FITC-TAT CBD3 into DRG cells FIG. 13B. Current traces of DRG cells incubated with TAT scramble or with TAT-CBD3.
Figure 13B:
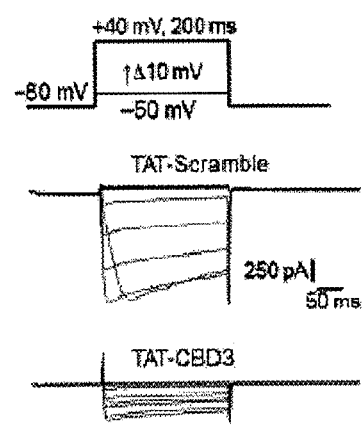
FIG. 13C. Plot of current density versus membrane potential of DRG cells incubated with TAT scramble or with TAT-CBD3.
FIG. 13D. Bar graph illustrating peak current density measured using DRG cells incubated with TAT-scramble, TAT-CBD3 or TAT CBD3.
FIG. 13E. Traces of EPSCs in lamina II neurons after application of either control TAT-scramble or TAT-CBD3
FIG. 13F. Bar graph illustrating ratio of sEPSC, frequency and amplitude measured using either TAT scramble or TAT CBD3 peptide.
Figure 13C:
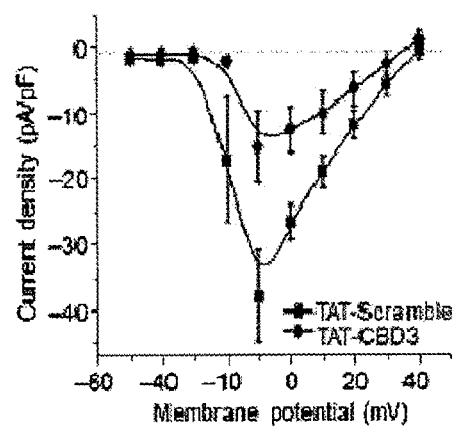
Figure 13D:
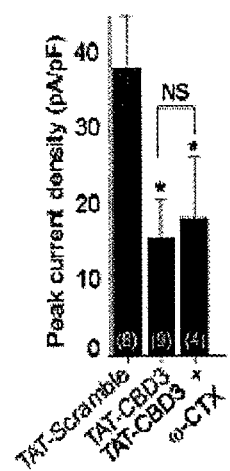
Figure 19D:
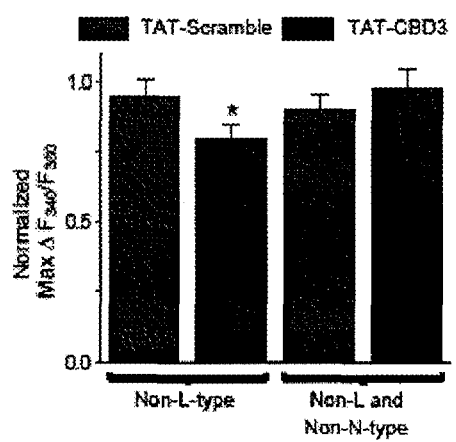
Figure 20A:
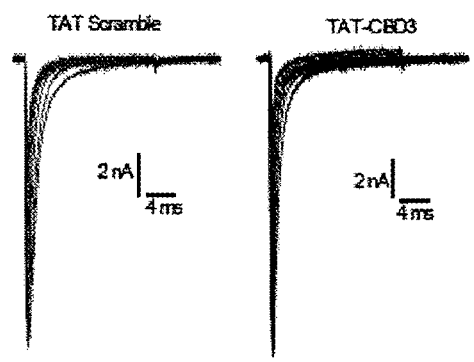
FIG. 20.A. Traces of change in amps versus time measured after exposure to TAT-Scramble or TAT-CBD3.
Figure 20B:
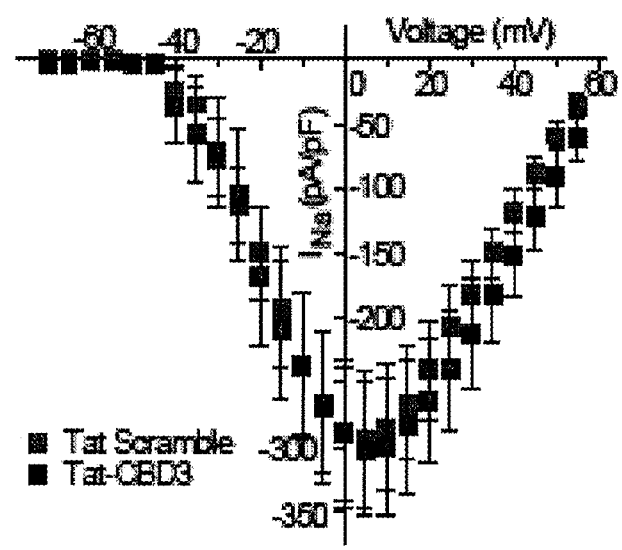
Figure 20C:
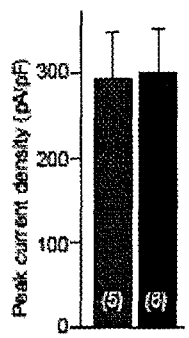
Figure 20D:
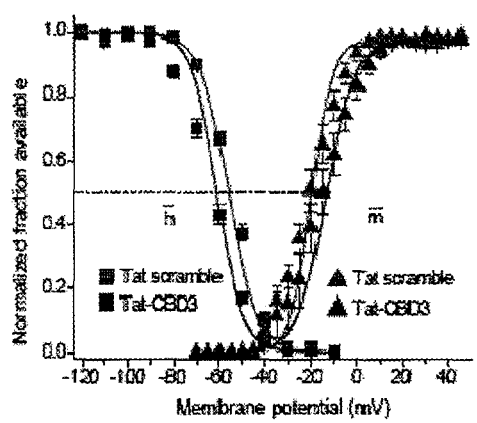
Figure 20E:
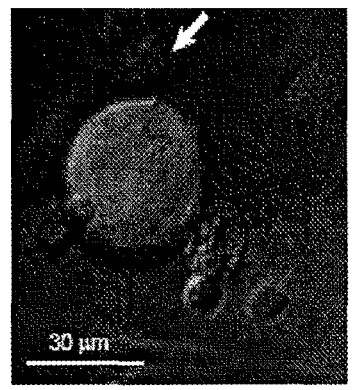

CBD3 was rendered cell-permeant by fusion with the transduction domain of human immunodeficiency virus-1 (HIV-1) TAT protein, generating TAT-CBD3 which readily entered neurons (FIG. 13A). A 15 min application of TAT-CBD3 to DRGs reduced $Ca^{2+}$ currents by ~60% which were not further blocked by addition of the CaV2.2 blocker ω-conotoxin (1 μM) (FIGS. 13E and 13D), suggesting selectivity of TAT-CBD3 for N-type channels. Qualitatively similar results were obtained from calcium imaging in DRGs: TAT-CBD3 reduced $K^+$-evoked $Ca^{2+}$ influx selectively through N-type channels (FIG. 19D). Importantly, TAT-CDB3 did not affect sodium current density or gating in DRGs (FIG. 20).

Referring now to FIG. 20. TAT-CBD3 does not affect $Na^+$ currents in DRG neurons. (FIG. 20.A) Representative sodium current traces from dorsal root ganglion (DRG) neurons elicited using an incremental 15 ms depolarization step protocol between −70 mV to +50 mV from a holding potential of −80 mV. For clarity, only traces from −20 to −70 are illustrated. Currents responses of DRGs treated for 5 min with 10 μM TATScramble (left) or 10 μM TAT-CBD3 peptides (right). (FIG. 20.B) Summary of current-voltage (IV) relationships for DRG neurons treated with TAT scramble or TAT-CBD3 illustrated in (FIG. 20.A) (n=5-6). (FIG. 20.C) Peak current density (pA/pF) measured at +5 mV for DRG neurons treated with TAT-Scramble (n=5) or TAT-CBD3 (n=6). (FIG. 20.D) Normalized fraction of channels available (G/V) during steady-state activating (m∞/V) and fast-inactivating (h∞/V) protocols. The fast-inactivation protocol consisted of holding cells at −80 mV, stepping to inactivating prepulse potentials ranging from −120 to −10 mV (in 10-mV increments) for 500 ms, before stepping the cells to 0 mV for 20 ms to measure the available current. A 500 ms conditioning pulse was used as it allows all of the endogenous sodium channels to transition to a fast-inactivated state at all potentials assayed in these cells. There were no significant differences in the midpoints (V1/2) and slope factors (k) of activation or inactivation between the two conditions (p>0.05; Students' t-test). (FIG. 20.E) Representative deconvolved image of a DRG neuron treated for 5 min with FITC-TAT-CBD3 illustrating complete penetration of the peptide (as gauged by the FITC fluorescence (green) within the cell). The differential interference contrast (DIC) image is superposed with the fluorescence image to illustrate the stark absence of peptide in non-neuronal cells (see example of cell with white arrow). Nuclei are identified with Hoechst stain (blue). Scale bar: 30 μm.

Figure 13E:
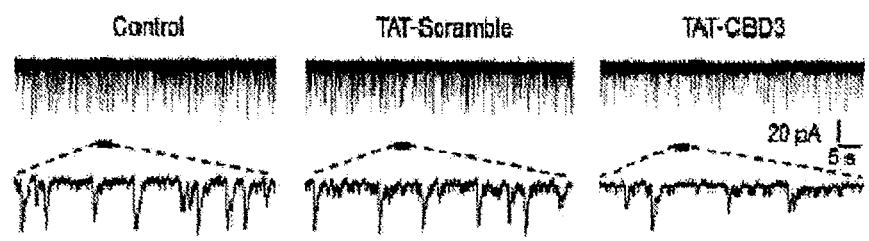
Figure 13F:
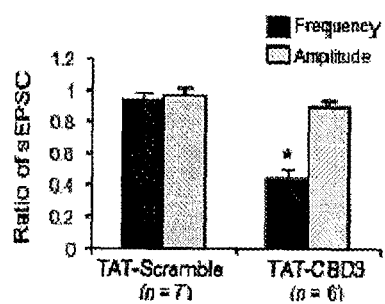

To determine if uncoupling CRMP-2 from CaV2.2 with TAT-CBD3 modulates synaptic transmission, patch-clamp recordings in spinal cord slices were made in order to measure synaptic responses in lamina II neurons (FIGS. 13E and 13F) receiving input from C-fiber primary afferents expressing CaV2.2. The sEPSCs in these neurons are caused by glutamate release and reflect presynaptic (frequency change) and postsynaptic mechanisms (amplitude change). Perfusion of spinal cord slices with TAT-CBD3 reduced sEPSCs frequencies by 57% without changing amplitudes, supporting a presynaptic action (FIG. 13F). In contrast, TAT-Scramble had no effect on excitatory postsynaptic currents (eEPSC) frequency (FIGS. 13E and F). Recordings from layer V pyramidal neurons in cortical brain slices also showed reduced glutamate release probability from stimulated presynaptic terminals in the presence of TAT-CBD3 (FIG. 21).

Figure 21A:
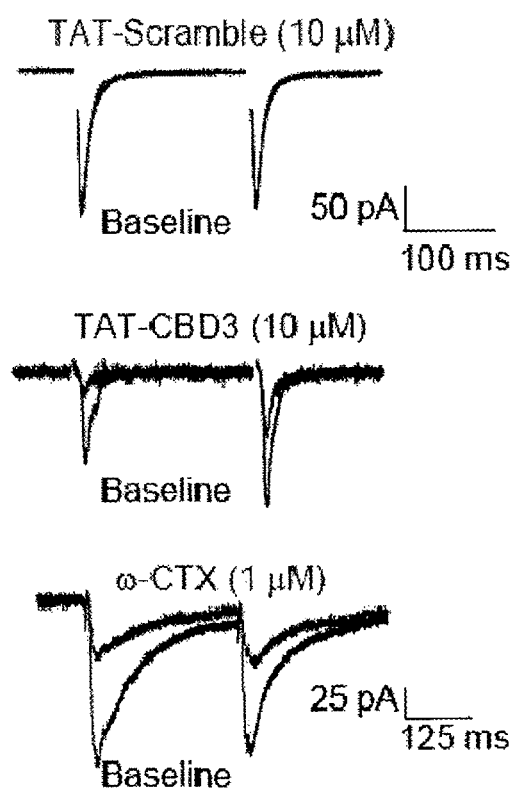
FIG. 21.A. Traces of eEPSCs measured in cortical layers of pyramidal neurons after various treatments: TAT-Scramble, TAT-CBD3, or ω-CTX.
Figure 21B:
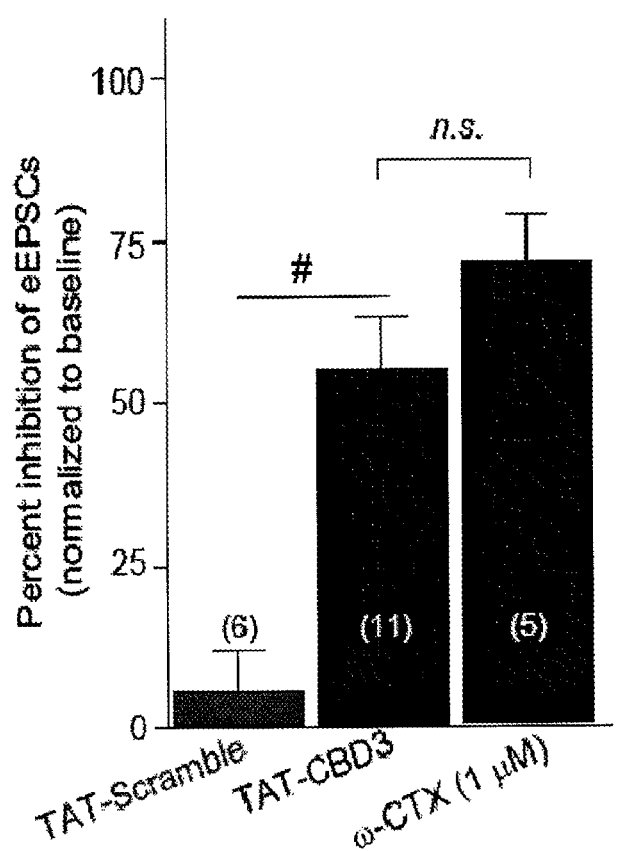
Figure 21C:
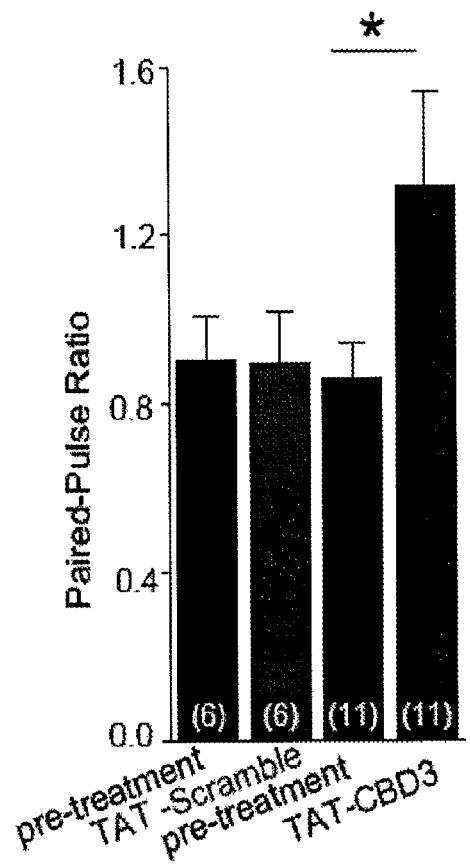
Figure 22A:
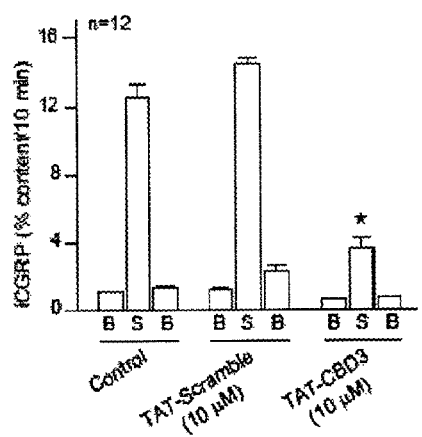
FIG. 22.A. Bar graph of iCGRP release measured untreated DRG neurons and neurons treated with TAT-Scramble or TAT-CBD3.
Figure 22B:
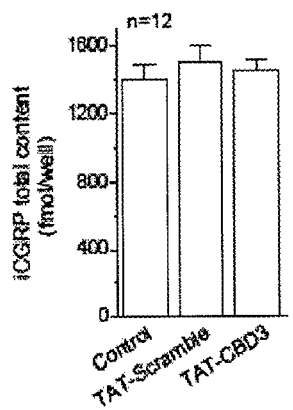
Figure 22C:
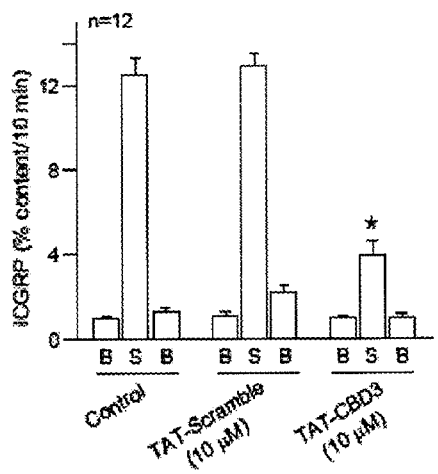
Figure 22D:
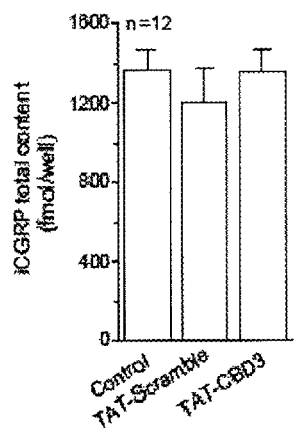
Figure 22E:
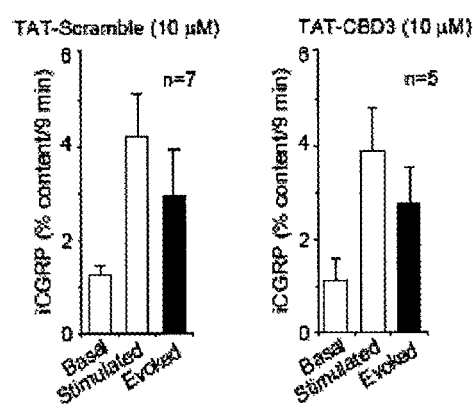
Figure 22F:
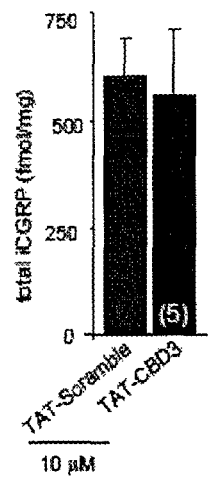
Figure 22G:
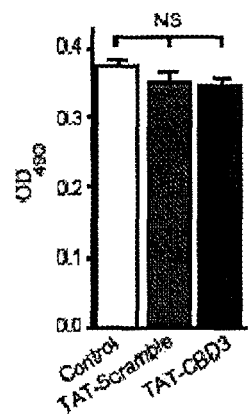
Figure 23A:
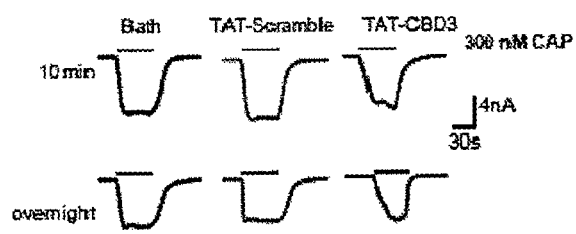
FIG. 23.A. Nondesensitizing current traces via TRPVI channels in response to capsaicin and treated with nothing (bath), TAT-Scramble or TAT-CBD3.
Figure 23B:
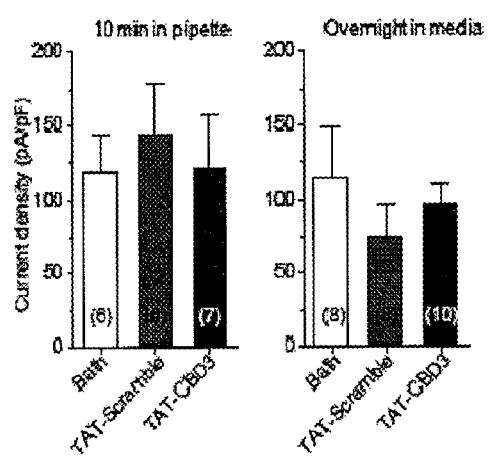
Figure 23C:
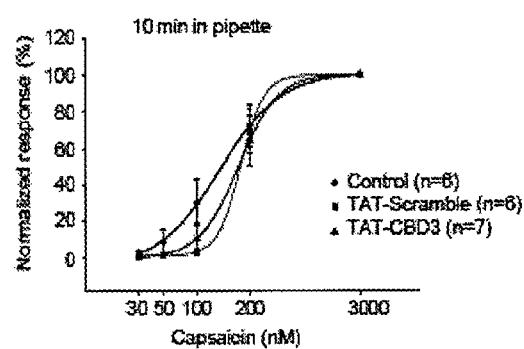
Figure 23D:
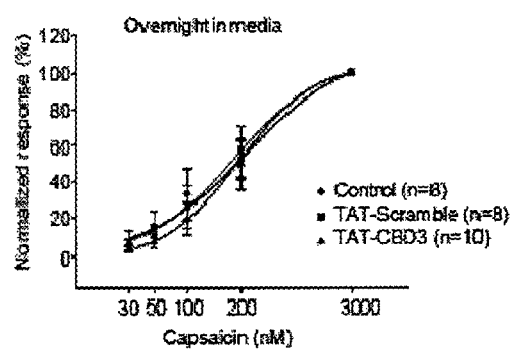
Figure 23E:
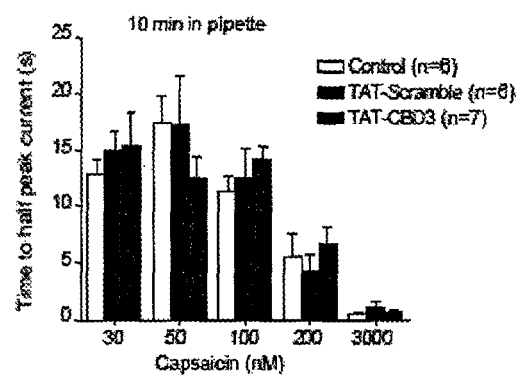
Figure 23F:
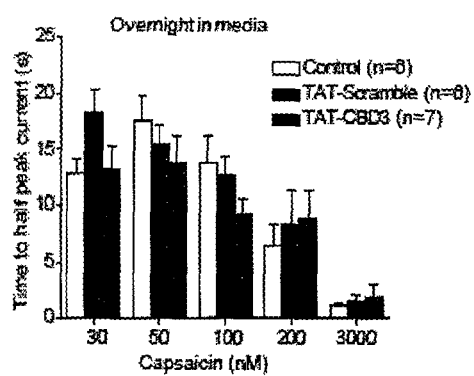
Figure 24A:
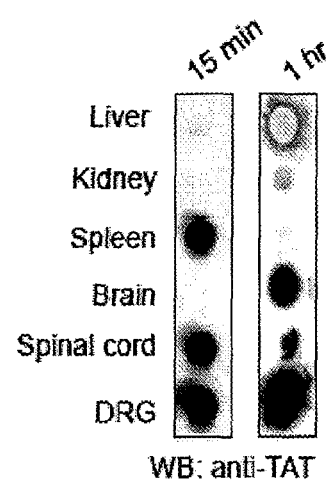
FIG. 24.A. Dot blot analysis of TAT-CBD3 peptide distribution in rat tissue.
Figure 24B:
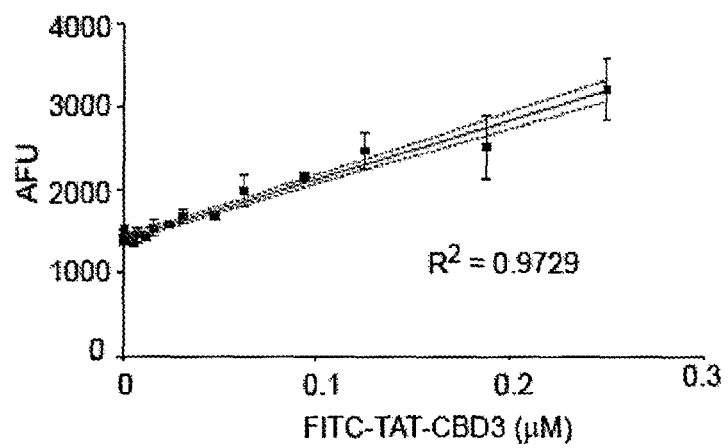
Figure 24C:
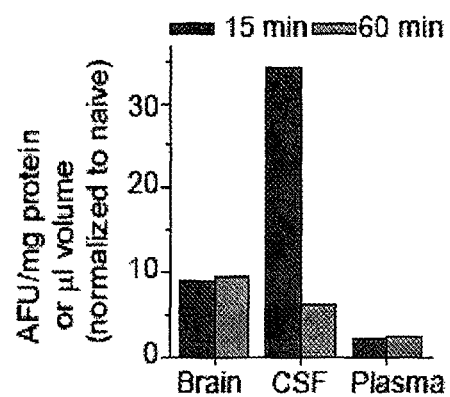
Figure 24D:
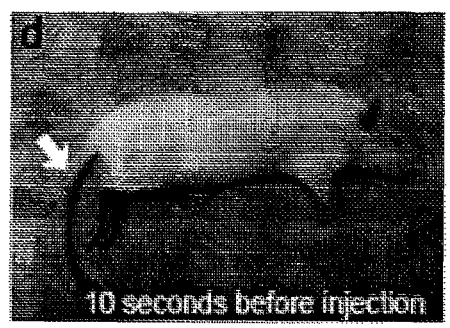
Figure 24E:
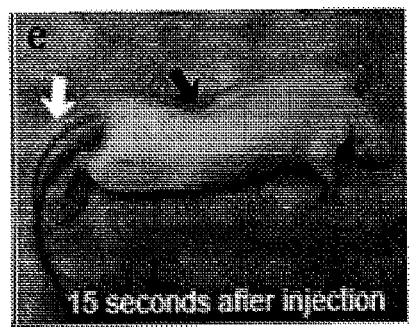
Figure 24F:
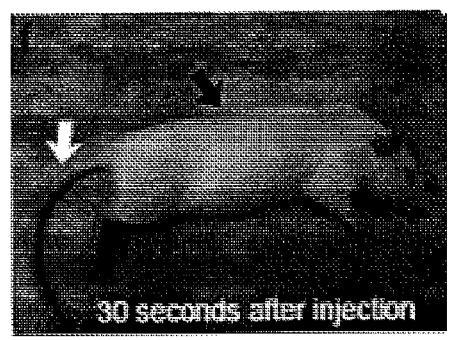
Figure 24G:
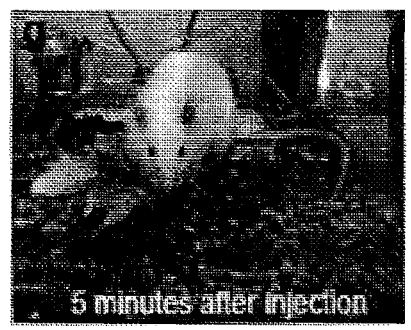
Figure 24H:
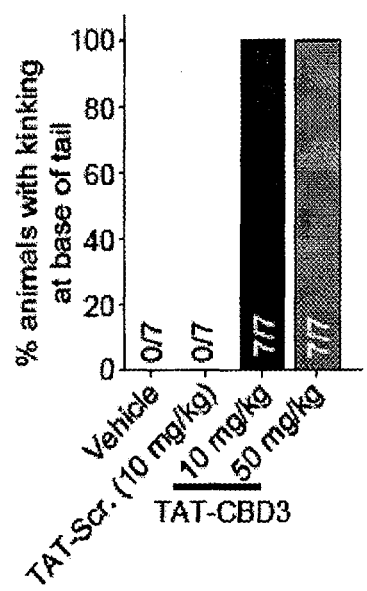

Referring now to (FIG. 21). TAT-CBD3 reduces eEPSC amplitude in cortical slices. (FIG. 21.A) Representative traces of evoked eEPSCs in cortical layer V pyramidal neurons to 5 Hz stimulus at baseline (black traces), and after application of 10 μM TAT-Scramble peptide (green traces), 10 μM TAT-CBD3 peptide (purple traces), or 1 μM ω-conotoxin (ω-CTX; red traces). Voltage-clamp recordings (Vh=−70 mV) were used to record synaptic responses and stimulus intensities were in the range of 120-300 μA, about 2 times the threshold stimulus. (FIG. 21.B) Summary of percent inhibition of peak eEPSC in the presence of 10 μM TAT-Scramble (n=6), 10 μM TATCBD3 (n=11), and 1 μM ω-CTX (n=5). Note the significant decrease in amplitude of evoked EPSCs after the application of TAT-CBD3 peptide (#, p<0.05). (FIG. 21.C) TAT-CBD3 peptide significantly increased paired-pulse ratio (PPR). PPR was calculated by dividing eEPSC amplitude elicited by a second pulse from that of the first pulse (P2/P1). *, p<0.05 for TAT-CBD3 versus pretreatment (Student's t-test).

TAT-CBD3 Reduces Evoked CGRP Release.

Referring now to FIG. 22. Effects of TAT-CBD3 on $K^+$- or Capsaicin-stimulated transmitter release in DRG neurons and spinal cord slices without affecting cell viability. Adult mouse DRG neurons were maintained in culture for 5-7 days prior to the release experiments. (FIG. 22.A) Bar graph of immunoreactive calcitonin gene-related peptide (iCGRP) release expressed as mean percent total iCGRP content of cells in each well±s.e.m. (n=12 wells/condition). Neuropeptide release was measured from cells treated with normal HEPES buffer containing 3.5 mM KCl (basal, B), HEPES buffer containing 50 mM KCl (S), and HEPES buffer containing 3.5 mM KCl again. DRGs were exposed to TAT-Scramble or TAT-CBD3 peptides, at 10 μM, overnight (FIGS. 22.A and 22.B) or were included in the 10 minutes prior to and throughout the high K+ exposures (FIGS. 22.C and 22.D). The resulting total TAT peptides exposure time was 12 h and 20 minutes (FIGS. 22.A and 22.B) or 30 min (FIGS. 22.C and 22.D). Asterisks (*) indicate statistically significant differences in iCGRP release between TAT-CBD3 and the control (no treatment) or TAT-Scramble using an ANOVA with Dunnett's post-hoc test (p<0.05). In all cases, release stimulated by high extracellular $K^+$ was significantly higher than basal release. (FIGS. 22.B and 22.D) The total content of iCGRP measured at the end of the release experiment. There were no significant differences in iCGRP content between the conditions tested. (FIG. 22.E) Summary of iCGRP release from spinal cord slices. iCGRP release from spinal cord slices was measured in three 3-min exposures to Hepes buffer alone, Hepes buffer containing 500 nM capsaicin, then five 3-min exposures to Hepes alone to re-establish baseline. Each column is the mean±SEM of the percent of total peptide released/min (n=5-7 animals per condition). TAT-Scramble or TAT-CBD3 (FIG. 22.E), at 10 μM, was included in the six 3-min incubations prior to the final Hepes exposures, for a total exposure time of 18 min. TAT-Scramble or TATCBD3 did not affect basal release of iCGRP. Evoked release, or release due to capsaicin stimulation alone, is compared between TAT treatments. The evoked release was obtained by subtracting iCGRP release during three basal fractions (12 to 18 min) from that during the three capsaicin-stimulated fractions (21 to 27 min) and expressing it as percent of total iCGRP content in each treatment group. In all cases, release stimulated by capsaicin was significantly higher than basal release. (FIG. 22.F) Total content of iCGRP (in fmol/mg) tissue released during the perfusion and the amount remaining in the tissues measured at the end of the release experiments. Spinal cord release data for 20 µM TAT peptides is shown in FIG. 3. (FIG. 22.G) Cultured dorsal root ganglion neurons were treated with TAT-Scramble or TAT-CBD3 (10 µM) for 12 h and then neuronal survival was assessed using the MTT colorimetric assay. Data represent means±S.E.M. percent absorbance at 490 nm relative to control (0.01% DMSO, dimethylsulfoxide; Sigma) (n=8 wells per condition). Neither TAT peptide affected cell viability (p>0.05; Students' ttest; N.S., not significant).

Calcium entry through presynaptic CaV2.2 on small-diameter sensory neurons is directly coupled to transmitter release. The ability of {Yamamoto, 2009 1/id} TAT-CBD3 to modulate release of iCGRP from dissociated DRG neurons treated with 10 µM peptides was tested. Pretreatment with TAT-CBD3, but not TAT-Scramble, for 20 min or 12 h reduced CGRP release evoked by 50 mM potassium chloride, without affecting resting release (FIG. 22A to 22D). Furthermore, total CGRP content was unaffected by the peptides. Cell viability, measured after 12 h incubation, was not affected by any treatments (FIG. 22).

Referring now to FIG. 14. TAT-CBD3 reduces capsaicin-stimulated release of iCGRP from spinal cord slices. iCGRP release was measured in three 3-min exposures to Hepes buffer alone (white bars), to Hepes buffer with peptides (white bars), to Hepes buffer containing 500 nM capsaicin with peptides (yellow bars), then to Hepes alone to re-establish baseline (white bars). Each column represents the mean±SEM of iCGRP levels in each 3-min perfusate sample, expressed as percent of total peptide content in the tissues per minute (n=7 animals). TAT-Scramble (FIG. 14A) or TAT-CBD3 (FIG. 14B), at 20 µM, was included as indicated by the horizontal bars. *, p<0.05 versus basal iCGRP release in the absence of capsaicin (ANOVA, Dunnett's post-hoc test). Neither peptide altered basal iCGRP release (not significant; NS.). (FIG. 14C) Basal release is the amount of iCGRP released in the 3 fractions exposed to Hepes plus peptides. Stimulated release is the amount of iCGRP released in the 3 fractions exposed to 500 nM Cap+peptides. The evoked release was obtained by subtracting iCGRP release during three basal fractions (12-18 min) from that during the three capsaicin-stimulated fractions (21-27 min) and expressing it as percent of total iCGRP content in each group. In all cases, release stimulated by capsaicin was significantly higher than basal release. & and #, p<0.05 versus the respective TAT-Scramble using a Student's t-test. (FIG. 14D) Total content of iCGRP (in fmol/mg) is the sum of CGRP released during perfusion and from cord tissue measured at the end of the release experiments.

Figure 14A:
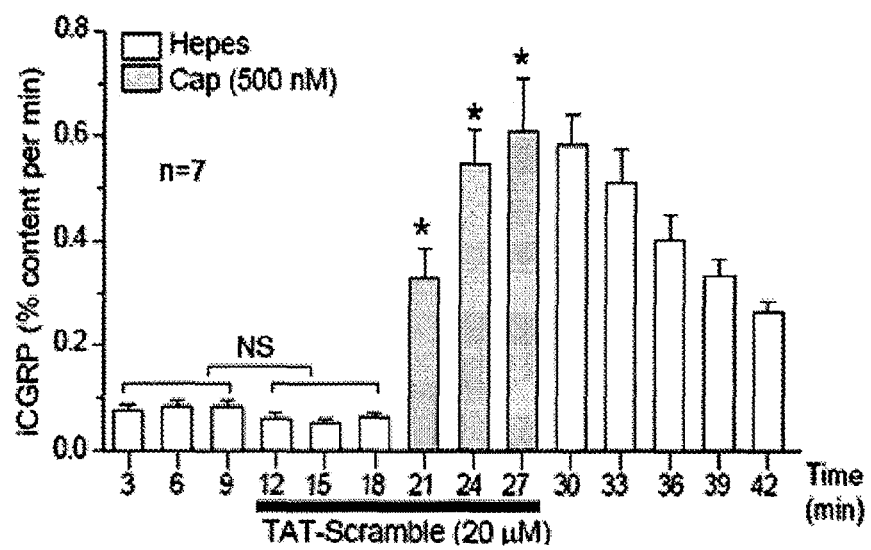
FIG. 14A. Bar graph showing iCGRP released from spinal cord slices measured with exposure to TAT-scramble.
Figure 14B:
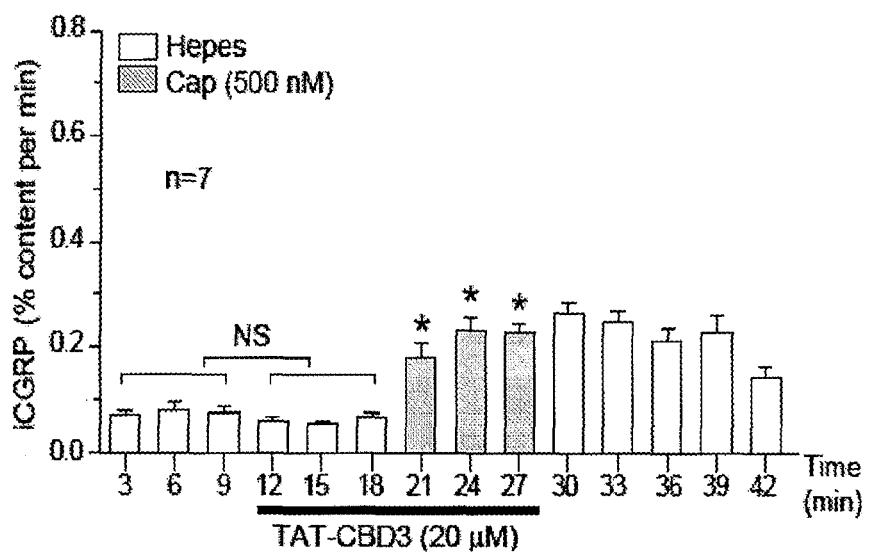
FIG. 14B. Bar graph showing iCGRP released from spinal cord slices measured with exposure to TAT-CBD3.
Figure 14C:
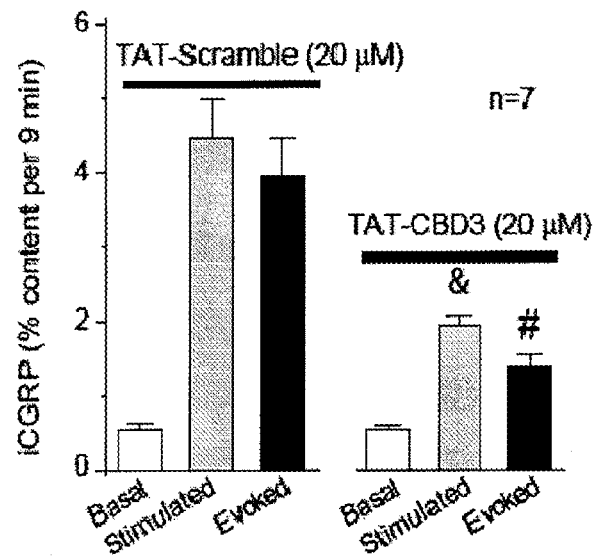
FIG. 14C. Bar graph showing iCGRP released from spinal cord slices after exposure to different conditions.
Figure 14D:
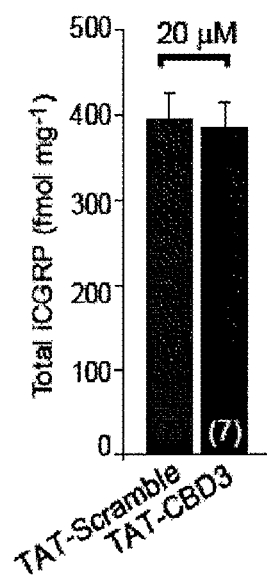
FIG. 14D. Bar graph total iCGRP released at the conclusion of release experiments measured with either TAT Scramble or TAT-CBD3.

The effect of TAT-CBD3 on capsaicin-evoked CGRP release from spinal cord slices was examined. This release occurs primarily from central terminals of neurons expressing the transient receptor potential vanilloid type 1 (TRPV1) channel which has been shown to be important in pain transduction. Perfusion with peptides did not change basal iCGRP release (FIGS. 14A and 14B). However, perfusion with 20 µM, but not 10 µM (FIGS. 22E and 22F), TAT-CBD3 led to a decrease in capsaicin-evoked iCGRP release compared to TAT-Scramble (FIG. 14C) with no differences in iCGRP total content (FIG. 14D).

Referring now to FIG. 23. TAT-CBD3 does not affect capsaicin-evoked TRPV1 response in rat DRG neurons. (FIG. 23.A) Representative non-desensitizing current traces of TRPV1 in response to 300 nM capsaicin after vehicle control DMSO (bath), TAT-Scramble, or TAT-CBD3 peptide treatment for 10 minutes (administered via the recording pipettes) or overnight (12-16 hours in culture medium). Consistent with previous reports, subtle differences in opening times of TRPV1 channels can be observed between the conditions (also see below). These are likely due to the differential access of capsaicin, a relatively hydrophobic molecule, across the lipid membrane. (FIG. 23.B) Cumulative summary data of peak current density (pA/pF) in response to 300 nM capsaicin after 10 minutes (left) or overnight exposure (right) to vehicle control DMSO (white bars), TAT-Scramble (green bars), or TAT-CBD3 peptide (purple bars). Data are presented as means±S.E.M. Number of cells shown in parentheses. (FIG. 23.C) Cumulative summary data of peak current density (pA/pF), normalized to the maximum capsaicin-evoked current, in response to various concentrations of capsaicin after 10 minutes (FIG. 23.A) or overnight exposure (FIG. 23.B) to vehicle control DMSO (black circles), TAT-Scramble (green squares), or TAT-CBD3 peptide (purple triangles). The numbers of cells for each condition are presented in parentheses. Lines represent best fits of the data. There were no differences in normalized capsaicin response at any of the capsaicin concentrations tested for control versus either peptide (Two way ANOVA; p=0.75 for 10 min conditions and p=0.07 for overnight in media conditions). Summary of the time needed to reach half-peak current amplitudes (in sec) in cells incubated with control or peptides for 10 min in pipette (FIG. 23.E) or overnight in media (FIG. 23.F). There were no differences in time to half-peak current in any of the capsaicin concentrations tested for control versus either peptide (Two way ANOVA; p=0.85 for 10 min conditions and p=0.38 for overnight in media conditions), suggesting that the rate of activation is not statistically different between then groups. The slightly differing opening rates evident in the traces with TAT-CBD3 are likely due to the cell-to-cell variability in the access of the hydrophobic capsaicin (8-methyl-N-vanillyl-6-nonenamide) molecule to the intracellular domain of the TRPV1 channel to elicit current. The traces shown in the initial panel a were selected to reflect currents that were representative of the average current densities for the three conditions. While other traces with more similar opening times were available, they were not necessarily the best representatives of the average densities. The lack of an effect of TAT-CBD3 on TRPV1 current recordings (peak amplitudes and activation rates) from DRG neurons shows that the actions of TAT-CBD3 are not via direct inhibition of TRPV1 channels.

TAT-CBD3 Affects Vasodilatation in Rat Dura Mater In Vivo.

Referring now to FIG. 15. TAT-CBD3 reduces meningeal blood flow changes in response to capsaicin. (FIG. 15A) Experimental paradigm for the Laser Doppler flowmetry measurements. (FIG. 15B) Representative normalized traces of middle meningeal blood flow changes in response to nasally administered capsaicin (Cap, 100 nM) in the presence of TAT-Scramble (30 µM, green trace) or TAT-CBD3 pretreatment (30 µM, purple trace, applied durally 15 minute prior to Cap administration). Laser Doppler flowmetry measurements were collected at 1 Hz and binned by averaging every 10 samples for graphical representation. The data from each animal was normalized to the first 3 minutes of basal data and the horizontal dashed line indicates the calculated baseline. The ordinate represents red blood cell flux measurements in arbitrary units (AU). (FIG. 15C) Summary of blood flow changes following nasal administration of Cap in the absence or presence of previous administration of TAT-CBD3 (3, 10 or 30 µM) or TAT-Scramble to the dura. The capsaicin-induced blood flow changes were CGRP-dependent as they could be blocked by prior dural administration of the CGRP antagonist, $CGRP_{8-37}$. Values are mean±S.E.M. *, p<0.05 versus vehicle (unpaired Student's t-test). The number of animals tested for each condition is indicated in parentheses. (FIG. 15D) Concentration-response curve of percent inhibition (versus averaged TAT-scramble) of blood flow yields an $IC_{50}$ of 3.1±1.1 µM (n=4-5).

Figure 15A:
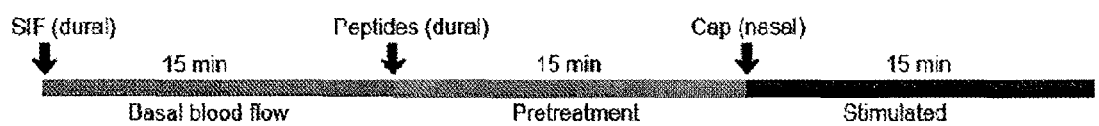
FIG. 15A. Schematic diagram of experiments for measuring the effect of various peptides on meningeal blood flow.
Figure 15B:
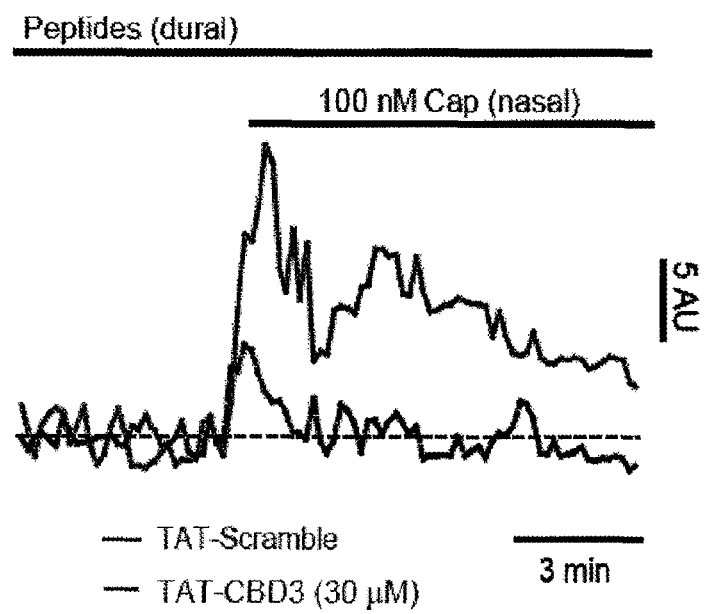
FIG. 15B. Traces showing meningeal blood flows measured after capsaicin challenge and exposure to either TAT Scramble or TAT-CBD3.
Figure 15C:
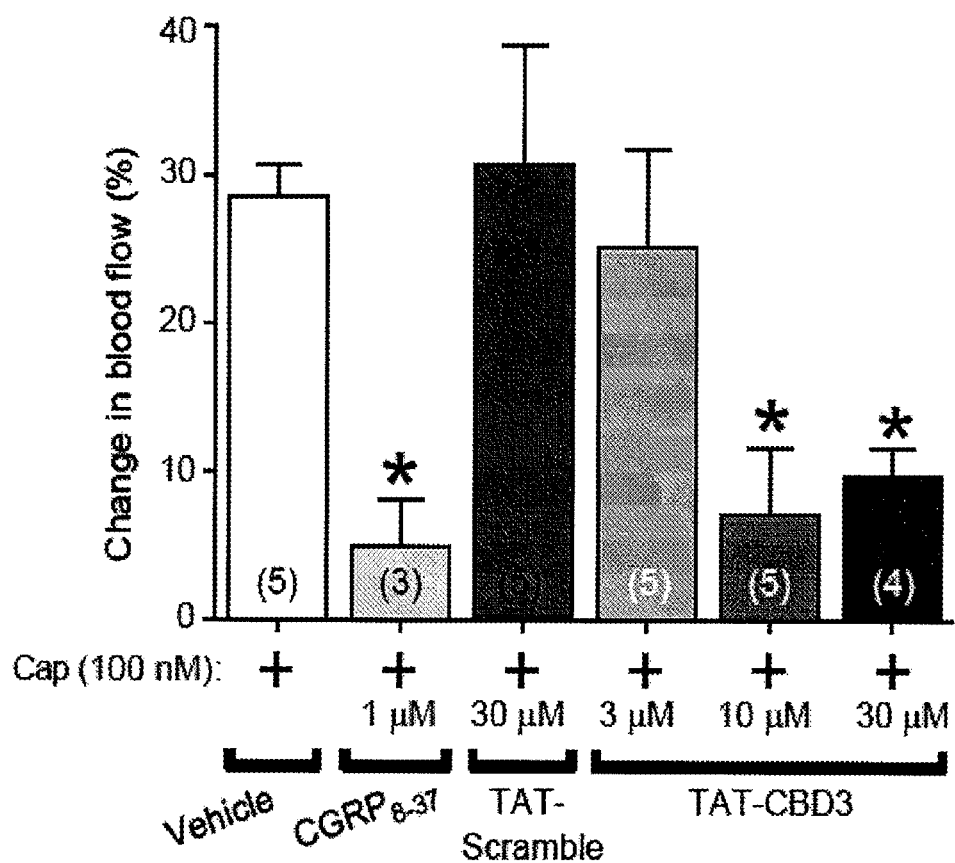
FIG. 15C. Bar graph showing change in meningeal blood flow measured under different conditions.
Figure 15D:
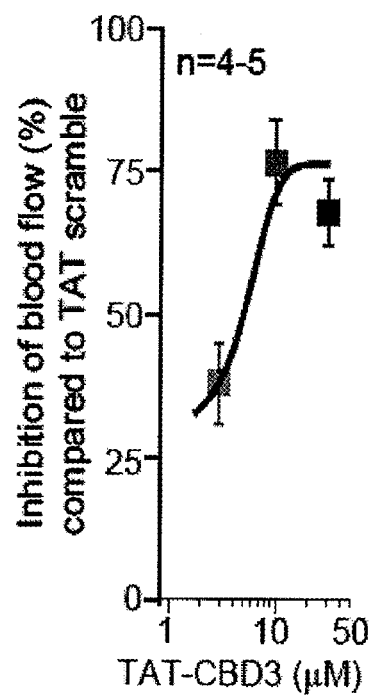
FIG. 15D. Graph showing blood flow inhibition as a function of TAT-CBD3 concentration.

The dura mater is innervated by trigeminal, capsaicin-sensitive sensory neurons which mediate meningeal vascular responses related to headache pain. Since CGRP release from sensory nerve endings causes vasodilation, the potential involvement of CRMP-2 using in vivo laser Doppler blood flowmetry to assay capsaicin-induced blood flow changes was tested (FIG. 15A). Capsaicin induces CGRP-dependent meningeal blood vessel dilatation (FIGS. 15B and 15C) which returns toward baseline values within minutes. Dural application of TAT-CBD3 prior to nasally administered capsaicin inhibited capsaicin-induced blood flow changes in a dose-dependent manner (FIGS. 15C and 15D). TAT-CBD3 administration alone did not alter basal blood flow: changes in blood flow were −6±1, n=5 (vehicle), −9±3, n=5 (TAT-Scramble), and −4±3, n=4 (TAT-CBD3).

TAT-CBD3 Reduces Formalin-Induced Nocifensive Behavior

Referring now to FIG. 16. TAT-CBD3 reduces acute, inflammatory and neuropathic pain. (FIG. 16A) Time course of number of flinches following subcutaneous (dorsal surface of paw) injection of formalin (2.5%; 50 µl saline) in animals pretreated with peptides (3-100 µM; 20 µl dorsal surface of paw) 30 min before formalin (n=4-10). (FIG. 16B) The effect of peptides on number of flinches on formalin-induced phase 1 (0-10 min) and phase 2 (15-60 min). *, p<0.05 versus formalin-injected animals. (FIG. 16C) Formalin induces paw edema. Paw thickness was measured 1 h after injection of saline, formalin, and formalin+peptides (100 µM). *, p<0.05 versus saline-injected animals. (FIG. 16D) Pretreatment with TAT-CBD3 attenuates capsaicin-evoked nocifensive behavior. Vehicle (0.3% DMSO) or peptides (concentrations as indicated) in saline (40 µL) was instilled corneally and nocifensive behavior noted. Five minutes later, capsaicin (Cap; 3 µM, 40 µL saline) was applied corneally and nocifensive behavior noted. *, p<0.05 versus 30 or 100 µM TAT-scramble or 3 µM TAT-CBD3, #, p<0.05 versus all conditions except 3 µM TAT-CBD3 (ANOVA with Dunnett's post-hoc test). (FIG. 16E) Animals injected once with ddC exhibited a decrease in PWT (millinewtons; mN) that was dose-dependently reduced by TAT-CBD3 on post-injection day 7 (PID7). *, p<0.05 versus ddC or TAT-Scramble (ANOVA with Student-Newman-Keuls post-hoc test). (FIGS. 16F-I) DRGs, isolated 15 min after injection of FITC-TAT-CBD3, were labeled with anti-NeuN antibody. TAT-CBD3 (FIG. 16F, FITC; green) accumulates in most neurons (FIG. 16G, NeuN; red). Hoechst (FIG. 16H, blue) indicates nuclear stain. Merged image (FIG. 16I) Scale bars, 100 µm (FIGS. 16F-I). All data reflect mean±SEM.

Figure 16A:
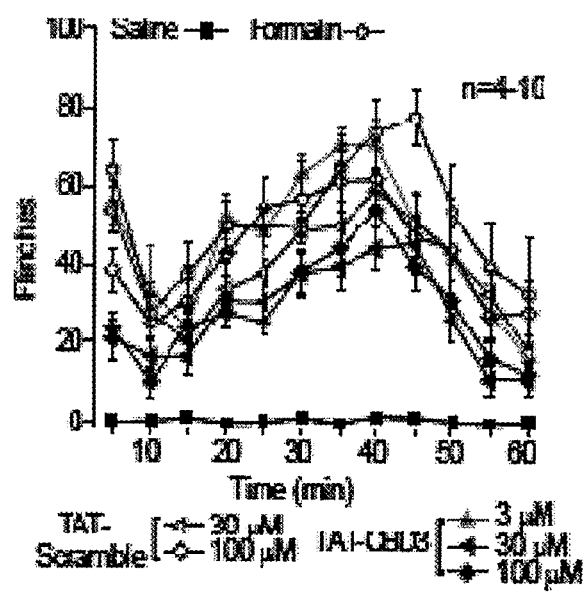
FIG. 16A. Graph of flinches measured over time upon exposure to either TAT Scramble or TAT-CGD3.
Figure 16B:
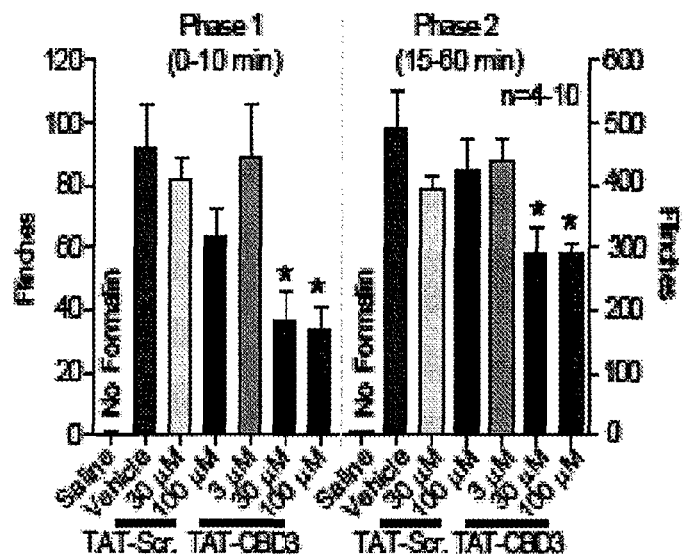
FIG. 16B. Bar graph of number of flinches measured in 2 phases upon exposure to either TAT Scramble of TAT-CBD3.
Figure 16C:
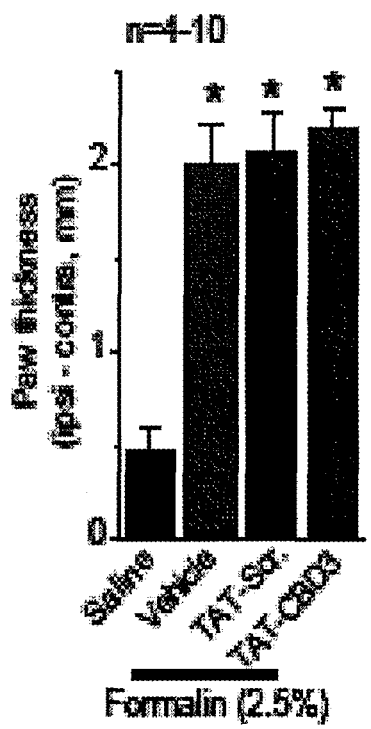
FIG. 16C. Bar graph of paw edema measured after exposure to different reagents: saline, vehicle, TAT-Scramble or TAT-CBD3.

Since inhibiting CaV2.2 is antinociceptive, the ability of TAT-CBD3 to attenuate nociceptive responses in animal pain models was examined. First effects of peptides on formalin-induced nocifensive behavior was examined. In rats administered a subcutaneous injection (to dorsal surface of hindpaw) of vehicle (20 µl 0.5% DMSO) 30 minutes prior to injection of formalin (2.5% in 50 µl), an expected biphasic formalin response (FIG. 16A). Immediately after formalin injection, animals displayed a high degree of flinching (phase 1) lasting ~10 minutes followed by a second period of flinching (phase 2) which subsided by 60 minutes. Pretreatment with 30 or 100 µM TAT-Scramble did not change either phase of the formalin test. In contrast, animals pretreated with 30 or 100 µM TAT-CBD3 displayed blunted nociceptive behaviors in both phases (FIGS. 16A and 16B), suggesting that TAT-CBD3 inhibits nociception mediated by direct activation of sensory neurons (phase 1) and, to some extent, nociception associated with inflammation and spinal involvement (phase 2). Pretreatment with 3 µM TAT-CBD3 did not affect the formalin-induced behavior (FIGS. 16A and 16B). Injection of peptides alone, before the formalin injection, did not induce any nocifensive behavior. Formalin (2.5%) produced a 4-fold change in paw thickness (ipsilateral minus contralateral) compared to saline (FIG. 16C), consistent with edema typically observed following inflammation. TAT-CBD3 did not inhibit formalin-induced edema.

TAT-CBD3 Attenuates Capsaicin-Evoked Nocifensive Behavior

Figure 16D:
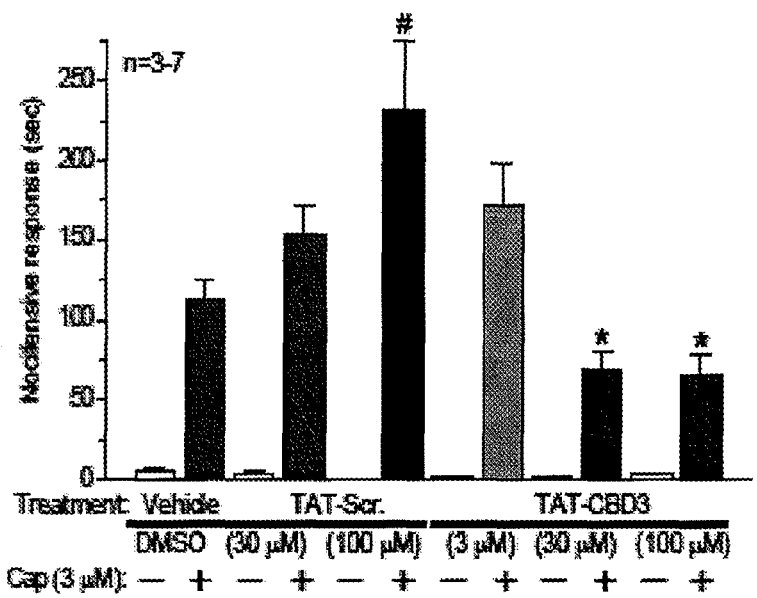
FIG. 16D. Bar graph nocifensive events measured after exposure to different reagents: vehicle, TAT-Scramble or TAT-CBD3.

To determine whether TAT-CBD3 has inhibitory effects on capsaicin-induced nociception, the capsaicin eye-wipe test was utilized. The cornea is innervated by trigeminal afferent nerves, of which ~25% express TRPV1. Application of TAT-CBD3 alone to the cornea did not induce nocifensive behavior. A 30 min pretreatment with 30 or 100 µM TAT-CBD3 attenuated capsaicin-induced nocifensive behavior (FIG. 16D), suggesting that TAT-CBD3 is antinociceptive at a peripheral site of action. Pretreatment with 3 µM TAT-CBD3 did not affect nocifensive behavior; however 100 µM TAT-Scramble showed a non-specific effect, increasing the nocifensive response time (FIG. 16D).

TAT-CBD3 Attenuates ddC-Induced Neuropathic Pain Behavior

Figure 16E:
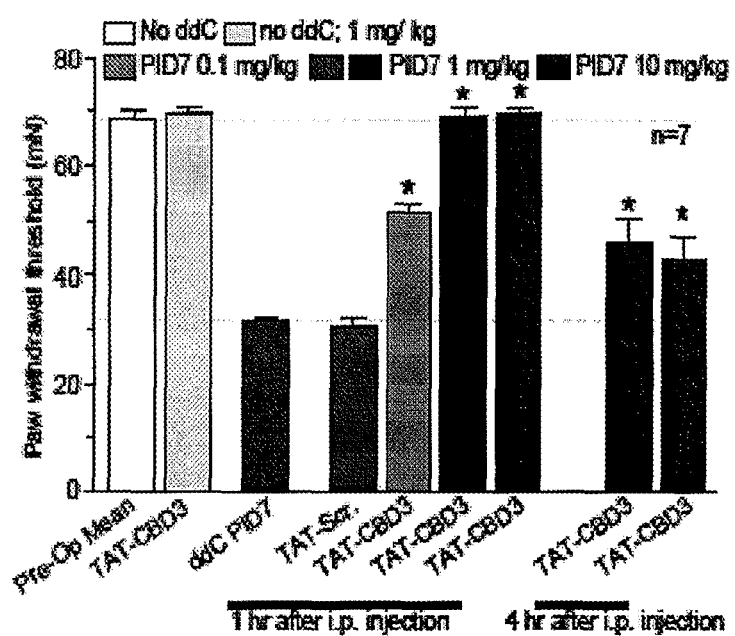
FIG. 16E. Bar graph number of paw withdrawals measured after exposure to different reagents.
Figure 16F:
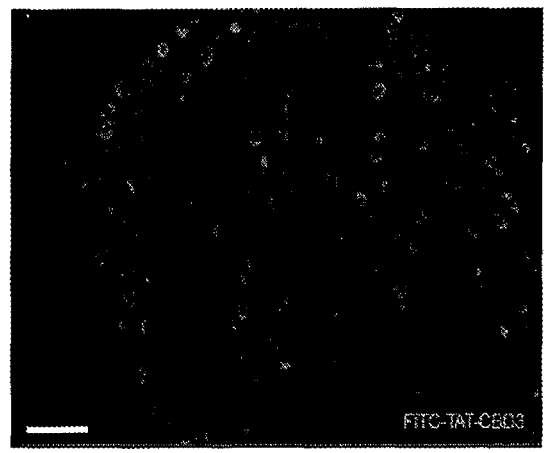
FIG. 16F. Images of DRG cells after injection with FITC-TAT-CBD3 staining with anti NeuN antibody FITC neuron staining.
Figure 16G:
FIG. 16G. Image of DRG cells after contacting them with NeuN.
Figure 16H:
FIG. 16H. Image of DRGs after detecting label associated with cell nucleous.
Figure 16I:
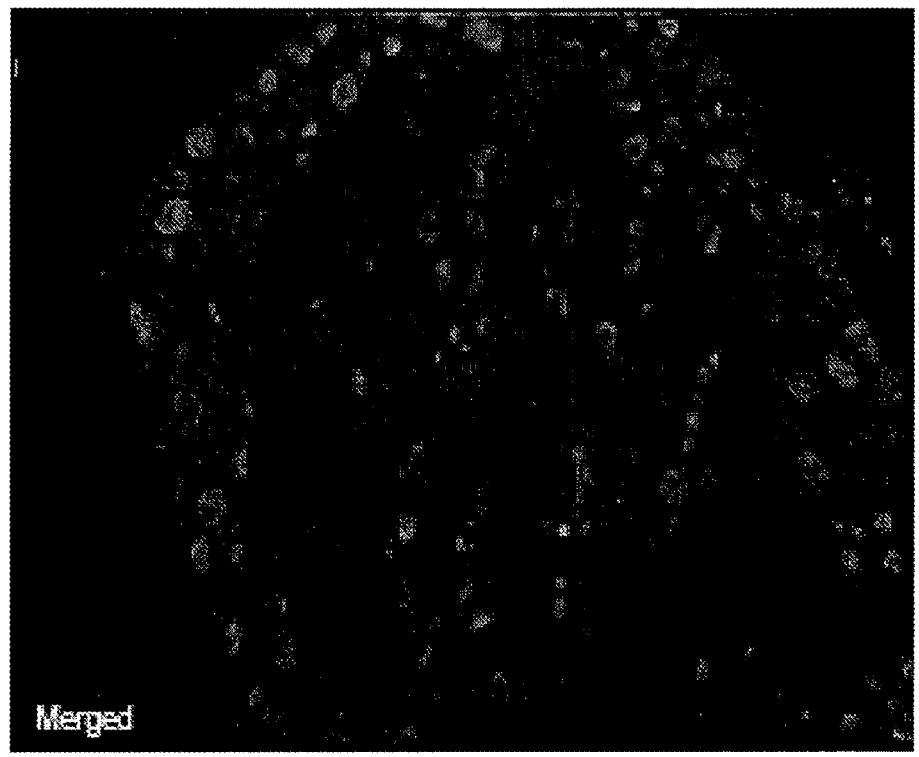
FIG. 16I. Merged image of stained DRG cells.

We next examined the effects of the peptide on chronic nociceptive behavior in an animal model of AIDS therapy-induced painful neuropathy. Nucleoside reverse transcriptase inhibitors (NRTIs), commonly used for AIDS treatment, produce side-effects including painful neuropathies. The ability of peptides to reverse tactile hypersensitivity was evaluated in rats seven days after a single injection of ddC. TAT-CBD3 alone had no effect on paw withdrawal threshold (PWT). TAT-CBD3, but not TAT-Scramble, caused a dose-dependent increase in PWT when administered intraperitoneally (i.p.) (FIG. 16E). Complete reversal of tactile hypersensitivity was observed at the 1 mg/kg dose 1 h after i.p. injection. Four hours after injection, the TAT-CBD3-induced reversal of hypersensitivity had diminished by 50%, which may be accounted for by degradation and biodistribution of the peptide. To explore the distribution of peptides after i.p. injection, tissue samples from animals injected with FITC-TAT-CBD3 were collected.

Referring now to FIG. 24. Biodistribution and side-effects of TAT-CBD3. (FIG. 24A) Dot blot analysis of indicated tissues from rats injected intraperitoneally with 25 mg/kg of TAT-CBD3 peptide. Rats were euthanized at 15 or 60 min post-injection and tissues were frozen under liquid $N_2$. Lysates, 60 µg, of each tissue were bound to a PVDF membrane and immunoblotted with an antibody against the TAT protein, which contains the transduction domain present in the TAT-CBD3 peptide. At 15 min, TAT-CBD3 was detected in spleen and largely concentrated in lumbar dorsal root ganglion (DRG) and lumbar section of the spinal cord. At 1 h, TAT-CBD3 was also detected in kidney, brain, spinal cord and was abundant in the DRG. (FIG. 24.B) Analysis of fluorescein isothiocyanate (FITC) fluorescence of brain, cerebrospinal fluid (CSF) or plasma from rats injected intraperitoneally with 25 mg/kg of FITC-TAT-CBD3. Rats were euthanized at 15 or 60 min post injection and brains were immediately solubilized in cold phosphate buffered saline supplemented with protease inhibitors. Oxygenated blood was collected from a cardiac puncture. The CSF was collected from the subarachnoid space through a 22-gauge needle placed between lumbar vertebral levels L4 and L5. Fluorescence in 50 µl of brains or fluids (in triplicate) was determined using the Victor X3 multilabel plate reader (Perkin Elmer) with a filter to detect fluorescein (excitation/emission=490/530 nm). A standard curve with known amounts of FITC-TAT-CBD3 (20 points) was fitted with a linear regression ($R^2=0.9729$) and demonstrated linearity between ~400 pM and 0.25 µM, with a limit of detection near ~205 µM. The 95% confidence limits are also indicated. (FIG. 24.B) The average fluorescence in brain samples was then normalized to the amount of protein (determined using a BCA assay) and finally plotted as a fold of the normalized fluorescence values observed in tissues from an un-injected animal. Fluorescence levels in CSF and plasma were normalized by volume prior to subsequent normalization to naïve values. At 15 min post-injection, the calculated fluorescence concentration in CSF was about 8.27 µM, which was ~95-fold higher than that in plasma. At 60 min post-injection, CSF levels of FITC fluorescence had dropped by ~85% while those in plasma were ~65% higher compared to the 15 min values. Photographs of a rat before (FIG. 24.D) and after (FIGS. 24.E-G) intraperitoneal injection of 20 mg/kg TAT-CBD3. Representative single images extracted with Windows Live Movie Maker software (Microsoft Inc.) from a high-definition video recording (HTC Evo 4G, Bellevue, Wash.) are shown. To capture side-effects of this high dose of TAT-CBD3, the rat was anesthetized with 4% isoflurane prior to injection of the peptide although similar behaviors were observed in non-anesthetized animals (n=3). (FIG. 24.E) Note the whole-body lordosis-like contortion (black arrow) and tail kinking (white arrow) beginning at about 15 seconds following the i.p. injection. No such contortion or tail movement is evident before the injection (FIG. 24.D). The contortion and tail kinking movements dissipated fifteen seconds following their first appearance (FIG. 24.F). Only a single episode of contortion and tail kinking movement was observed during the 60 min period of observation. (FIG. 24.H) Summary of the percentage of mice that exhibited kinking tail movements in the various conditions (n=7 each). As with the rats, only a single episode of tail kinking movement was observed in the mice. In contrast to the rats, no body contortion was observed in mice even at the 50 mg/kg dose of TAT-CBD3 (n=7).

Following the injection the peptide was detected in DRG (FIGS. 16F-K), spinal cord (see FIGS. 6E-H) (15 min), and brain (FIGS. 24A-C)(1 hr). Transient contortions were observed in animals injected i.p. with 20 mg/kg, but not at lower doses that inhibited hypersensitivity (see FIG. 5E), of TAT-CBD3 (data not shown).

These results illustrate TAT-CBD3, which interferes with CaV2.2 and CRMP-2 interactions, reduces acute inflammatory and neuropathic pain behaviors.

TAT-CBD3 does not Cause Significant Neurobehavioral Deficits.

Referring now to FIG. 17 TAT-CBD3 has no effects on sensorimotor and cognitive functions but has a mild anxiolytic effect. (FIG. 17A) Latency to fall off a slow (left) or fast (right) rotating rod. There were no significant differences in rotarod performances between groups (ANOVA with Dunnett's post-hoc test). (FIG. 17B) Latency for mice to find a hidden platform in the Morris water maze was not different between groups. (FIG. 17C) Time spent in target quadrant. There were no significant differences in percent time spent in target quadrant or path length between groups (Student's t-test). (FIGS. 17D-G) Uptake of FITC-TAT-CBD3 into neurons in ventral horn 15 min following i.p. injection (20 mg/kg). TAT-CBD3 (FIG. 17D, green, FITC) accumulates in motor neurons (arrowheads) which co-label with NeuN (FIG. 17E, red). Nuclei are stained with Hoechst (blue). Merged images demonstrate co-labeling of FITC-TAT-CBD3-containing neurons with NeuN and Hoescht at low (FIG. 17F) and high magnifications (FIG. 17G). Scale bars: 100 µm (FIGS. 17D-F); 40 µm (FIG. 17G).

Figure 17A:
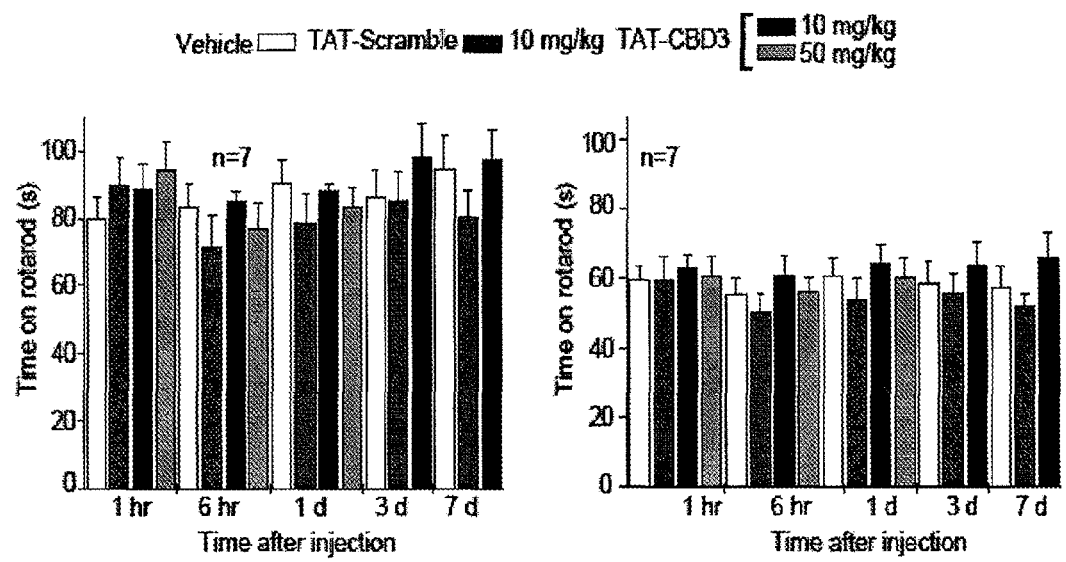
FIG. 17A. Bar graph of time on rotarods as a function of time after treatment with one of the following: vehicle, TAT-Scramble or TAT-CBD3.
Figure 17B:
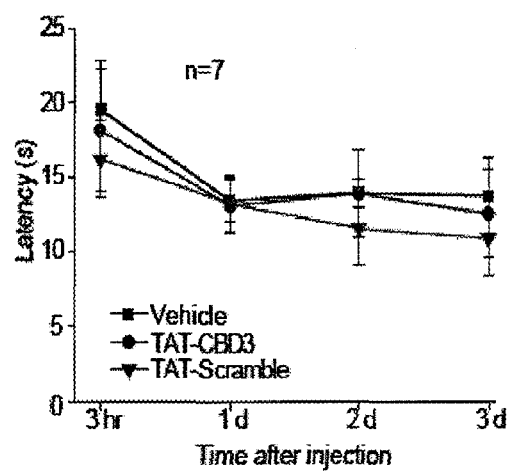
FIG. 17B. Latency measured in water maze versus time after treatment with: vehicle, TAT-Scramble or TAT-CBD3.
Figure 17C:
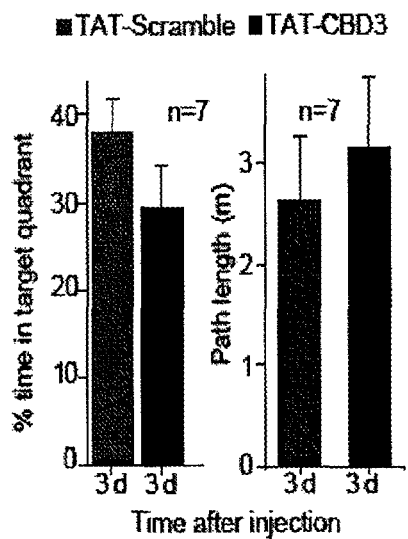
FIG. 17C. Bar graph of the amount of time spent in target quadrant or path length measured in amount treatment with either TAT-Scramble or TAT-CBD3.
Figure 17D:
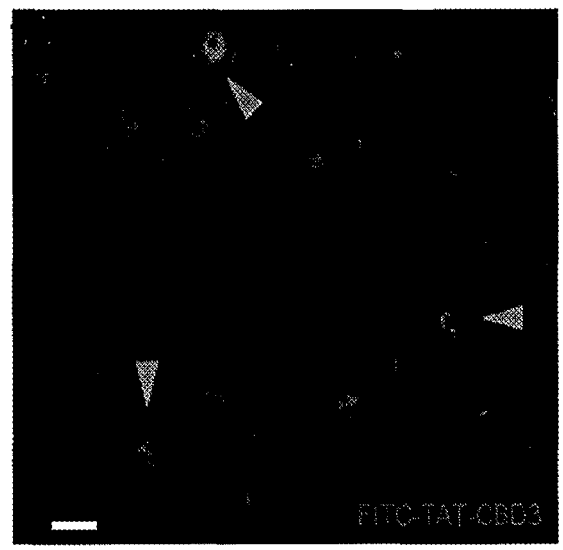
FIG. 17D. Photo micrograph of motor neurons exposed to FITC-TAT-CBD3 stained green with FITC.
Figure 17E:
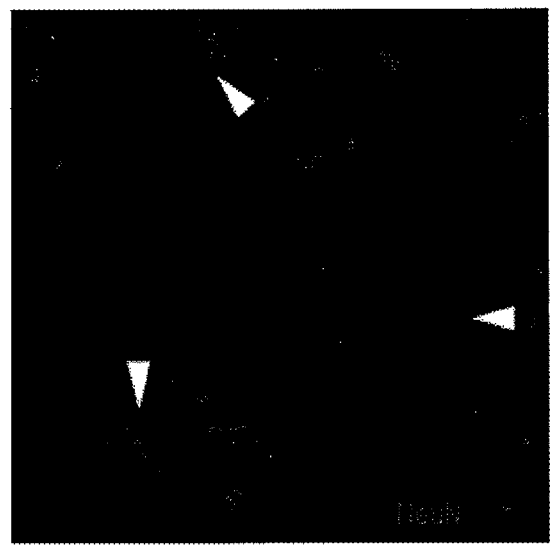
FIG. 17E. Images of neurons labelled with NeuN.
Figure 17F:
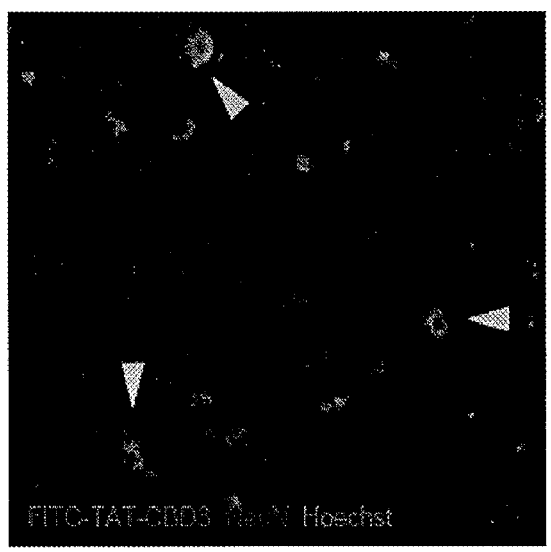
FIG. 17F. Merged image of motors neurons exposed to FITC-TAT-CBD3 showing staining with NeuN Hoescht under low magnification.
Figure 17G:
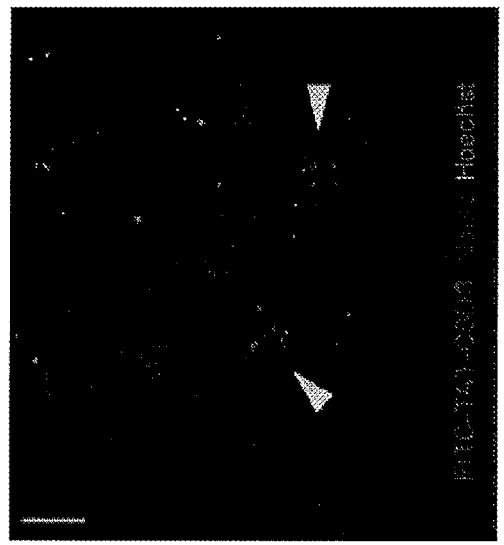
FIG. 17G. Same as FIG. 17E. now visualized under high magnification.
Figure 17H:
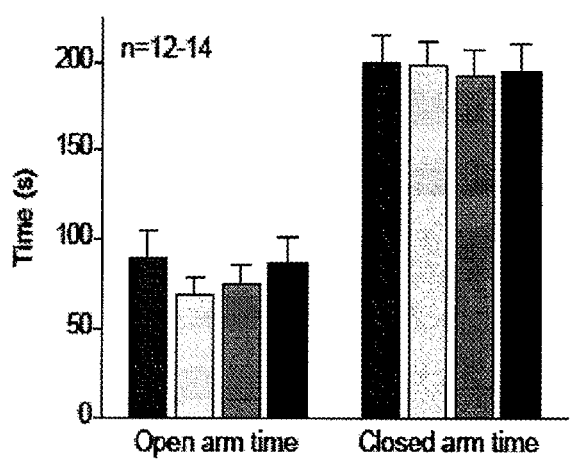
FIG. 17H. Bar graph of time spent in either open or closed arms in elevated maze test.
Figure 17I:
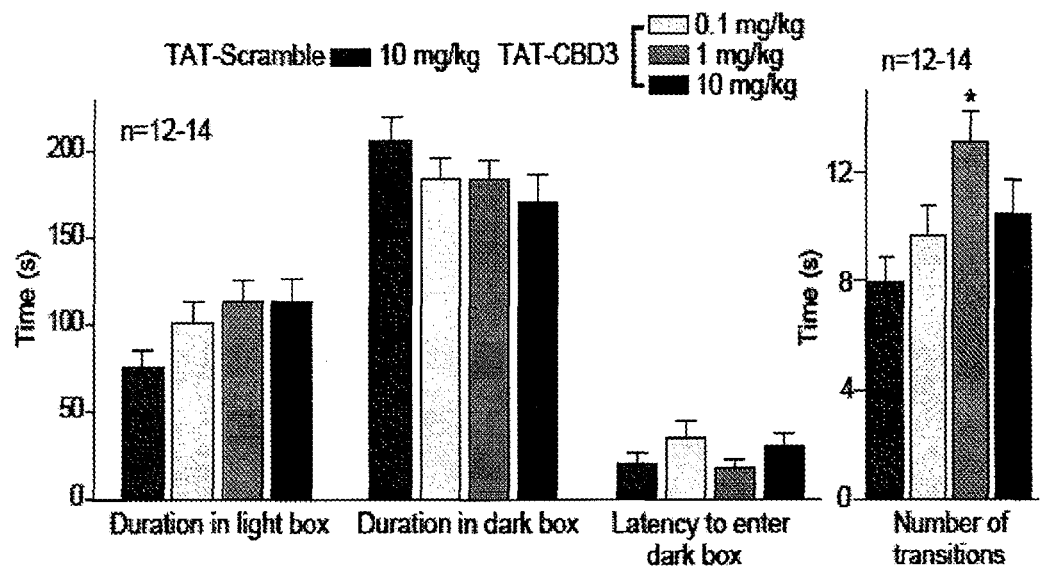
FIG. 17I. Bar graph of time spent in either light or dark box (left panel) number of transitions (center panel), duration of mobility (right panel) with TAT-Scramble or TAT-CBD3.
Figure 17J:
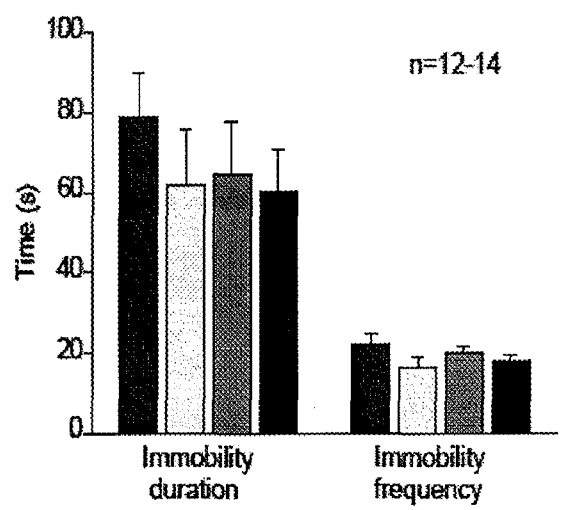
FIG. 17J. Bar graph of duration of immobility (left panel) or frequency of immobility (right panel).

Referring now to FIG. 17H. Elevated plus maze test to evaluate anxiety-associated behaviors. Neither time spent in open or closed arms, nor frequency of entries into closed arms was altered by TAT-CBD3. (i) Light dark box test for anxiety-associated behaviors. TAT-CBD3 did not alter the time spent in the light box or aversion to first entering the dark box. The number of transitions into the light box was increased with 1 mg/kg dose of TAT-CBD3 (*, $p<0.05$, one-way ANOVA). (j) Tail suspension test of depression- or despair-associated behaviors. Duration and frequency of immobility were not altered by TAT-CBD3. All data reflect mean±SEM.

The possible effects of TAT-CBD3 on motor coordination, locomotor function, sedation (rotarod test) and hippocampal-dependent memory (Morris water-maze test) was investigated. Impaired locomotor function did not account for reduced flinching and paw withdrawal as TAT-CBD3 (10 and 50 mg/kg; i.p.) had no effect in the accelerating rotarod test (FIG. 17A). TAT-CBD3 (10 mg/kg; i.p) also did not affect coordination or spatial memory at 1 h-7 d after administration (FIGS. 17B and 17C), suggesting memory retrieval was not affected by TAT-CBD3. A single episode of kinking at the base of the tail and whole body contortion was observed in mice immediately following injection of higher doses (10 and 50 mg/kg) of TAT-CBD3 (FIGS. 24D-G).

As pharmacological block of N-type channels has been linked to anxiety and depression-associated behaviors, TAT-CDB3 was tested to determine if it could alter these behaviors. Elevated plus maze (EPM) and Light-Dark Box test (LDBT) were used in these test. These paradigms assess the conflict against hiding in enclosed dark areas (i.e., dark box or closed arm) and exploring novel environments (i.e., white box or open arm). In the EPM test, neither time spent in the open or closed arms, nor frequency of entries into the open nor closed arms were altered by any dose of TAT-CBD3, compared to the TAT-Scramble (Table 1). In LDBT, although time spent in the white and dark boxes was not different between any of the conditions, the number of transitions between the light and dark box was increased in mice injected with 1 mg/kg TAT-CBD3, compared to TAT-Scramble (data not shown). These results suggest that TAT-CBD3 does not appear to affect anxiety-associated behaviors apart from increasing transitions in LDBT, supporting slightly anxiolytic properties.

Since rodents display immobile postures when placed in inescapable, stressful situations, immobility behavior in the tail suspension test (TST) or forced swim test (FST) is used as a measure of "depression" or "despair-associated" behavior, which is attenuated by antidepressant treatments. In the TST, neither time spent immobile, nor frequencies of immobile episodes were altered by any dose of TAT-CBD3, compared to TAT-Scramble Table 1. Overall, no dose of TAT-CBD3 altered depression/despair-associated behavior.

TABLE 1

Anxiety-like and despair behaviors

| Behavioral Test | TAT-Scramble 10 mg/kg | TAT-CBD3 0.1 mg/kg | TAT-CBD3 1 mg/kg | TAT-CBD3 10 mg/kg |
| --- | --- | --- | --- | --- |
| Elevated Plus Maze (n) | (13) | (13) | (12) | (14) |
| Open arm entries | 11.5 ± 1.6 | 13.6 ± 1.6 | 19.7 ± 3.1 | 20.0 ± 6.1 |
| Open arm latency to enter (s) | 5.9 ± 2.3 | 10.3 ± 2.7 | 10.1 ± 2.9 | 4.6 ± 1.9 |
| Open arm latency to exit (s) | 14.5 ± 3.1 | 17.7 ± 2.5 | 16.4 ± 3.1 | 11.1 ± 2.1 |
| Closed arm entries | 16.3 ± 2.0 | 19.1 ± 1.4 | 26.4 ± 4.2 | 27.4 ± 7.0 |
| Closed arm latency to enter (s) | 6.3 ± 2.5 | 4.5 ± 2.2 | 2.4 ± 2.1 | 5.3 ± 2.2 |
| Closed arm latency to exit (s) | 14.7 ± 3.0 | 14.9 ± 2.9 | 11.1 ± 2.6 | 10.6 ± 3.5 |
| Light-Dark Box (n) | (13) | (13) | (12) | (13) |
| Light box entries | 8.2 ± 0.8 | 10.6 ± 1.2 | 13.5 ± 1.1 | 11.5 ± 1.2 |
| Dark box latency to exit (s) | 53.0 ± 11.5 | 66.0 ± 17.3 | 36.9 ± 5.8 | 49.5 ± 9.6 |
| Tail Suspension Test (n) | (13) | (10) | (11) | (12) |
| Active (s) | 221.0 ± 11.3 | 238.1 ± 13.6 | 235.2 ± 13.0 | 239.7 ± 10.9 |

Behavioral tests were performed on 6-week old C57BL6 mice 1 h after i.p. injection of TAT peptides, with each test lasting 5 minutes. Values represent the average ± SEM for each treatment group. Numbers of animals are indicated in parentheses.

These findings demonstrate that administration of TAT-conjugated CBD3 peptide interferes with CaV2.2 trafficking to the presynaptic membrane and that the physiological consequences of TAT-CBD3 peptide treatment include inhibition of calcium currents, stimulus-evoked neuropeptide release from sensory neurons, and excitatory synaptic transmission in dorsal horn neurons. TAT-CBD3, which disrupts CRMP-2 regulation of CaV2.2 function, achieves a therapeutic window suitable for a number of pain states, both inflammatory and neuropathic, with no impairment of motor function or higher order processes. The precise mechanism by which TAT-CBD3 affects pain signaling appears to be regulation of CaV2.2.

In order to block interactions between CRMP-2 and the N-type calcium channel, a CaV2.2-binding peptide, CBD3, which is highly conserved between rodents and humans, and contains little or no sequence homology with other proteins was designed. The peptide was conjugated to the HIV-1 TAT domain to overcome the obstacle of poor plasma membrane penetrance of peptides.

Pharmacologic block of CaV2.2 not only reduces presynaptic neurotransmitter release but may also decrease the excitability of the post-synaptic neurons within lamina I of the spinal cord. A tangible mechanism for decreased sEPSC frequency in the post-synaptic, spinal cord lamina II neurons following treatment with TAT-CBD3 may be due to both inhibition of neurotransmitter release (i.e. glutamate) from sensory neurons and diminished vesicular recycling.

CaV2.2 has been implicated in playing a critical role in instigating the increased excitability and neurotransmitter release associated with chronic and neuropathic pain conditions. Genetic and pharmacological block of CaV2.2 following injury in rodents attenuates nociceptive behavior. Moreover, expression of CaV2.2 is upregulated in several animal models of neuropathic pain. Cizkova, D. et al. Localization of N-type Ca2+ channels in the rat spinal cord following chronic constrictive nerve injury. *Exp. Brain Res.* 147, 456-463 (2002). Inhibition of CaV2.2 is also one mechanism underlying morphine-induced analgesia. A pro-nociceptive role for CaV2.2 is further highlighted by the identification of alternative splice variants of CaV2.2 expressed on small-diameter nociceptive neurons which contribute to thermal and mechanical hyperalgesia.

To determine the effects of TAT-CBD3 peptide on nociception, a variety of animal pain models encompassing acute and inflammatory/chronic nociception states was used. Behavioral outcomes from the capsaicin eye-wipe test, suggested that the peptide inhibits acute nociception. As disclosed herein, it was also observed that administration of TAT-CBD3 into the dorsal surface of the paw significantly reduced the number of flinches in phase 1 and phase 2 of the formalin test. A greater effect of TAT-CBD3 in phase 1 of the formalin test compared to phase 2 was also observed, a difference which at first may suggest a more pronounced involvement of CaV2.2 in primary nociception than in the perception of inflammatory pain. Phase 1 of the formalin test results from direct stimulation of nociceptors, whereas phase 2 involves a period of central sensitization during which inflammatory phenomena occur. Le, B. D., Gozariu, M., & Cadden, S. W. Animal models of nociception. *Pharmacol. Rev.* 53, 597-652 (2001). Therefore, because the peptide was injected in the periphery, the effect observed in phase 1 suggests that either TAT-CBD3 affects transmission of the nociceptive signal or inhibits release of CGRP or other neuropeptides at the peripheral end of the nociceptors. The observation that the effects of TAT-CBD3 were antinociceptive in acute studies is consistent with activity-dependent regulation demonstrated for the CRMP-2–CaV2.2 interaction, suggesting a decrease in presynaptic neuronal excitability.

Since results in other models clearly show an inhibition in CGRP release, this could explain the effect of TAT-CBD3 peptide in the phase 1 of the formalin test. If TAT-CBD3 indeed inhibits the peripheral release of CGRP, then one would expect a reduction in edema. However, TAT-CBD3 peptide did not inhibit formalin-induced edema. While the complexity of the peripheral inflammatory process and its relationship to nociception are not completely understood, edema occurs in response to several inflammatory mediators that could be released by cells other than neurons. Therefore, inhibiting release of only CGRP is likely insufficient in reducing edema. The differential effect of TAT-CBD3 in nociceptive behavior and edema suggest a lack of common mechanisms between these two inflammatory components. In support of this assertion, a 5-hydroxytryptamine receptor antagonist was found to inhibit 2.5% formalin-induced nociceptive behavior, but not edema. Doak, G. J. & Sawynok, J. Formalin-induced nociceptive behavior and edema: involvement of multiple peripheral 5-hydroxytryptamine receptor subtypes. *Neuroscience.* 80, 939-949 (1997). Moreover, morphine when administered peripherally inhibited carrageenan-induced hyperalgesia without inhibiting edema, while when injected systemically morphine reduced edema, plasma extravasation and inflammatory hyperalgesia. Thus, although TAT-CBD3 peptide did not inhibited formalin-induced edema, the effect on neurotransmitter release cannot be ruled out as a mechanism of the peripheral antinociceptive effect observed in pain models.

Additionally, these findings illustrate that TAT-CBD3 suppresses tactile hypersensitivity in an animal model of HIV-treatment-induced peripheral neuropathy, a chronic model of neuropathic pain. This model employs the anti-retroviral treatment 2',3' dideoxycitidine (ddC) to induce the small fiber dying back neuropathy that is seen in post-treatment AIDS patients, which has been attributed to reduced calcium buffering. Systemic TAT-CBD3 administration reverses ddC-induced nociceptive behaviors, suggesting a continued role for the interaction of CRMP-2 and CaV2.2 on neurotransmitter release. Consistent with this hypothesis, others have shown that CaV2.2 mediates an enhanced release of neurotransmitters in the spinal cord important for the maintenance of inflammatory pain.

Despite the promising potential of pharmacological inhibitors of N-type channels, in the treatment of intractable or chronic pain conditions, they are overshadowed by a narrow therapeutic window. Intrathecal delivery of Prialt in animal and clinical studies results in a multitude of deleterious side-effects including impaired learning and memory, motor coordination, and increased anxiety/depression. Snutch, T. P. Targeting chronic and neuropathic pain: the N-type calcium channel comes of age. NeuroRx. 2, 662-670 (2005). At doses more than 50-fold higher than that required to reduce hypersensitivity in vivo, TAT-CBD3 exerted mild motor impairment (transient tail kinking and body contortion) but had no effect on motor coordination, memory retreival, or anxiety and depression-associated behaviors in these animals. Remarkably, TAT-CBD3 had a mild anxiolytic effect consistent with that observed in animals lacking CaV2.2. The relative lack of toxicity observed with systemic delivery of TAT-CBD3 provides promising evidence of its therapeutic potential.

These findings illustrate that TAT-CBD3 allows suppression of pain hypersensitivity without directly blocking CaV2.2, but rather by inhibiting the binding of a regulator of CaV2.2 function, CRMP-2. These findings also represent a novel approach potentially useful in managing clinical pain.

Therapeutic doses of the compounds disclosed herein can be determined by routine adjustments of the desired levels of the active compounds in a variety of formulation. the exact mounds will vary from patient to patient dependent in part of factors such as the weight, age, gender, health, genetics of the patient and other therapeutic compounds that a given patient may also be using when the inventive compounds are administered.

Levels of the compound such as TAT-CBD3 on are effective over the range of about 1 mg to about 100 mg of active ingredient per kg of patient body weight. Although other amounts are within the scope of the claimed invention.

EXPERIMENTS

Materials and Methods

Animals. Procedures involving animals and their care were in accordance with the Guide for the Care and Use of Laboratory Animals (National Institutes of Health publication 85-23, Bethesda, Md., USA) and approved by the Institutional Animal Care and Use Committee of the Indiana University School of Medicine. CD1 mice (3-6 months in age) and Sprague-Dawley rats (100-150 grams in size) were purchased from Harlan Laboratories (Indianapolis, Ind.) and housed in the Indiana University Laboratory Animal Research Center (LARC). The animals were housed in cages in a light-controlled room at 22° C. Food and water were available ad libitum.

Isolation and maintenance of primary hippocampal neurons for electrophysiology. Rat hippocampal neuron cultures were prepared from hippocampi dissected from postnatal day 1 (PN1) rats exactly as described previously. Cells were grown in media consisting of Neurobasal medium containing 2% NuSerum, 5% NS21, supplemented with penicillin/streptomycin (100 U/ml; 50 µg/ml), 0.1 mM L-Glutamine and 0.4 mM L-glutamax (Invitrogen). Cytosine β-D-arabinofuranoside (5 µM; Sigma) was added 24 h after plating to reduce the number of non-neuronal cells. After 4 d in culture and 2× each week thereafter, half of the growth medium was replaced with medium without cytosine β-D-arabinofuranoside.

Isolation and maintenance of primary hippocampal neurons for calcium imaging. A primary culture of hippocampal neurons was prepared from PN1 rat pups according to IACUC approved protocols and previously published procedures. For fluorescence measurements, neurons were plated on glass-bottomed Petri dishes without preplated glia as previously described. A solution of 35 µg/ml uridine plus 15 µg/ml 5-fluoro-2'-deoxyuridine was added 24 hours after plating to inhibit proliferation of non-neuronal cells. Cultures were maintained in a 5% $CO_2$/air atmosphere at 37° C. in MEM supplemented with 10% NuSerum (BD Bioscience, Bedford, Mass.) and 27 mM glucose.

Isolation/maintenance of sensory neurons for iCGRP release. Sensory neurons were isolated from adult rodents using procedures developed by us previously. Male Sprague-Dawley rats were killed in a chamber filled with $CO_2$. The isolated spinal column was hemisected, the spinal cord was removed, and the DRG were collected in sterilized Puck's solution ($Ca^{2+}$-, $Mg^{2+}$-free Hank's balanced salt solution).

For rat DRG, the ganglia were transferred into F-12 media containing 1 mg/ml collagenase IA and 2.5 mg/ml dispase and incubated for 30 min at 37° C. Cells were digested in DNAse for one minute at room temperature followed by centrifugation to remove the enzyme-containing supernatant. The pellet was resuspended in F-12 media supplemented with NGF (30 ng/ml; Harlan) and mechanically dissociated with fire-polished pipettes.

Isolated rat cells (~1.5×10$^5$ cells/ml) were plated on coverslips coated with poly-D-lysine and laminin. Rat DRG cultures were maintained at 37° C. and 3% $CO_2$ in F-12 media supplemented with NGF (30 ng/ml). Isolated mouse neurons were plated in coated wells of 24-well dishes at a density of 3–5×10$^4$ cells/well. Cultures were maintained at 37° C. in a 5% $CO_2$ atmosphere in supplemented F12 media.

Isolation and maintenance of sensory neurons for electrophysiology. DRG from young adult rat (~150 g) were dissociated and cultured as described previously. In brief, DRG isolated from lumber segments of spinal cords of young adult rats were dissociated by a combination treatment with a dispase/collagenase cocktail and mechanical disruption through a series of fire-polished glass pipettes with a decreasing inner tip diameter. The resulting suspension of single cells was plated on poly-D-lysine-coated coverslips and maintained in Dulbecco's modified Eagle's medium (DMEM) (Gibco, Invitrogen, Grand Island, N.Y., USA) supplemented with 10% fetal bovine serum (FBS) (Hyclone, Logan, Utah, USA) and 100 units/ml penicillin and 100 µg/ml streptomycin for 12-16 hours at 37° C. under 5% $CO_2$.

Catecholamine A Differentiated (CAD) cells. CAD cells were grown at 37° C. and in 5% $CO_2$ (Sarstedt, Newton, N.C.) in Ham's F12/EMEM medium (GIBCO, Grand Island, N.Y.), supplemented with 8% fetal bovine serum (FBS; Sigma, St. Louis, Mo.) and 1% penicillin/streptomycin (100% stocks, 10,000 U/ml penicillin G sodium and 10,000 µg/ml streptomycin sulfate). Cells were passaged every 6-7 days at a 1:25 dilution.

Transient transfection. Adherent cultures were transfected with cDNAs using Lipofectamine 2000 (Invitrogen) as described previously. About 2-3% transfection efficiencies in hippocampal neurons was achieved routinely, 35-40% in DRG, and 75-80% in CAD cells transfected with this method. Typically, cultured cells were transfected with equal amounts of different cDNA constructs and experiments performed two days later.

Brain lysate and synaptosome isolation. Synaptosomes (i.e., enriched nerve endings) were prepared as described from PN1 or adult Sprague Dawley rats (Harlan Labs., Indianapolis, Ind.). Samples were lysed in modified RIPA buffer (50 mM Tris-HCl, pH8, 1% nonidet P-40 (NP-40/Igepal), 150 mM NaCl, 0.5% Na deoxycholate, and 1 mM EDTA, and supplemented with freshly added protease inhibitors: 1 µg/ml leupeptin, 2 µg/ml aprotinin, 1 mM PMSF (Sigma) together with a protease inhibitor cocktail (Roche Applied Science, Laval, Quebec)).

Purification/Enrichment of $Ca^{2+}$ channels from synaptosomes. In order to prepare a rich source of CaV2.2 for the far-Western analyses (see below), synaptosomes from P1 neonatal rat brains were solubilized with digitonin and enriched by chromatography on WGA-Sepharose as described previously. Briefly, 30 PN1 neonatal rat brains were homogenized in 180 ml of 320 mM sucrose with a glass-Teflon homogenizer. After a short centrifugation (5000 rpm, 2 min), the supernatant (SN) was centrifuged (42,000 rpm, 60 min). The membranes were solubilized with 1.2% digitonin, 80 mM sodium phosphate buffer, pH 7.4 for 20 min. Unsolubilized material was removed by the centrifugation as before, and the supernatant (S3) was poured over a 40 ml WGA-Sepharose column (50 ml/h). After incubation for 1 hr at 4° C., the column was washed with 10 column volumes of 0.1% digitonin, 75 mM NaCl, 50 mM sodium phosphate, 10 mM Tris-HCl (pH 7.4) at a flow rate of 50 ml/hr. The glycoproteins bound to the WGA-Sepharose column were eluted with 100 mM N-acetyl-D-glucosamine (Sigma, St. Louis, Mo.) in the same buffer at a flow rate of 50 ml/hr. Three milliliter fractions were collected and the protein concentration of each fraction was determined by BCA protein assay kit (Thermo Fisher Scientific, Shelbyville, Ind.).

To further enrich for $Ca^{2+}$ channels, WGA-column fractions were incubated for 4 hr on ice with 200 µl of heparin-agarose. The resin was washed four times with 0.2% CHAPS, 10 mM Tris-HCl, pH 7.4, and once with 10 mM Tris-HCl, pH 7.4. $Ca^{2+}$ channels were gently extracted for 30 min at 50° C. with 100 µl of 5% SDS, 20 mM dithiothreitol, 125 mM Tris-HCl, pH 6.8, 10% sucrose, 20 mM EDTA.

Peptide spots arrays and Far Westerns. Peptide arrays (10-15 mers) spanning the entire length of rat CRMP-2 were constructed using the SPOTS-synthesis method. Standard 9-fluorenylmethoxy carbonyl (Fmoc) chemistry was used to synthesis the peptides on cellulose membranes prederivatized with a polyethylene glycerol spacer (Intavis AG, Cologne, Germany). Fmoc protected and activated amino acids (Intavis) were spotted in 20-30 arrays on 150 mm by 100 mm membranes using the Intavis MultiPep robot. Membranes were probed in a far-Western manner with an antibody against CaV2.2 (Calbiochem Inc, La Jolla, Calif.). Briefly, Peptides (10-15-mers) were immobilized to nitrocellulose membrane which was then soaked in CAPS buffer (10 mM CAPS pH 11.0 and 20% methanol) for 30 min, washed once with TBST, and then blocked for 1 h at RT with gentle shaking in TBST containing 5% non-fat milk and finally incubated with a purified synaptosome fraction enriched in $Ca^{2+}$ channels for 1 h at RT with gentle shaking. Next, the membrane was incubated in primary antibody for CRMP-2 for 2 h at RT with gentle shaking, followed by washing with TBST. Finally, the membrane will be incubated in secondary antibody (horseradish peroxidase-conjugated goat anti-rabbit; 1:10,000) for 45 min, washed for 30 min in TBST and developed using enhanced chemiluminescence.

In Vitro Protein Binding Assays. Using Vector NTI (v. 11; Invitrogen) software, primers were designed to amplify regions corresponding to the first cytoslic loop (L1; amino acids 356 to 483) and the distal end of the C-terminus (Ct-dis; amino acids 2133 to 2348) of rat CaV2.2 cDNA from P3 rat brain cDNA. The primers harbored restriction sites (Bam HI or Bgl II (5') and Eco RI or Mfe I (3')) to facilitate cloning into the. In addition to the GST-tag, this vector contains the Glu tag, a sequence of six amino acids (EYMPME). Correctly-amplified PCR products and parent pGex-3x-Glu vector were digested with the indicated restriction enzymes, and then extracted following electrophoresis on an agarose gel. The extracted DNAs were quantified (Nanodrop 1000, Thermo Scientific), and ligations were performed using 6:1 and 3:1 insert to vector molar ratios. The ligations were transformed into XL-10 *E. Coli* and colonies were screened using colony PCR. Those colonies with the correct-sized inserts were further verified by dideoxy sequencing (Cogenics, Houston, Pa.). GST-Glu tagged versions of intracellular loops of CaV2.2 were purified as previously described[5] except that the proteins were dialyzed into a buffer containing 10 mM HEPES pH 7.4, 100 mM NaCl, and 10 mM $CaCl_2$ prior to binding experiments.

Monoclonal Glu antibody-saturated Protein G beads (GE Healthcare) carrying various CaV2.2 cytoplasmic loop constructs were incubated with rat brain synaptosome protein in the presence of TAT control or TAT CBD3 peptides (10 µM) in a total reaction volume of 400 µl. Reactions were incubated end-over-end overnight at 4° C. and then incubated with Glutathione cellulose for 2 h at 4° C. The samples were then washed three times with a 1000-fold excess of binding buffer, and the proteins were eluted in 40 µl of SDS gel buffer and boiled for 5 min, after which 20 µl of each assay was run on SDS-PAGE and analyzed by immunoblotting with CRMP-2.

Immunoblotting. This was performed as described previously. Rat brain synaptosomes were pre-cleared by a 1-h incubation with 20 µl of a 50% slurry of protein A/G beads (Pierce). The cleared lysate was then incubated overnight with various primary antibodies or rabbit or mouse isotype-specific IgGs (Sigma) as controls. The antibody-captured complexes were recovered with fresh protein A-agarose (for rabbit polyclonal antibodies) or protein A/G-agarose (for mouse monoclonal antibodies) beads (20 µl of original bead slurry/sample) by incubation with lysate/antibody mixture at 4° C. for 2 h. The beads were then washed three times with lysis buffer. Prior to electrophoresis on SDS-polyacrylamide gels, protein samples were boiled in Laemmli sample buffer for 5 min. Proteins were fractionated on 5, 7.5, 10, or 4-15% separating gels with 4% stacking gels.

Ten µg of protein was separated by SDS-PAGE (4-12% polyacrylamide gradient gel) and electrophoretically transferred onto PVDF membranes (Invitrogen) and assayed for the presence of CRMP-2 (Chemicon Int., Billerica, Mass.) and CaV2.2 proteins using specific antibodies. The membranes were blocked for 1 h in 5% skim milk powder in TBST (25 mM Tris-Cl, pH 8.0, 125 mM NaCl, 0.1% to 2% polyoxyethylene sorbitan monolaurate (Tween-20)) at room temperature. Primary antibody incubations were for 2 h at RT or overnight at 4° C. Following incubations with primary antibody and secondary antibody (goat anti-rabbit or anti-mouse IgG horseradish peroxidase (1:10000; Stressgen, Ann Arbor, Mich.)), blots were washed extensively in TBST and probed with Enhanced Chemiluminescence Western blotting substrate (Thermo Scientific) before exposure to photographic film. Blots were exposed for a range of durations to ensure the generation of a print in which the film is not saturated. Films were then scanned, digitized and quantified using Un-Scan-It gel V6.1 scanning software (Silk Scientific Inc., Orem), limiting analysis to the linear range.

Cell Surface Biotinylation. Biotinylation was performed as described. CAD cells, transfected with control vector, or plasmids harboring a region encoded by 80 amino acids in the N-terminus of CRMP-2 (CBD1) or the 15 amino acid peptide CBD3, were incubated with sulfosuccinimidyl 2-(biotinamido) ethyl-1,3' dithiopropionate (1 mg/mg protein; Pierce) for 30 min at 4° C. in cold PBS, pH 8.0. Excess biotin was quenched with PBS containing 100 mm glycine and washed three times with ice-cold PBS, and the pellet was resuspended in RIPA lysis buffer. The resuspended pellet was triturated 10 times (25-gauge needle) and centrifuged at 100,000×g for 20 min. The biotinylated proteins were separated from clear solubilizate by adsorption onto streptavidin-agarose beads (Novagen) for 2-4 h at 4° C. Beads were washed 3-5 times with RIPA buffer, and bound biotinylated proteins were gently eluted off of the beads with RIPA buffer containing 2% Triton X-100 and 650 mm NaCl by end-over-end incubation for 1 h at 30° C. The biotinylated fraction was subjected to immunoblotting with the CaV2.2 antibody.

Surface Plasmon resonance (SPR). Binding analyses between TAT CBD3 or TAT control peptides and CaV2.2 L1- or Ct-dis-GST fusion proteins was determined by surface plasmon resonance using a BIAcore3000 instrument (Biacore AB, Uppsala, Sweden). Briefly, binding assays were performed using HBS-EP buffer (0.01 M HEPES, pH 7.4, 0.15 M NaCl, 3 mM EDTA, and 0.005% surfactant P20) as the running buffer. The CaV2.2 L1- and Ct-dis-GST fusion proteins, purified as described previously, were diluted in HBS-EP buffer and injected at a 10 µl/min flow rate over four flow cell surfaces simultaneously using the KINJECT command. Surface regeneration was performed by 10-µl injections of 0.05% SDS in HBS-EP buffer at a 20 µl/min flow rate. Background binding to a negative control peptide surface (control) was subtracted from all binding curves using BIAevaluation software version 3.0 (BIAcore Inc.) and plotted using GraphPad Prism version 4.0 (Graph-Pad Software Inc., San Diego, Calif.).

Fluorescence detection of fluorescein isothiocyanate (FITC) labeled TAT-CBD3. Male Sprague-Dawley rats received an intraperitoneal (i.p.) injection of FITC-TAT-CBD3 (10 mg/kg). Rats were euthanized with $CO_2$ at 15 minutes and 60 minutes post-injection and tissue samples were harvested. Samples of brain, liver, kidney, lumbar dorsal root ganglia, trigeminal ganglia, and lumbar spinal cord were collected immediately following euthanasia and homogenized in phosphate buffered saline supplemented with protease inhibitors. Tissue samples were clarified prior to analysis. Plasma samples were acquired by collecting oxygenated blood via cardiac puncture. Whole blood samples were centrifuged at 2000×g for 10 minutes to allow separation of plasma from white and red blood cell layers. Cerebrospinal fluid (CSF) was collected from the subarachnoid space through a 22-gauge needle inserted between lumbar vertebral levels L4 and L5 as described previously. FITC fluorescence levels in 50 µl of each sample were determined using the Victor X3 multilabel plate reader (Perkin Elmer) with filter parameters to allow detection of fluorescein (excitation/emission=490/535 nm) and compared to a standard curve of FITC-TAT-CBD3.

MTT Cell Viability Assay. DRG neurons were incubated with TAT CBD3 (10 µM) or TAT control (10 µM) overnight (12 h) at 37° C. under 5% $CO_2$. Then, 100 µl MTT [3-(4,5-dimethylthiazol-2-yl)-2,5-diphenyltetrazolium bromide; (5 g/L, Promega)] was added to each well. Following a 2 h incubation, cell viability was assessed according to manufacturer's instructions by measuring absorbance at 490 nm using a Victor³ V multilabel plate reader. Percent absorbance relative to control was determined.

Whole-Cell Patch-Clamp Recordings from hippocampal neurons. Whole-cell voltage recordings were performed at room temperature on primary cultured hippocampal neurons using an EPC 10 Amplifier (HEKA Electronics, Germany). Electrodes were pulled from thin-walled borosilicate glass capillaries (Warner Instruments, Hamden, Conn.) with a P-97 electrode puller (Sutter Instrument, Novato, Calif.) such that final electrode resistances were 2-3 MΩ when filled with internal solutions. The internal solution for recording $Ca^{2+}$ currents contained (in mM): 110 CsCl, 5 $MgSO_4$, 10 EGTA, 4 ATP $Na_2$-ATP, and 25 HEPES (pH 7.2, 290-310 mOsm/l. The external solution contained (in mM): 128 NaCl, 5 KCl, 10 TEA-Cl, 10 $BaCl_2$, 1 $MgCl_2$, 10 D-glucose, and 10 HEPES (pH 7.3, 310-315 mOsm/l); 1 µM TTX and 1 µM Nifedipine were added just before use to block voltage-gated $Na^+$ and L-type $Ca^{2+}$ channels, respectively.

Whole-cell capacitance and series resistance were compensated with the amplifier. Series resistances compensation (70-80%) was routinely applied. Cells were considered only when the seal resistance was more than 1 GΩ and the series resistance was less than 10MΩ. Linear leak currents were digitally subtracted by P/4. Signals were filtered at 10 kHz and digitized at 10-20 kHz. Analysis was performed using Fitmaster and origin8.1 (OriginLab Corporation, MA, USA). For activation curves, conductance (G) through ion ($Ca^{2+}$) channels was calculated using the equation $G=I/(V_m-V_{rev})$, where $V_{rev}$ is the reversal potential, $V_m$ is the membrane potential at which the current was recorded and I is the peak current. Activation and inactivation curves were fitted to a Boltzmann function $G/G_{max}=1/\{1+\exp[(V-V_{50})/k]\}$, where G is the peak conductance, $G_{max}$ is the fitted maximal G, $V_{50}$ is the half-activation voltage, and k is the slope factor. Additional details of specific pulse protocols are described in the results text or figure legends.

Electrophysiological recordings of capsaicin-evoked TRPV1 currents from DRGs. Whole cell patch-clamp recordings using standard techniques were conducted in adult rat DRG as previously described. The external solution consisted of (in mM): 145 NaCl, 5 KCl, 1 EGTA, 4 $MgCl_2$, 10 HEPES, 10 glucose, pH 7.4; while the internal solution contained the following (in mM): 130 K-aspartate, 20 KCl, 1 EGTA, 1 $MgCl_2$, 10 HEPES, 10 glucose, pH 7.4. Current amplitudes were measured at the peak amplitude recorded in response to a range of capsaicin (30 to 3000 nM) applications and normalized to cell size by dividing by cell capacitance (pA/pF). For acute exposure (10 min), DMSO, TAT control (10 µM) or TAT CBD3 (10 µM) were backfilled in the recording pipettes. For overnight treatment, DMSO, TAT control (10 µM), or TAT-CBD3 (10 µM) were added to the culture medium and neurons were incubated for 12-16 hours. The data was presented as mean±SE. One way ANOVA was used for statistical analysis, with $p<0.05$ considered as statistically significant.

Whole-Cell Patch-Clamp Recordings from Sensory Neurons. Whole-cell voltage recordings were performed at room temperature on primary sensory neurons using an EPC 10 Amplifier (HEKA Electronics, Germany). Electrodes were pulled from thin-walled borosilicate glass capillaries (Warner Instruments, Hamden, Conn.) with a P-97 electrode puller (Sutter Instrument, Novato, Calif.) such that final electrode resistances were 2-3 MΩ when filled with internal solutions. The internal solution for recording $Ca^{2+}$ currents contained (in mM): 150 $CsCl_2$, 10 HEPES, 5 Mg-ATP, and 5 BAPTA (pH 7.2 with KOH). The external solution contained (in mM); 110 N-methyl glucamine (NMG), 2 $CaCl_2$, 30 TEA-Cl, 10 HEPES, and 10 glucose; 1 μM TTX and 1 μM Nifedipine were added just before use to block voltage-gated $Na^+$ and L-type $Ca^{2+}$ channels, respectively.

The intracellular solution for recording $Na^+$ currents contained (in mM): 110 CsCl, 5 $MgSO_4$, 10 EGTA, 4 ATP $Na_2$-ATP, and 25 HEPES (pH 7.2, 290-310 mOsm/L). The external solution contained (in mM): 100 NaCl, 10 tetraethylammonium chloride (TEA-Cl), 1 $CaCl_2$, 1 $CdCl_2$, 1 $MgCl_2$, 10 D-glucose, 4 4-AP, 0.1 $NiCl_2$, 10 HEPES (pH 7.3, 310-315 mOsm/L).

Whole-cell capacitance and series resistance were compensated with the amplifier. Series resistances compensation (70-80%) was routinely applied. Cells were considered only when the seal resistance was more than 1 GΩ and the series resistance was less than 10 M. Linear leak currents were digitally subtracted by P/4. Signals were filtered at 10 kHz and digitized at 10-20 kHz. Analysis was performed using Fitmaster and origin8.1 (OriginLab Corporation, MA, USA). For activation curves, conductance (G) through ion ($Ca^{2+}$) channels was calculated using the equation $G=I/(V_m-V_{rev})$, where $V_{rev}$ is the reversal potential, $V_m$ is the membrane potential at which the current was recorded and I is the peak current. Activation and inactivation curves were fitted to a Boltzmann function $G/G_{max}=1/\{1+\exp[(V-V_{50})/k]\}$, where G is the peak conductance, $G_{max}$ is the fitted maximal G, $V_{50}$ is the half-activation voltage, and k is the slope factor.

For acute exposure (10 min), DMSO, TAT-Scramble (10 μM) or TAT CBD3 (10 μM) were backfilled in the recording pipettes. For overnight treatment, DMSO, TAT-Scramble (10 μM), or TAT-CBD3 (10 μM) were added to the culture medium and neurons were incubated for 12-16 hours. The data was presented as mean±SE.

The differences in activation rate of TRPV1 mediated currents is a very common observation from a number of laboratories (see for example reference Gunthorpe, M. J., Harries, M. H., Prinjha, R. K., Davis, J. B., & Randall, A. Voltage- and time-dependent properties of the recombinant rat vanilloid receptor (rVR1). *J. Physiol.* 525 Pt 3:747-59., 747-759 (2000). The differing opening rates are commonly thought to reflect the hydrophobic nature of capsaicin (8-methyl-N-vanillyl-6-nonenamide), as it must gain access to an intracellular domain of the TRPV1 channel to elicit current. As a result capsaicin's (typically reconstituted in ethanol and then diluted into an aqueous solution) entry into the cell across lipid bilayers can differ from cell to cell. The traces shown in FIG. 24A were selected to reflect currents that were representative of the average current densities for the three conditions. While other traces with more similar opening times were available, they were not necessarily best representatives of the average densities.

Whole cell patch clamp recordings in spinal slices. As previously reported (Baba, H. et al. Removal of GABAergic inhibition facilitates polysynaptic A fiber-mediated excitatory transmission to the superficial spinal dorsal horn. *Mol. Cell. Neurosci.* 24, 818-830 (2003), a portion of the lumbar spinal cord (L4-L5) was removed from mice (3-5 week old) under urethane anesthesia (1.5-2.0 g/kg, i.p.) and kept in pre-oxygenated ice-cold Krebs solution. Spinal segment was placed in a shallow groove formed in an agar block and glued to the bottom of the microslicer stage. Transverse slices (600 μm) were cut on a vibrating microslicer. The slices were perfused with Kreb's solution (8-10 ml/min) that was saturated with 95% $O_2$ and 5% $CO_2$ at 36±1° C. for at least 1-2 h prior to experiment. The Krebs solution contained (in mM): NaCl 117, KCl 3.6, $CaCl_2$ 2.5, $MgCl_2$ 1.2, $NaH_2PO_4$ 1.2, $NaHCO_3$ 25, and glucose 11. Whole cell patch-clamp recordings were made from lamina II neurons in voltage clamp mode. Under a dissecting microscope with transmitted illumination, the substantia gelatinosa (SG, lamina II) is clearly visible as a relatively translucent band across the dorsal horn. Patch pipettes were fabricated from thin-walled, borosilicate, glass-capillary tubing (1.5 mm o.d., World Precision Instruments). After establishing the whole-cell configuration, neurons were held at holding potentials of −70 mV for sEPSC recording. The resistance of a typical patch pipette was 5-10 MΩ. The internal solution contained (in mM): potassium gluconate 135, KCl 5, $CaCl_2$ 0.5, $MgCl_2$ 2, EGTA 5, HEPES 5, ATP-Mg 5. Membrane currents were amplified with an Axopatch 200B amplifier (Axon Instruments) in voltage-clamp mode. Signals were filtered at 2 kHz and digitized at 5 kHz. Data were stored with a personal computer using pCLAMP 10 software and analyzed with Mini Analysis (Synaptosoft Inc.).

Cortical slice recordings of synaptic transmission. CD1 mice (P20-35) were anesthetized and decapitated. The brain was quickly removed, and coronal cortical slices (300 μm thick) were cut with a vibratome (Leica VT1200) in oxygenated artificial cerebrospinal fluid (ACSF). Slices were incubated in ACSF at 32° C. for 1 hour, and then kept at room temperature.

Whole-cell patch clamp recordings were made from cortical layer V pyramidal neurons with glass micropipettes (3-5 M), which were filled with a potassium gluconate based solution (for EPSCs, containing (in mM): K-gluconate 130, HEPES 10, $MgCl_2$ 2, $CaCl_2$ 1, EGTA 11) or cesium gluconate based solution (for IPSCs, containing (in mM): Cs-gluconate 120, CsCl 5, HEPES 10, $MgCl_2$ 1, $CaCl_2$ 0.1, EGTA 4). Cells were voltage-clamped at −70 mV (for EPSCs) or 0 mV (for IPSCs) using a MultiClamp 700B amplifier (Axon Instruments, Foster City, Calif.). To record evoked synaptic responses, biphasic electrical stimuli (100 μsec in duration; 120-300 μA) were delivered via a bipolar electrode, which was placed in the white matter directly below the recoded neurons. Peptides were applied through a local perfusion system to sufficiently cover the area of recorded neurons. Signals were filtered at 2 kHz, digitized, and saved for off-line analysis with pClamp program. Data were expressed as means of currents±SEM. Statistical comparisons were performed on raw data using the paired student's t test with a significant lever of $p<0.05$.

Immunocytochemistry. Indirect immunofluorescence microscopy was performed on fixed, permeabilized CAD cells. 48 h after transfection, CAD cell cultures were fixed with 4% paraformaldehyde (diluted in 0.1 mm PBS) for 10 min at room temperature, permeabilized with 0.2% Triton X-100 for 10 min, and then washed three times with 0.01 mm PBS. The cells were then preincubated with 10% bovine serum albumin (diluted in 0.1 mm PBS) for 1 h at room temperature to block nonspecific binding with the primary antibody. Primary antibodies for rabbit polyclonal N-type/CaV2.2 (Calbiochem) were diluted (in 0.1 mm PBS) to 1:150, and applied to the cells. After incubation at 4° C. overnight, the CAD cells were washed again with PBS, and secondary antibodies (goat anti-mouse Alexa 488 or anti-rabbit Alexa 594, 1:1000; Molecular Probes, Inc., Eugene, Oreg.) were incubated in blocking solution for 45 min at room temperature. Coverslips were mounted in Prolong Gold Antifade mounting media (Molecular Probes, Inc.). Images were acquired on a Nikon Ti swept-field confocal microscope using a 60×, 1.4 NA lens and standard FITC/Texas red fluorescence cubes with a cooled Cascade 512B digital camera (Photometrics, Tucson, Ariz.). Z stack image pairs were captured at an inter-plane distance of 200 nm through the sample. Images were deblurred off line by an iterative deconvolution protocol (Nikon Elements v3.0) using a theoretical point-spread function and pseudocolored for presentation.

Calcium imaging. Calcium imaging experiments were performed as described previously. Briefly, neurons incubated in the growth medium were loaded at 37° C. with 3.3 μM Fura-2AM (Molecular Probes Eugene, Oreg.) to follow changes in cytosolic $Ca^{2+}$ ($[Ca^{2+}]_c$). During calcium imaging, neurons were incubated in the bath solution containing 139 mM NaCl, 3 mM KCl, 0.8 mM $MgCl_2$, 1.8 mM $CaCl_2$, 10 mM NaHEPES, pH 7.4, 5 mM glucose, and 65 mM sucrose. Sucrose was used to maintain osmolarity similar to that in the growth medium (340 mosm). Osmolarity of the solutions was measured with the osmometer Osmette II™ (Precision Systems Inc., Natick, Mass.). Fura-2 fluorescence signals were followed with an inverted microscope Nikon Eclipse TE2000-S using Nikon objective Plan Fluor 20×0.45 NA and a back-thinned EM-CCD camera Hamamatsu C9100-12 (Hamamatsu Photonic Systems, Bridgewater, N.J.) controlled by Simple PCI software 6.2 (Compix Inc., Sewickley, Pa.). The excitation light was delivered by a Lambda-LS system (Sutter Instruments, Novato, Calif.). The excitation filters (340±5 and 380±7) were controlled by a Lambda 10-2 optical filter changer (Sutter Instruments, Novato, Calif.). Fluorescence was recorded through a 505 nm dichroic mirror at 535±25 nm. The fluorescence images were taken every 5 seconds during the time-course of the experiment using the minimal exposure time that provided acceptable image quality. The changes in $[Ca^{2+}]_c$ were monitored by following $F_{340}/F_{380}$ calculated after subtracting the background from both channels. The free $Ca^{2+}$ concentrations were estimated from $F_{340}/F_{380}$ ratios as described previously. Neurons expressing EGFP-tagged CBD3 or EGFP-tagged control peptide were identified by detecting GFP fluorescence excited at 480±20 nm and collected through a 505 nm dichroic mirror at 535±25 nm.

Calcium imaging of sensory Neurons. Ratiometric $Ca^{2+}$ imaging was performed on dorsal root ganglia neurons (without extra NGF added to the media) 12-24 h following isolation. Neurons were loaded with 3 μM Fura-2AM (in Tyrode's buffer; 119 NaCl, 2.5 KCl, 2 $CaCl_2$, 2 $MgCl_2$, 25 HEPES pH 7.5, 30 Glucose, concentrations in mM) for 25 min at room temperature in the dark. Neurons were then washed 3× with Tyrode's buffer before incubating with vehicle (0.05% DMSO), 10 μM TAT-Scramble, or 10 μM TAT-CBD3 for 10 minutes. The bath was then replaced with Tyrode's buffer containing 10 μM Nifedipine or 10 μM Nifedipine+2 μM w-CTX before transferring cells to the imaging stage. Cell fluorescence was measured by digital video microfluorometry with an intensified CCD camera coupled to a microscope and Nikon Elements Software (Nikon Instruments Inc., Melville, N.Y.). Cells were illuminated with a Lamda DG-4 175 W xenon lamp, and the excitation wavelengths of the fura-2 (340/380 nm) were selected by a filter changer. Fura-2 fluorescence ($F_{340}/F_{380}$) was measured every 10 seconds to minimize photo-bleaching. After a baseline of at least 6 images was obtained, neurons were stimulated by addition of excitatory Tyrode's buffer (32 NaCl, 90 KCl, 2 $CaCl_2$, 2 $MgCl_2$, 25 HEPES pH 7.5, 30 Glucose, concentrations in mM) to a final concentration of 45 mM KCl.

Stimulated iCGRP release from rat DRG. Measurement of stimulus-evoked release and content of immunoreactive CGRP (iCGRP) from isolated sensory neurons was performed as published. After 5-7 days in culture, the basal or resting release of iCGRP was measured from cells incubated for 10 minutes in HEPES buffer consisting of (in mM): 25 HEPES, 135 NaCl, 3.5 KCl, 2.5 $CaCl_2$, 1 $MgCl_2$, 3.3 dextrose, and 0.1% (w/v) bovine serum albumin, pH 7.4, and maintained at 37° C. The cells were incubated in HEPES buffer containing stimulus (50 mM KCl) for 10 minutes, and then incubated again with HEPES buffer with 3.5 mM KCl to re-establish resting release levels. The concentration of $K^+$ was chosen because it lies on the middle of the sloped portion of the concentration response curve for KCl-stimulated iCGRP release. The amount of iCGRP released in each incubation was measured by a radioimmunoassay (RIA). The minimum amount of iCGRP detected by the RIA is 5 fmol with a 95% confidence interval. The remaining peptide content in each well was determined by exposing the cells to 2 N acetic acid for 10 minutes. The release of iCGRP during the 10 min incubation period is expressed as percent of the total content. A minimum of three different preparations were used for each condition.

Immunohistochemistry of DRG and Spinal Cord slices. Adult Sprague-Dawley rats were injected (i.p.) with 20 mg/kg FITC-TAT-CBD3 peptide. Rats were then euthanized 15 minutes later with CO2 and transcardially perfused with saline followed by 4% paraformaldehyde. Lumbar dorsal root ganglia and associated spinal cord were immediately removed and post fixed for 24 hours. The tissues were immersed in 4% paraformaldehyde at 4° C. for 24 hours and then in 15% sucrose buffer for 24 hours at 4° C. Sagittal sections of the DRG were serially cut at 14 μm onto SuperFrost Plus microscope slides (Fisher Scientific, Pittsburgh Pa.). At least 6 sections were obtained for immunocytochemical analysis per DRG and spinal cord. Slides were incubated with blocking buffer (3% serum/0.4% Triton, Fisher Scientific, Pittsburgh Pa.) for 3 hours at room temperature, followed by overnight incubation with Anti-NeuN (mouse monoclonal antibody, 1:200; Chemicon, Temecula, Calif.). After primary incubation, secondary antibodies (anti-mouse conjugated to CY3, made in donkey at 1:800, 1.5 hours; Jackson ImmunoResearch, West Grove, Pa.) were used to visualize cells. Slides were washed in PBS for 10 min each (two times) and coverslipped with a PBS/glycerol solution. All tissue sections were also stained with Hoechst 33258 nuclear marker nuclear label (1:1000, 5 minutes; Invitrogen Corporation, Carlsbad, Calif.). The signal from labeled cells was captured with fluorescent microscopes fitted with a CoolSNAP $HQ^2$ charge-coupled devise camera (Photometrics, Tucson, Ariz.). Cells were visualized at 10× magnification using a Nikon Eclipse 90i upright microscope (Melville, N.Y.) and at 20× magnification using a Delta Vision Core (Applied Precision, Issaquah, Wash.) with an Olympus 1×71 microscope (Olympus America Inc., Center Valley, Pa.).

Release of iCGRP from rat spinal cord slices. Male Sprague-Dawley rats (175-200 g) were purchased from Harlan Inc. (Indianapolis, Ind.). The release of iCGRP from spinal cord slices was performed using a modification of a previously described technique. Chen, J. J., Barber, L. A., Dymshitz, J., & Vasko, M. R., Peptidase inhibitors improve recovery of substance P and calcitonin gene-related peptide release from rat spinal cord slices. *Peptides.* 17, 31-37 (1996). Briefly, rats were sacrificed using $CO_2$ asphyxiation and decapitation and the spinal cord from each animal was removed and a 2 cm section of the lumbar enlargement was weighed and chopped parasagitally and transversely into 300 µm cross-sections using a McIllwain Tissue Chopper. The sections from each spinal cord were placed into individual chambers and perfused at a flow rate of 0.5 ml/min with a Hepes buffer, consisting of Hepes 25 mM, NaCl 135 mM, KCl 3.5 mM, MgSO4 1 mM, $CaCl_2$ 2.5 mM, dextrose 3.3 mM, bovine serum albumin 1%, ascorbic acid 200 µM, phe-ala 100 µM, phenylmethanesulfonyl fluoride (PMSF) 10 µM and bacitracin 20 µM, aerated with 95% O2-5% CO2, pH 7.4-7.5, and maintained at 36-37° C. After 30 min, 1.5 ml samples were collected into test tubes containing 75 µl of 1 M 2-(N-morpholino) ethanesulfonic acid (MES) buffer (pH 6.7-6.9) every 3 min. Basal release was established by first perfusing the tissue with Hepes buffer for 9 min and then with Hepes buffer containing 20 µM of the control peptide or CBD3 for 9 min. To evoke iCGRP release, tissue was then perfused for an additional 9 min with Hepes buffer containing 500 nM capsaicin with 20 µM of the scramble control peptide or CBD3. To demonstrate a return to basal release after stimulation, the tissue was perfused with Hepes buffer alone for another 15 min. After the release protocol was complete, the spinal cord tissue was recovered and homogenized in 4 ml 0.1 N HCl. The homogenate was centrifuged at 3000×g for 20 min at 4° C. and the supernatant was serially diluted with Hepes buffer and assayed for iCGRP by RIA, as previously described. The total peptide content was the amount of iCGRP released during the perfusion and the amount remaining in the tissues. This value was used to determine the amount of release as % of total content.

Stimulated iCGRP release from mouse DRGs in culture. Measurement of stimulus-evoked release and content of immunoreactive CGRP (iCGRP) from isolated sensory neurons was performed as published. After 5-7 days in culture, the basal or resting release of iCGRP was measured from aliquots of media removed from cells incubated for 10 minutes in non-depolarizing HEPES buffer consisting of (in mM): 25 HEPES, 135 NaCl, 3.5 KCl, 2.5 $CaCl_2$, 1 $MgCl_2$, 3.3 dextrose, and 0.1% (w/v) bovine serum albumin, pH 7.4, and maintained at 37° C. The buffer was removed and the cells were incubated in a depolarizing HEPES buffer (50 mM KCl) for 10 minutes, media was removed and aliquotted. The cells were then incubated again with non-depolarizing HEPES buffer with 3.5 mM KCl to re-establish resting release levels, buffer was removed and aliquotted. The concentration of $K^+$ was chosen because it lies on the middle of the sloped portion of the concentration response curve for KCl-stimulated iCGRP release. The amount of iCGRP released was measured in aliquots of the incubation samples by a radioimmunoassay (RIA). The minimum amount of iCGRP detected by the RIA is 5 fmol with a 95% confidence interval. The remaining peptide content in each well was determined by exposing the cells to 2 N acetic acid for 10 minutes. Aliquots of the acid solution were diluted with HEPES buffer and similarly assay for iCGRP. This value was added to the amount of iCGRP released in the previous incubations to yield the total iCGRP content per well. The release of iCGRP during the 10 min incubation periods is expressed as percent of the total content. DRGs were either exposed to TAT-Scramble or TAT-CBD3 peptides (10 µM) overnight, and/or the peptides were included throughout the first basal wash and throughout the high $K^+$ exposures. A minimum of three different preparations were used for each condition.

Laser Doppler flowmetry. Male rats were anesthetized with ketamine/xylazine and the animal's body temperature was maintained at 37° C. with a homeothermic blanket. For the measurement of meningeal blood flow, the animals head was fixed in a stereotaxic frame and a cranial window prepared with the dura left intact. Dural blood flow was measured with a laser Doppler flowmeter (TSI, MN). A needle type probe was placed over a large branch of the middle meningeal artery (MMA), distant from visible cortical blood vessels and the cranial window kept moist with synthetic interstitial solution (SIF) consisting of: 135 mM NaCl, 5 mM KCl, 5 mM $CaCl_2$, 1 mM $MgCl_2$, 10 mM HEPES, 10 mM D-glucose (pH 7.3). Blood flow was recorded on-line at a frequency of 1 Hz using Axoscope software (Axon Instruments, CA).

Drug administration. Drugs or peptides were diluted fresh daily in SIF. TAT-CBD3 or TAT-scramble was administered to the dural surface (50 µl, 30 µM). Capsaicin was dissolved in SIF to 100 nM for nasal administration. To stimulate the nasal mucosa, 50 µl of capsaicin solution was applied over a 30 sec period at a site 2 mm into the right nostril using a Pipetman pipette. SIF or SIF containing 0.1% ethanol was applied to the dura or nasal mucosa as a control in all experiments 15 minutes prior to drug application and had no effect on meningeal blood flow.

Data collection and statistics. Data was collected at 1 Hz and binned by averaging 60 samples (1 minute intervals) for statistical analysis or 10 samples (10 sec intervals) for graphical representation. Basal blood flow was determined as the mean flow rate measured during a 3 minute period prior to drug application and the effects of test compounds were calculated by comparing the peak response within three minutes of administration to the average blood flow in the three minutes proceeding administration. Changes in blood flow for each animal were calculated, averaged within treatment groups and expressed as percentage changes relative to the basal blood flow. Comparison of blood flow changes was performed using an unpaired Student's t-test. Data values are presented as means±SEM. The significance level for all tests was set at $p<0.05$.

Formalin Test. Rats were placed in an open Plexiglas observation chamber for 30 min to accommodation. The animals were gently restrained while the dorsal surface of the hindpaw was subcutaneously administered with 50 µl of formalin 2.5% using a 31 G needle. The nociceptive behavior was observed for 60 min, divided into blocks of 5 min and the number of flinches was determined in each block. A mirror was placed behind the chamber to enable unhindered observation of the formalin-injected paw. The TAT-CBD3 or the TAT control peptide (30 µM in 20 µl) was subcutaneously injected 30 min before the formalin injection.

Eye-wipe test. Male rats (~150 g) were brought to a quiet, temperature-controlled (22-25° C.) behavioral laboratory in individual cages in which they were allowed to acclimate for at least 0.5 h prior to testing. TAT CBD3 peptide, TAT control peptide or vehicle was pipetted directly into the right eye in a volume of 40 µl and the resulting nocifensive behavior was measured. Nocifensive behavior was defined as time holding the eye shut or time spent actively grooming or wiping the treated eye. This nocifensive behavior was recorded for five minutes and followed by capsaicin (3 µM in 40 µl saline) application into the pretreated eye. Nocifensive behavior was again quantified for 5 minutes following capsaicin application, as described previously. Observers were blinded to treatments. All data are presented as mean±SEM. Significant differences between groups were assessed by two-way analysis of variance with Bonferroni post-tests. Data were analyzed with GraphPad Prism 4.0 (GraphPad, San Diego, Calif., USA).

ddC model of peripheral neuropathy. Hyperalgesia and allodynia were established by a single injection (25 mg/kg) of the antiretroviral drug 2',3'-dideoxycytidine (ddC, Sigma)

given i.p. A single administration of ddC produced a significant bilateral decrease in paw withdrawal threshold to von Frey hair stimulation from post-injection day (PID) 3 through the last day of testing at PID42.

The von Frey test was performed on the area of the hind paws as previously described. Briefly, the rat was placed on a metal mesh floor and covered with a transparent plastic dome where the animal rested quietly after an initial few minutes of exploration. Animals were habituated to this testing apparatus for 15 minutes a day, two days prior to pre-injection behavioral testing. Following acclimation, each filament was applied to six spots spaced across the glabrous side of the hind paw; two distinct spots for the distribution of each nerve branch (saphenous, tibial and sural). Mechanical stimuli were applied with seven filaments, each differing in the bending force delivered (10, 20, 40, 60, 80, 100, and 120 mN), but each fitted a flat tip and a fixed diameter of 0.2 mm. The force equivalence of mN to grams is: 100 mN=10.197 grams. The filaments were tested in order of ascending force, with each filament delivered for 1 second in sequence from the 1st to the 6th spot alternately from one paw to the other. The interstimulus interval was 10-15 seconds. A cutoff value of 120 mN was used; animals that did not respond at 120 mN were assigned that value.

Measurements were taken on 3 successive days before rats were subjected to either a TAT control or TAT CBD3. Stimuli were applied randomly to left and right hind paws to determine the stimulus intensity threshold stiffness required to elicit a paw withdrawal response. The incidence of foot withdrawal was expressed as a percentage of six applications of each filament as a function of force. A Hill equation was fitted to the function (Origin version 6.0, Microcal Software) relating the percentage of indentations eliciting a withdrawal to the force of indentation. From this equation, the threshold force was obtained and defined as the force corresponding to a 50% withdrawal rate. A threshold that exhibits at least a −20 mN difference from the baseline threshold of testing in a given animal is representative of neuropathic pain.

Threshold values were statistically analyzed for each foot separately and the significance of differences between the average of at least two pre-injection tests and the mean obtained for each post-injection test. In all tests, baseline data were obtained for the ddC-treated and shamtreated groups before drug or vehicle administration. Within each treatment group, post-administration means were compared with the baseline values by repeated measures analyses of variance (RMANOVA) followed by post hoc pairwise comparisons (Student-Newman-Keuls Method). A probability level of 0.05 indicates significance.Procedures involving animals and their care were in accordance with the Guide for the Care and Use of Laboratory Animals (National Institutes of Health publication 85-23, Bethesda, Md., USA) and approved by the Institutional Animal Care and Use Committee of the Indiana University School of Medicine. Sprague-Dawley rats for behavioral studies were purchased from Harlan Inc. (Indianapolis, Ind.) while CD1 mice for slice electrophysiology experiments were from Charles River (Chicago, Ill.).

Peptides. CBD3 (SEQ ID NO.: 1), TAT control (SEQ ID NO.: 2) and TAT CBD3 (SEQ ID NO.: 11) were synthesized by Antagene Inc. (Sunny.vale, CA) and were verified by mass spectroscopy (Department of Chemistry, Indiana University School of Medicine) prior to use.

Peptides. TAT-Scramble (SEQ ID NO.: 2); a random sequence with no homology to any known sequence) and TAT-CBD3 SEQ ID NO.: 11) were synthesized by Antagene Inc. and verified by mass spectroscopy (Department of Chemistry, IUSM).

Additional sequences (SEQ ID NOs 3-10, 12, and 13) that are projected to interact with CRMP-2 were created by in silico modelling these are included in Table 2, as are other polypeptides that may be of use in practicing and/or studying the invention.

TABLE 2

| SEQ ID NO. | SEQUENCE. | ABBREVIATION |
| --- | --- | --- |
| 1. | ARSRLAELRGVPRGL | CBD3 |
| 2. | YGRKKRRQRRRWEAKEMLYFEALVIE | TAT SCRAMBLE |
| 3. | ARSRAAELRGVPRGL | Exemplary polypeptide 2 |
| 4. | ARPRLAELRGVPRGL | Exemplary polypeptide 3 |
| 5. | ARPRRAELRGVPRGL | Exemplary polypeptide 4 |
| 6. | ARSRLAELRRVPRGL | Exemplary polypeptide 5 |
| 7. | ARSRLAELRGVPRFL | Exemplary polypeptide 6 |
| 8. | ARSRLKELRGVPRGL | Exemplary polypeptide 7 |
| 9. | ARSRLADLRGVPRGL | Exemplary polypeptide 8 |
| 10. | ARSWLAELRGVPRGL | Exemplary polypeptide 9 |
| 11 | YGRKKRRQRRRARSRLAELRGVPRGL | TAT-CBD3 |
| 12. | GRKKRRQRRRPQ | HIV-1 TAT cell membrane transduction domain |
| 13. | YGRKKRRQRRR | Modified TAT cell membrane transduction domain of SEQ ID NO.: 12 |

Cell culture. Primary hippocampal cultures from postnatal day 1 were prepared as described previously. Lumbar dorsal root ganglion (DRG) were isolated from young adult rats, dissociated and primary sensory neurons cultured as previously described. Neuronal catecholamine A differentiated (CAD) cells were cultured as previously described.

Biochemistry and immunocytochemistry experiments. Immunoprecipitation, in vitro binding assays and surface biotinylation were performed as described previously. The binding between TAT CBD3 or TAT control peptides and CaV2.2 L1- or Ct-dis-GST fusion proteins was determined by surface plasmon resonance using a BIAcore3000 instrument (Biacore AB, Uppsala, Sweden).

Neurotransmitter release radioimmunoassay. Measurement of stimulus-evoked release and content of immunoreactive CGRP (iCGRP) from isolated sensory neurons was as published. The release of iCGRP from spinal cord slices was performed using a modification of a technique as previously described.

Electrophysiological recordings. Whole-cell recordings from hippocampal neurons were made as described previously. To determine effects of TAT CBD3 on synaptic transmission, 300 µM thick coronal cortical slices from CD1 mice (postnatal day 20-35) with a vibratome (Leica VT1200) were cut in oxygenated artificial cerebrospinal fluid (ACSF). Slices were incubated in ACSF at 32° C. for 1 hour, and then kept at room temperature. Slice recordings were made from cortical layer V pyramidal neurons with glass micropipettes (3-5 MΩ) filled with a potassium gluconate based solution (for EPSCs, containing (in mM): K-gluconate 130, HEPES 10, $MgCl_2$ 2, $CaCl_2$ 1, EGTA 11) or cesium gluconate based solution (for IPSCs, containing (in mM): Cs-gluconate 120, CsCl 5, HEPES 10, $MgCl_2$ 1, $CaCl_2$ 0.1, EGTA 4). Cells were voltage-clamped at −70 mV (for EPSCs) or 0 mV (for IPSCs) using a MultiClamp 700B amplifier (Axon Instruments, Foster City, Calif.). To record evoked synaptic responses, biphasic electrical stimuli (100 µsec in duration; 120-300 µA) were delivered via a bipolar electrode, which was placed in the white matter directly below the recoded neurons. TAT control or TAT CBD3 peptides (30 µM) were applied through a local perfusion system to sufficiently cover the area of recorded neurons. Signals were filtered at 2 kHz, digitized, and saved for off-line analysis with pClamp program.

Dural blood flow analyses. Dural blood flow was measured with a laser Doppler flowmeter (TSI, MN). A needle type probe was placed over a large branch of the middle meningeal artery (MMA), distant from visible cortical blood vessels and the cranial window kept moist with synthetic interstitial solution (SIF) consisting of: 135 mM NaCl, 5 mM KCl, 5 mM $CaCl_2$, 1 mM $MgCl_2$, 10 mM HEPES, 10 mM D-glucose (pH 7.3). Blood flow was recorded on-line at a frequency of 1 Hz using Axoscope software (Axon Instruments, CA). Detailed methodology is described in the Materials and Methods section.

Behavioral analyses. All behavioral experiments were conducted with the observers blinded to treatments. To produce inflammatory pain, formalin (2.5%, 50 µl) was subcutaneously injected into the dorsal surface of the hindpaw. For the formalin test, two animals in adjacent chambers at one time were observed for flinching behaviors. Data are presented as a time course or the cumulative number of flinches during phase 1 (0-8 min) or phase 2 (9-60 min). For the eye-wipe test, vehicle, TAT control or TAT CBD3 peptides (30 µM, 40 µl) were pipetted directly into the right eye and the resulting nocifensive behavior was measured. Nocifensive behavior was defined as time the animal spent (1) holding the eye shut, (2) time spent actively grooming, or (3) wiping the treated eye. This nocifensive behavior was recorded for five minutes and followed by capsaicin (3 µM; 40 µl saline) application into the pretreated eye. Nocifensive behavior was again observed for 5 minutes following capsaicin application, as described previously.

Hyperalgesia and allodynia were established by a single injection (25 mg/kg) of the antiretroviral drug 2',3'-dideoxycytidine (ddC, Sigma) given i.p. A single administration of ddC produced a significant bilateral decrease in paw withdrawal threshold to von Frey hair stimulation from post-injection day (PID) 3 through the last day of testing at PID42. The von Frey test was performed on the area of the hind paws as previously described.

Paw edema. The paw thickness was evaluated before and at the end of the formalin nociceptive test using a digital caliper (Mitutoyo Corporation, USA) with a resolution of 0.001 mm. The measurements were conducted with the observer blinded to the treatments.

Rotarod test for motor coordination. The rotarod test was performed as described previously (Onyszchuk, G., He, Y. Y., Berman, N. E., & Brooks, W. M. Detrimental effects of aging on outcome from traumatic brain injury: a behavioral, magnetic resonance imaging, and histological study in mice. *J. Neurotrauma.* 25, 153-171 (2008)) with slight modifications. Briefly, the latency to fall off a rotating rod was measured at two different rotational accelerations (fast and slow). The rotarod device (IITC Life Science, Inc., Woodland Hills, Calif., USA) consists of a metal rod with hard plastic drums (diameter: 1.25 in) in each of five individual lanes. For slow acceleration, the device was accelerated from 1 rpm to 18 rpm over 90 seconds, with each trial lasting a maximum of 120 seconds. For fast acceleration, the device was accelerated from 1 rpm to 30 rpm over 90 seconds, with each trial lasting a maximum of 120 seconds. The trials ended when the mouse (C57BL6) either fell off the rod or clung to the rod as it made one complete rotation. The rotarod tests were performed before the injection to score the baseline latencies for each animal. These trials also served to acclimate the animals to the test paradigm. Four trials each of the fast and slow acceleration paradigms were performed, and the average of the two middle latencies was taken as the baseline. Following i.p. injection of vehicle or peptides (10 mg/kg or 50 mg/kg), the mice were tested with three trials each of fast and slow acceleration. All experiments and analyses were done in a double-blind manner.

The rotarod test for motor coordination was performed as described with slight modifications. Following i.p. injection of vehicle or peptides, mice were tested with three trials each of fast and slow acceleration. The Morris water maze test was used to test reference/spatial memory. Mice were trained prior to the i.p. injection of TAT-Scramble or TAT-CBD3 peptides for 4 consecutive days (4 trials/day). Performance was evaluated 3 days following injection.

The light-dark box test and the elevated plus maze were used as measures of anxiety-associated behaviors. The tail suspension test was performed to evaluate despair- and depression-associated behavior.

Morris water maze test of spatial/reference memory. The Morris water maze test was used to test spatial memory. The maze consisted of a plastic pool (100 cm in diameter and 60 cm in depth) filled with water to a depth of 26.5 cm, with a clear Plexiglas stand (10 cm in diameter and 26 cm in height [i.e., 0.5 cm below the water's surface]) used as the hidden goal platform. The mice were trained prior to the injection for 4 consecutive days (4 trials/day). For each daily block of four trials, the mice were placed in the pool facing the wall. Trials were initiated from each of the four possible start locations (north, east, south, west) in a randomized manner. A maximum of 60 sec was allowed for each mouse to find the hidden platform. If the mouse failed to find the platform within the allotted time, it was placed on the platform by the experimenter where it remained for 30 sec before being placed in a heated incubator between trials (4-min inter-trial interval). Mice were excluded from the study if their average latency to locate the platform on day 4 of the trials was greater than 50 sec. As a control for nonspecific deficits such as visual processing and motivation, additional trials were performed with the hidden platform positioned below a ball which served as a marker. All experiments and analyses were done in a double-blind manner.

Anxiety-behavior testing Anxiety occurs when there is conflict between risk and reward. The Light-Dark Box test (LDBT) and the elevated plus maze (EPM) are accepted tests of anxiety-associated behavior that assess the conflict mice have against hiding in enclosed dark areas (i.e., dark box or closed arm) and their tendency to explore novel environments (i.e., white box or open arm). Lalonde, R. & Strazielle, C. Relations between open-field, elevated plus-maze, and emergence tests as displayed by C57/BL6J and BALB/c mice. *J.*

*Neurosci. Methods.* 171, 48-52 (2008). These tests are also sensitive to anxiolytic drug treatments.

Light-Dark Box test as a measure of anxiety-associated behavior. For the light-dark box test (LDBT), there were two adjoined light and dark compartments boxes with a 7 cm square opening to allow mice to move between them. The black box was covered (20 cm×40 cm×30 cm height) and the white box (20 cm×40 cm×30 cm height) was open and illuminated (40 W). Each mouse was placed into the white compartment and the white compartment was video recorded for later analyses using ANY-maze software (version 4.75, Stoelting, Wood Dale, Ill.) which is a video tracking system designed to automate testing in behavioral experiments. The main parameters were duration of time spent in the light box; the latency to enter the dark box; and the number of transitions between the light and dark box. Mice injected with the scrambled control peptide spent approximately 25% of the time in the light box which is comparable to baseline durations (approximately 23%) observed in C57BL6 mice in another study.

Elevated Plus Maze Anxiety Test (EPM) as a Measure of Anxiety-Associated Behavior Immediately following the LDBT, rats were place in the center area of the EPM where the two arms intersect. The EPM measures many relevant anxiety related behaviors such as: number of poke and full entries into and duration spent in closed versus open arm. The arena dimensions are the following: each arm is 5 cm wide and 35.5 cm long, closed walls are 15 cm high. The arms and central platform of the apparatus are elevated to a height of 62 cm. Behavior was video recorded for later analyses using ANY-maze software (version 4.75, Stoelting, Wood Dale, Ill.) which is a video tracking system designed to automate testing in behavioral experiments. The main parameters were duration of time spent in the open and closed arm and number of entries into the arms. Mice injected with the TAT-Scramble (10 mg/kg) control peptide spent approximately 30% of the time in the open arm compared to the closed arm, which is comparable to baseline durations (approximately 26%) observed in C57BL6 mice in another study.

Depression/Despair-behavior testing. Since rodents such as mice and rats display immobile postures when placed in inescapable stressful situations, immobility behavior in the tail suspension test (TST) or forced swim test (FST) is used as a measure of "depression" or "despair"-associated behavior. Furthermore, administering antidepressant treatments prior to testing reduces immobility behavior. Therefore TST and FST are often used to screen novel drugs for depressant or anti-depressant properties.

Tail suspension test as a measure of depression-associated behavior. Immediately following the EPM test, the TST was conducted according to standard procedure between 8:00 AM and 2:00 PM. Cryan, J. F., Mombereau, C., & Vassout, A. The tail suspension test as a model for assessing antidepressant activity: review of pharmacological and genetic studies in mice. *Neurosci. Biobehav. Rev.* 29, 571-625 (2005). Briefly, each mouse was suspended by the tail at a height of 40 cm by taping the rail to a horizontal bar so that the tail is vertical to the bar. Behavior was video recorded for 5 min and later analyzed by an experimenter, whom was blind to the treatments. An animal was considered to be immobile when it did not show any movement and hanged passively. If a mouse climbed its tail the mouse was gently pulled back down and the trial continued. Mice that climbed their tails for more than 20% of the trial (i.e. >60 seconds) were eliminated from the final analysis. Duration and frequency of immobility was the main parameters measured. Mice injected with the scrambled control peptide were immobile approximately 26% of the TST duration which is equivalent to baseline immobility durations (approximately 27%) observed in C57B16 mice in another recent study.

Statistical analyses. Analysis of variance or Student's t-test to determine significant differences between sample groups was used. $P<0.05$ was considered significant in all cases. Identification and in vitro characterization of a CRMP-2-$Ca^{2+}$ channel uncoupling peptide.

Referring now to FIG. 1. A peptide derived from CRMP-2 suppresses the CaV2.2-CRMP-2 interaction in vitro. (FIG. 1A) Cartoon illustrating the main hypothesis: the $Ca^{2+}$ channel binding domain (CBD3; red region in structure), encompassing amino acids 479-499 of CRMP-2, interacts with CaV2.2, causing increased surface trafficking and transmitter release and increased sensitivity to pain. Disrupting this interaction is predicted to result in decreased CaV2.2 trafficking, decreased transmitter release and a reduction in pain hypersensitivity. (FIG. 1B) Summary of normalized binding of CaV2.2 to 15 amino acid peptides (overlapping by 12 amino acids) encompassing full length CRMP-2 overlaid with rat brain synaptosomes. The amino acid sequence of peptide #96, designated CBD3 is shown. (FIG. 1C) Sensorgram depicting binding of CBD3 (1, 3 or 5 µM; solid traces) or control peptide (1, 3 or 5 µM; dotted traces) to immobilized cytosolic loop 1 (L1) and the distal end of the C-terminus (Ct-dis) of CaV2.2. Dissociation was monitored for 4 min. RU refers to resonance units. (FIG. 1D) In vitro binding assay of L1-GST and Ct-dis-GST fusion proteins with CRMP-2 with control peptide or CBD3 peptide (10 µM). CRMP-2 bound to L1 and Ct-dis was probed with an antibody against CRMP-2. Surface detection of CaV2.2 expressed alone (FIG. 1E), but not when CBD3 fused to GFP is over-expressed (FIG. 1F). Below, the normalized surface intensity (SI) between the arrows demarcating the surface of cells shown in (FIGS. 1E and 1F), (FIG. 1G). Summary of the percent of cells exhibiting surface expression of CaV2.2. (FIG. 1H) Immunoblots of streptavidin-enriched surface fractions of neuronal cells expressing nothing (control), a region encompassing amino acids 94-166 of CRMP-2 (CBD1), or CBD3 probe with a CaV2.2 antibody (n=3). (FIG. 1I) Top, voltage protocol. Bottom, exemplar traces from hippocampal neurons overexpressing CRMP-2 (black trace) or CRMP-2+CBD3 (red trace). (FIG. 1J) Peak current density (pA/pF) measured at +10 mV for CRMP-2- and CRMP-2+CBD3-transfected neurons. Numbers in parentheses represents number of cells rested. *, $p<0.05$ versus CRMP-2, Student's t-test.

Figure 1C:
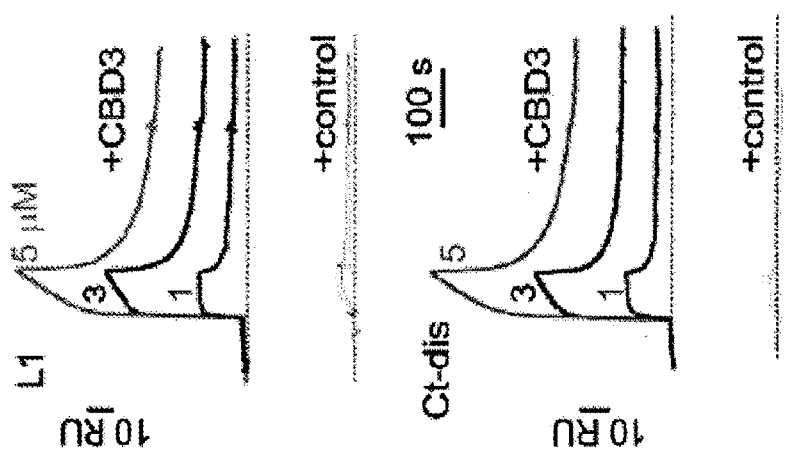
FIG. 1C. Sensorgrams measured with either control or CBD3.
Figure 1D:
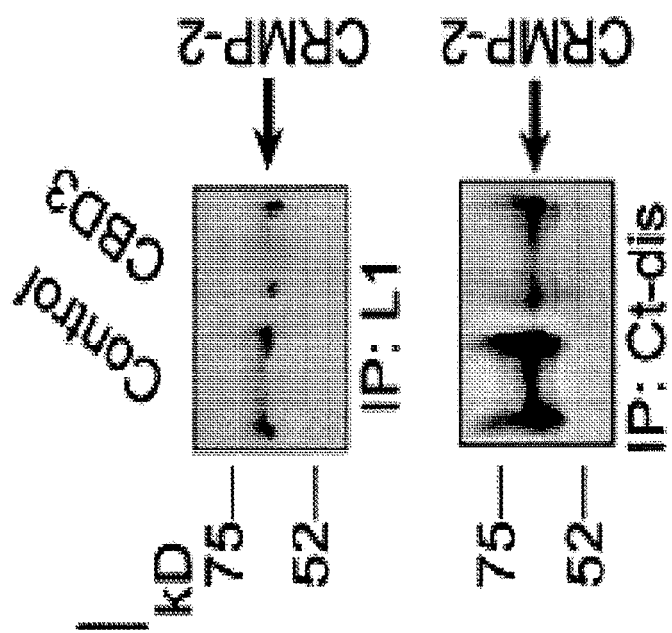
FIG. 1D. Gels showing in vitro binding of either control or CBD3 with CRMP-2.
Figure 1E:
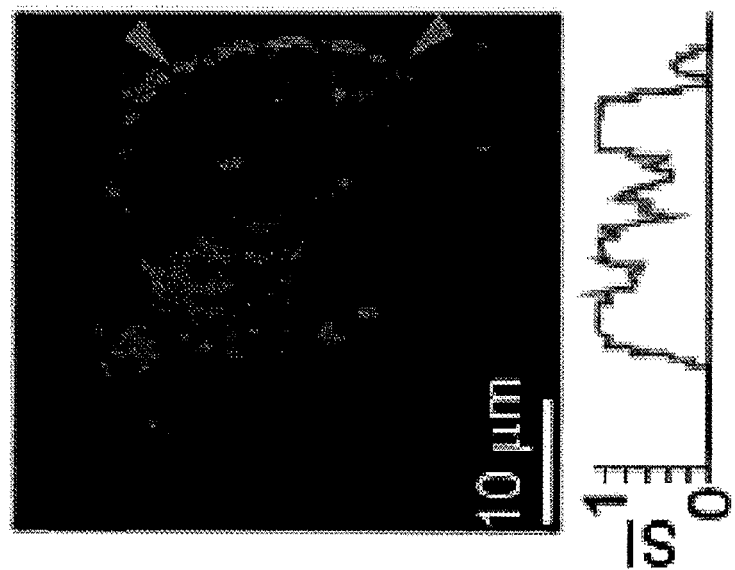
FIG. 1E. Image showing presence of CaV2.2 on cell surface.
Figure 1F:
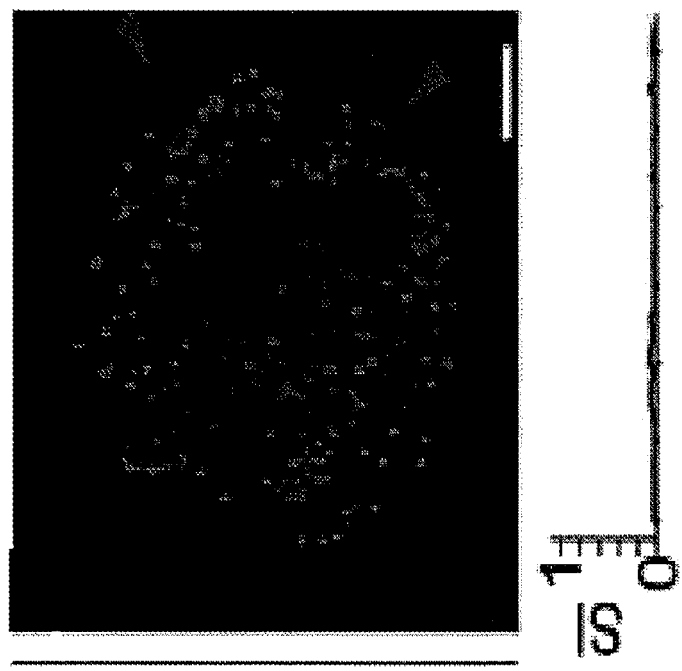
FIG. 1F. Image showing CaV2.2 in presence of over-expressed CBD3 fused to GFP.

In order to develop a reagent to disrupt the interaction of CRMP-2 with the CaV2.2 complex in vivo, a series of overlapping 15-amino-acid peptides covering CRMP-2 were synthesized. A peptide consisting of amino acids 479-499 of CRMP-2, CBD3, bound to the CaV2.2 (FIG. 1B) via its first intracellular loop (L1) and the end of the C-terminus (Ct-dis), regions which was previously shown to be important for the CRMP-2-CaV2.2 interaction. Using surface plasmon resonance, it was found that CBD3 peptide, but not a control peptide, bound to immobilized L1 and Ct-dis (FIG. 1C). The CBD3 peptide disrupted the interaction between CRMP-2 and the L1 or Ct-dis regions of CaV2.2 in vitro (FIG. 1D).

Figure 1H:
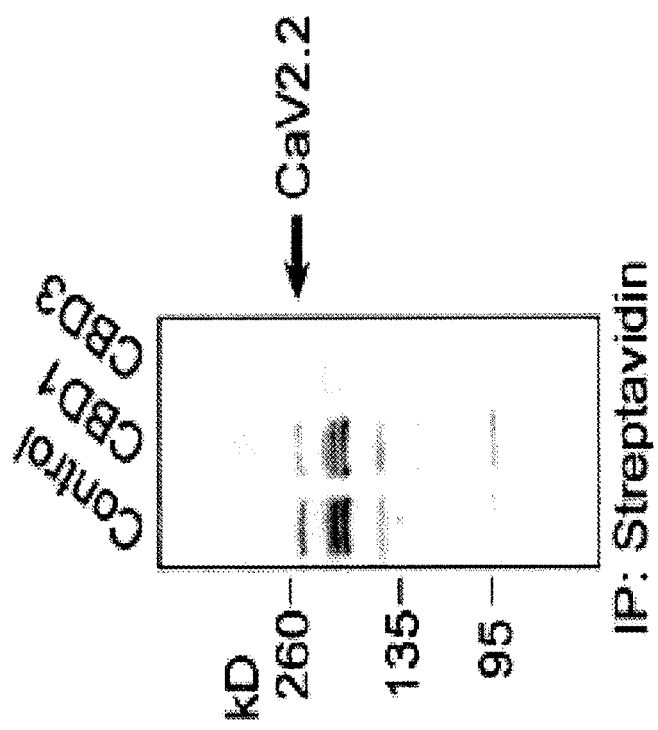
FIG. 1H. Immunoblots showing surface CaV2.2 expression levels in presence of CBD1, or CBD3 or neither (i.e control).
Figure 1I:
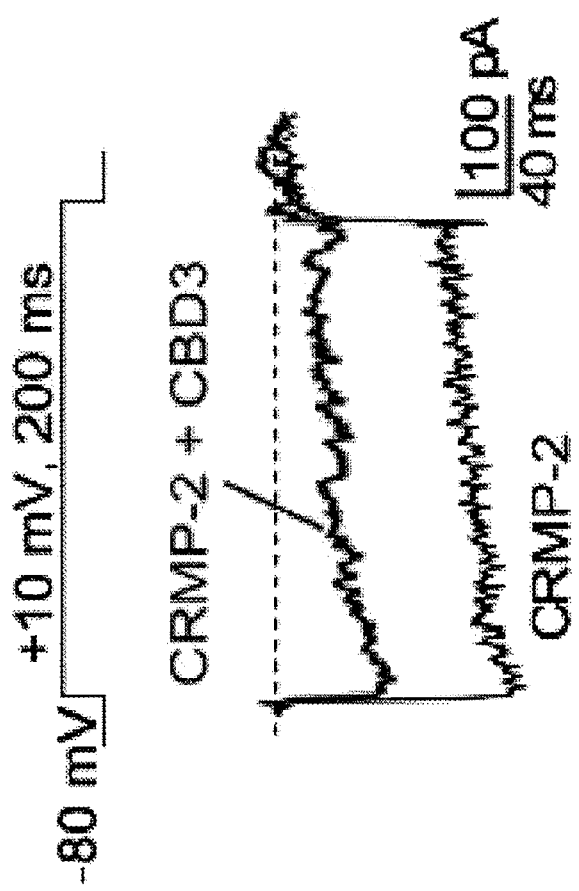
FIG. 1I. Traces of Ca2+ current density from cells expressing CRMP-2 or CRMP-2+CBD3.
Figure 1J:
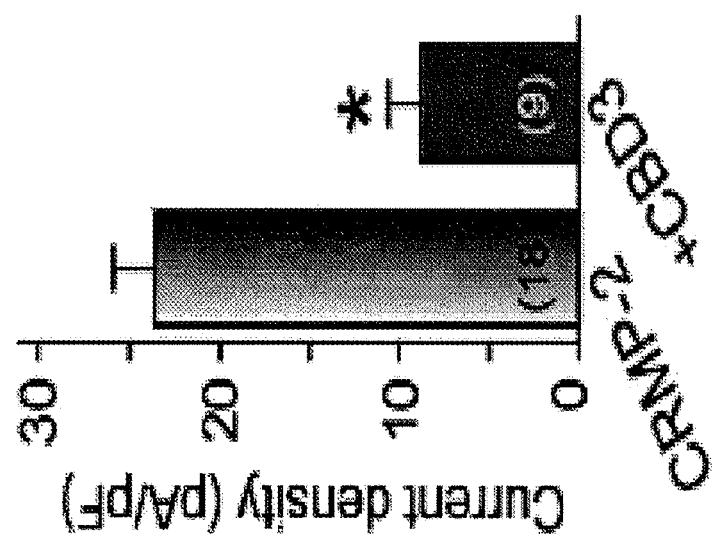
FIG. 1J. Bar graph showing current density measured with either CRMP-2 or CRMP-2+CBD3.

Since it had been shown previously that CRMP-2 facilitates surface trafficking of CaV2.2, CBD3 was tested to determine if it could uncouple CRMP-2 from CaV2.2 and affect trafficking and CaV2.2 activity. Co-expression of CaV2.2 with CBD3 in a neuronal cell line resulted in almost complete retention of the channel in cytoplasmic aggregates (FIGS. 1E-G) and prevented surface expression (FIG. 1H). Moreover, co-expression of CRMP-2 with CBD3 in hippocampal neurons eliminated the CRMP-2-mediated increase in CaV2.2 current density (FIGS. 1I and 1J) reported by us previously.

Referring now to FIG. 7. Expression of CBD3 in hippocampal neurons inhibits plasma membrane depolarization induced increase in cytosolic $Ca^{2+}$ $[Ca^{2+}]_c$. Rat cultured hippocampal neurons, 5 DIV, were transfected with DNA constructs encoding CBD3 or a control peptide sequence using Lipofectamine as described previously[1]. The transfection rate was 1-2%. After culturing for 5 days in 5% $CO_2$/air at 37° C., cells were loaded with Fura-2AM and changes in $[Ca^{2+}]_c$ were recorded using time-lapse, wide-field fluorescence microscopy. Representative bright field images of neurons expressing control (FIG. 7A) or CBD3 (FIGS. 7B-D) Fluorescence (due to expression of enhanced green fluorescent (EGFP) protein), images of the same neurons as in (FIGS. 7A, 7B, 7E, and 7F). Experimental traces, in response to depolarization with KCl for 30 sec, obtained from individual neurons in the same viewing areas after background subtraction and conversion into $[Ca^{2+}]_c$. In both FIGS. 7E and 7F, n indicates the number of neurons from which Fura-2 fluorescence was recorded in the given experiment. Grey traces show signals from individual neurons without transfection (NT) while orange and green traces show signals form neurons expressing control or CBD3, respectively. The average $[Ca^{2+}]_c$ of several such experiments is presented in FIGS. 2A-E.

Referring now to FIG. 2. CBD3 affects cytosolic $Ca^{2+}$ ($[Ca^{2+}]_c$) and presynaptic transmitter release. Rat hippocampal neurons, cultured for 5 days in vitro were transfected with DNA constructs encoding CBD3 or control vector using Lipofectamine were loaded with Fura-2AM and changes in $[Ca^{2+}]_c$, in response to plasma membrane depolarization with potassium chloride (KCl, 30 mM), were recorded using time-lapse, wide-field fluorescence microscopy. (FIGS. 2A and 2B) Averaged $[Ca^{2+}]_c$ responses obtained from neurons expressing control plasmid (control), CBD3 and neurons not transfected (NT). In both panels, n indicates the number of neurons from which Fura-2 fluorescence was recorded. (FIG. 2C) Summary of average peak $[Ca^{2+}]_c$ responses from control (n=207), CBD3 (n=11) or NT (n=11) neurons. Representative images and traces from a typical calcium imaging experiment are shown in FIG. 7. (FIG. 2D) Representative traces of evoked EPSCs in cortical layer V pyramidal neurons to 5 Hz stimulus at baseline (black, left traces), and after application of 10 µM TAT control peptide (top, blue traces) or 10 µM TAT CBD3 peptide (bottom, red traces). Voltage-clamp recordings (Vh=−70 mV) were used to record synaptic responses and stimulus intensities were in the range of 120-300 µA, about 2 times the threshold stimulus. Note the significant decrease in amplitude of evoked EPSCs after the application of TAT CBD3 peptide. TAT CBD3 peptide attenuated amplitude of evoked EPSCs, defined as the percent change before compared to after local perfusion of peptide (FIG. 2E), and increased pair pulse ratio (FIG. 2F) compared to TAT control peptide. *, p<0.05; ** p<0.01.

Figure 2A:
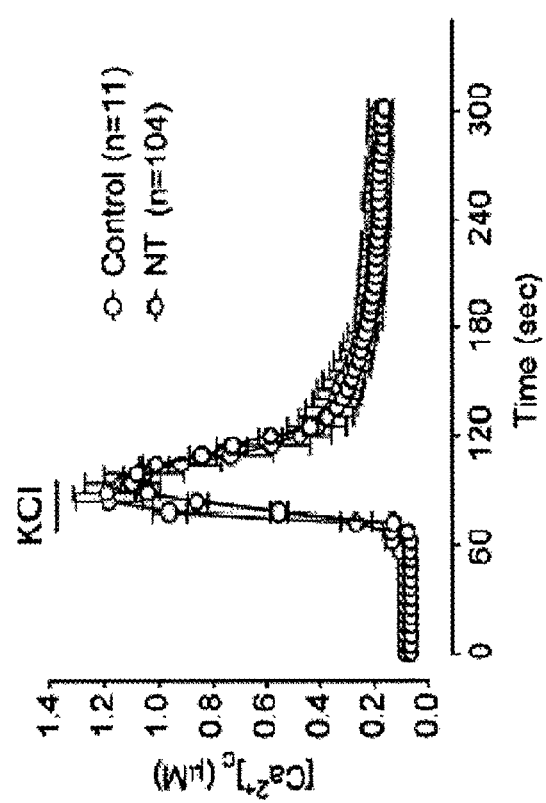
FIG. 2A. Traces of $Ca^{2+}$ concentrations v. time measured unit for control cells.
Figure 2B:
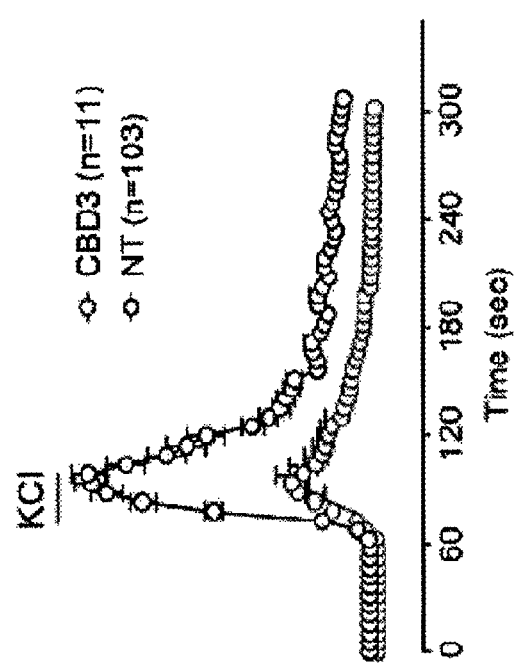
FIG. 2B. Trace of $Ca^{2+}$ concentrations v. time measured for CBD3 expressing cells.
Figure 2C:
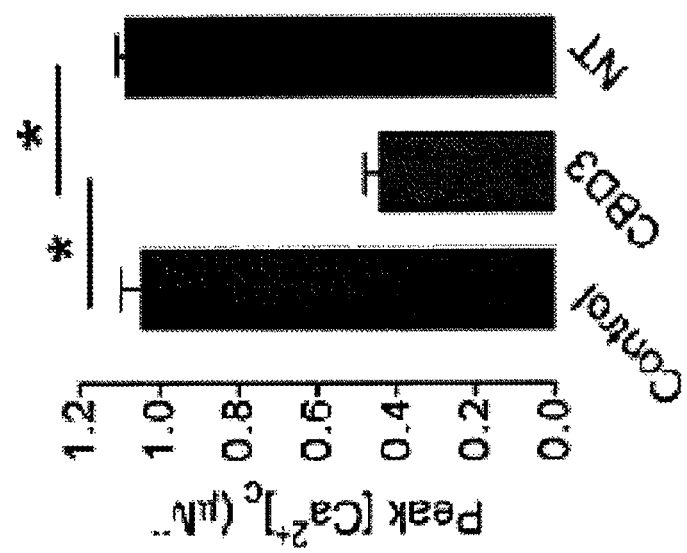
FIG. 2C. Bar graph of peak $Ca^{2+}$ concentrations measured for cells transfected with control, CBD3 or non-transfected (NT).

Overexpression of plasmids harboring CBD3, but not a scramble peptide control, in hippocampal neurons blocked depolarization-induced calcium signaling (FIGS. 2A-C). Thus, in vitro, CBD3 disrupts the CRMP-2-CaV2.2 interaction and affects CaV2.2 trafficking and current density.

Figure 2D:
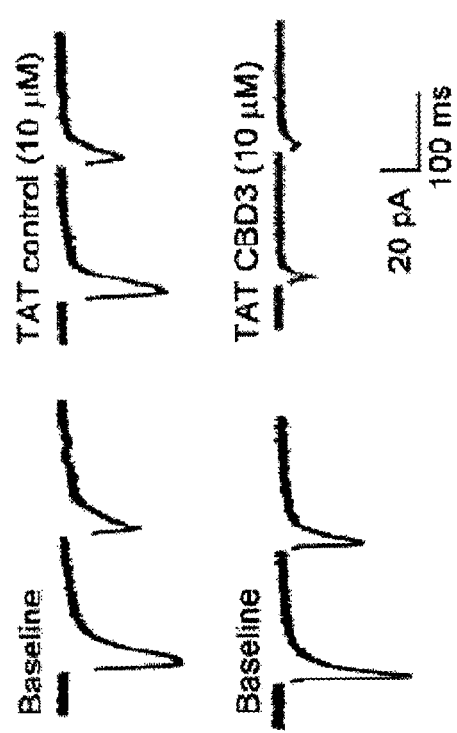
FIG. 2D. Traces of evoked EPSC's before and after application of either TAT or CBD3.
Figure 2E:
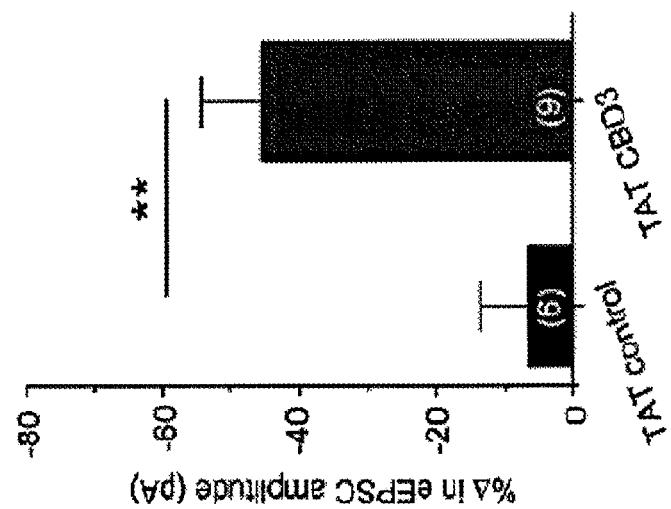
FIG. 2E. Bar graph of % change in eEPSC measured with either TAT control or TAT CBD3.
Figure 2F:
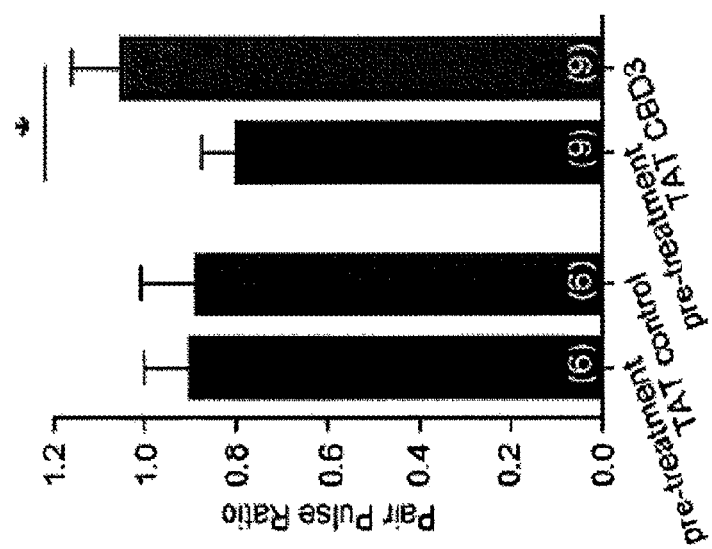
FIG. 2F. Bar graph change in paired-pulse ratio measured with either TAT control or TAT-CBD3.

Because CBD3 is not cell permeant, the protein transduction domain of the HIV-1 TAT protein was fused to CBD3, generating TAT CBD3 to try and create a more bioavailable peptide. To determine if uncoupling CRMP-2 from CaV2.2 with TAT CBD3 modulates synaptic transmission, a patch-clamp technique to record evoked excitatory postsynaptic currents (eEPSCs) in layer V pyramidal neurons (FIG. 2D), which express N-type calcium channels was used. Perfusion of cortical slices with TAT CBD3 reduced eEPSCs in layer V pyramidal neurons, suggesting a decrease in synaptic strength (FIGS. 2D and 2E). In contrast, a TAT control had no effect on the frequency or amplitude of eEPSCs. Furthermore, CBD3 increased pair pulse ratios (FIGS. 2D and 2F), suggesting a reduction in release probability of glutamate from axonal terminals.

Figure 8A:
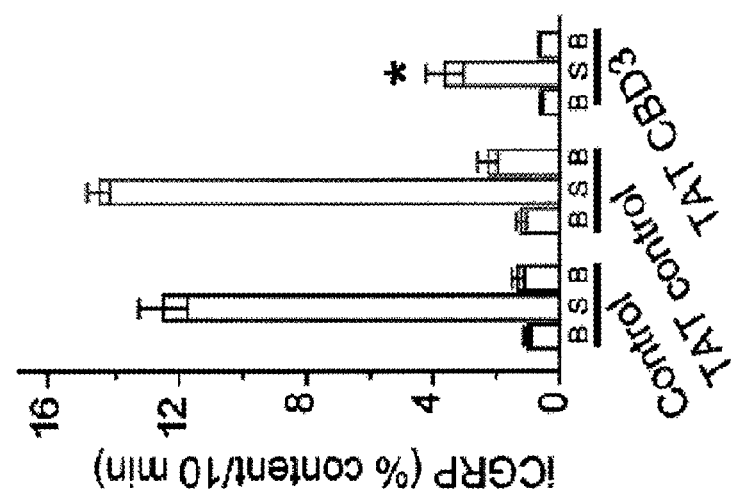
FIG. 8A. Bar graph of mean % of total iCGRP release measured in cell, tracked with, control, TAT control or TAT CBD3.
Figure 8B:
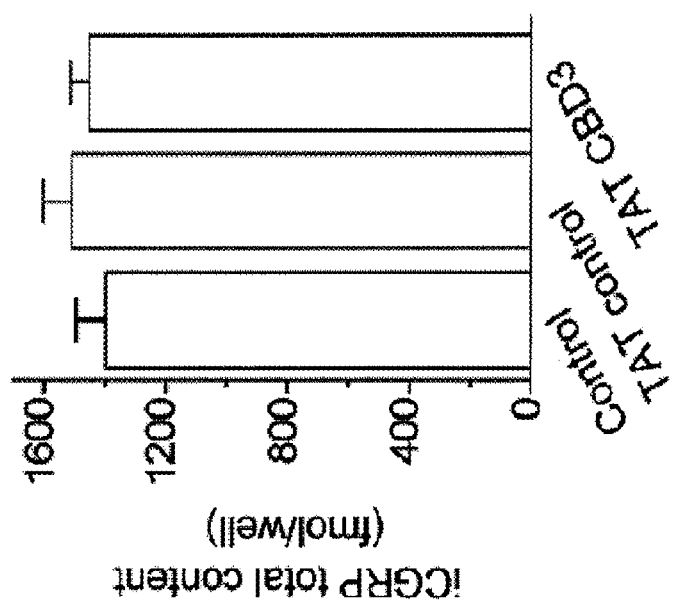
FIG. 8B. Bar graph of iCGRP content from DRGS treated with control, TAT control or TAT CBD3.
Figure 8C:
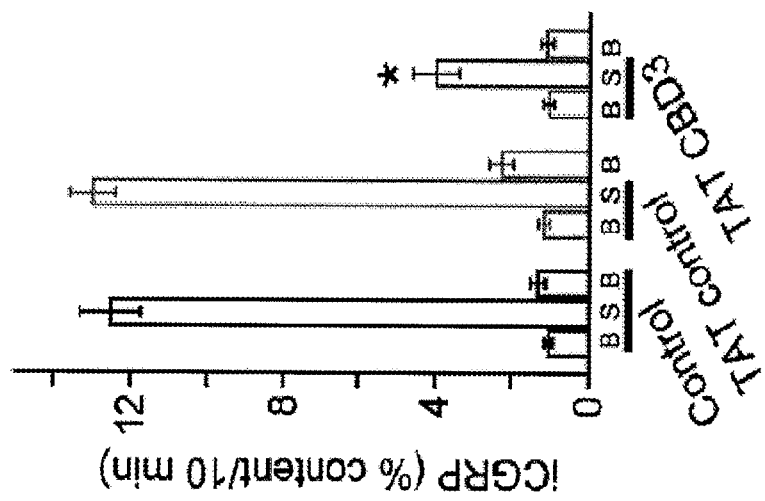
FIG. 8C. Bar graph of mean % of total iCGRP release measured in cell, tracked with, controL, TAT control or TAT CBD3.
Figure 8D:
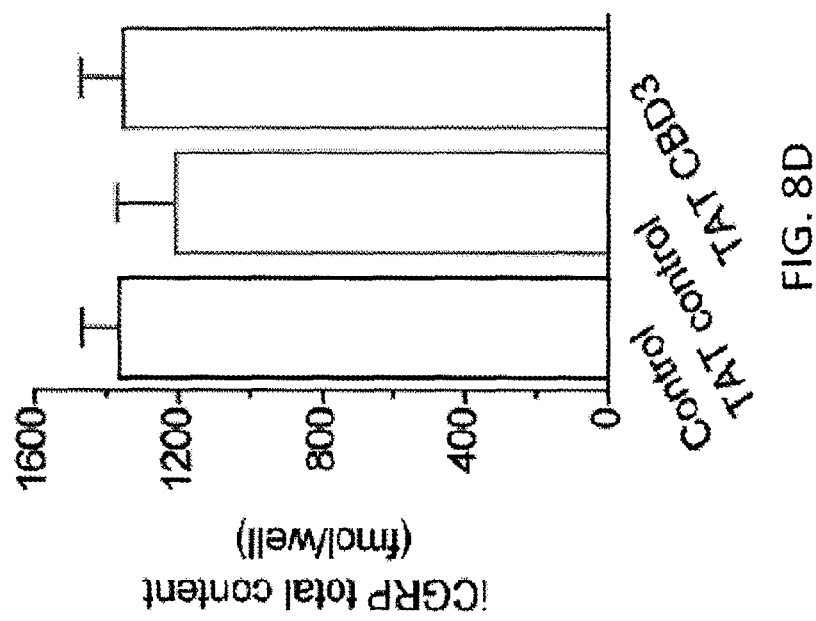
FIG. 8D. Bar graphs of total iCGRP content measured with control, TAT control or TAT CBD3.

CBD3 reduces evoked transmitter release from isolated sensory neurons and spinal cord slices. Referring now to FIG. 8. TAT CBD3 blocks $K^+$-stimulated transmitter release in DRG neurons. Adult mouse DRG neurons were maintained in culture for 5-7 days prior to the release experiments. (A) Bar graph of immunoreactive caloitonin gene-related peptide (iCGRP) release expressed as mean percent total iCGRP content of cells in each well±s.e.m. (n=12 wells/condition). Neunopeptide release was measured from cells treated with normal HEPES buffer containing 3.5 mM KCl (basal, B), HEPES buffer containing 50 mM KCl (S), and HEPES buffer containing 3.5 mM KCl again. DRGs were exposed to TAT control or TAT CBD3 peptides, at 1 µM, overnight (FIGS. 8A and 8B) or were included in the 10 minutes prior to and throughout the high $K^+$ exposures (FIGS. 8C and 8D). The resulting total TAT peptides exposure time was 12 h and 20 minutes (FIGS. 8A and 8B) or 30 min (FIGS. 8C and 8D). Asterisks (*) indicate statistically significant differences in iCGRP release between TAT CBD3 and the control (no treatment) or TAT control using an ANOVA with Dunnett's post-hoc test (p<0.05). In all eases, release stimulated by high extracellular $K^+$ as significantly higher than basal release. (FIGS. 8B and 8D) The total content of iCGRP measured at the end of the release experiment. There were no significant differences in iCGRP content between the conditions tested.

Figure 9:
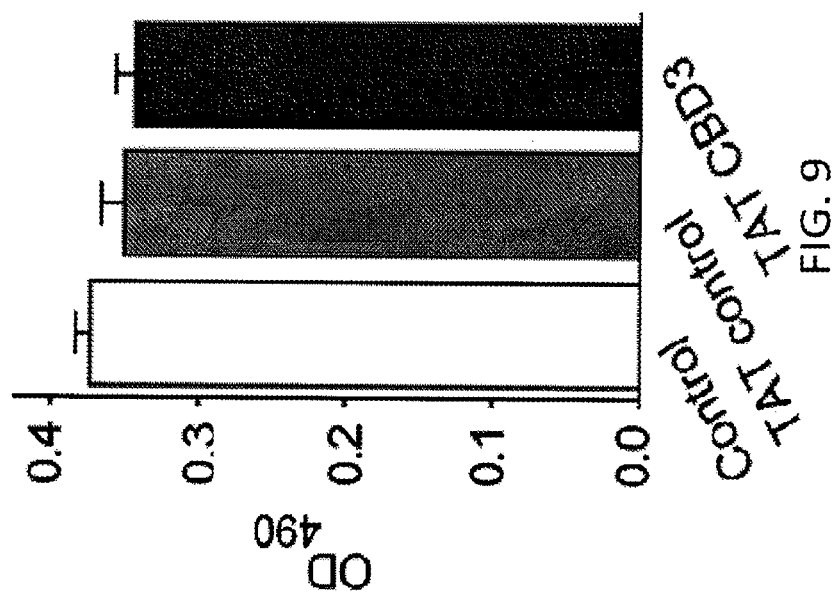
FIG. 9. Bar graph absorbance at 490 nm of DRGs treated with vehicle (control), TAT control or TAT CBD3.

Referring now to FIG. 9. TAT CBD3 does not affect cell viability. Cultured dorsal root ganglion neurons were treated with TAT control or TAT CBD3 (10 µM) for 12 h and then neuronal survival was assessed using the MIT colorimetric assay. Data represent means±S.E.M. percent absorbance at 490 nm relative to control (0.01% MPL; 1-methyl-2-pyrrolidinone; Sigma) was determined (n=8 wells per condition). Neither TAT peptide affected cell viability (p>0.05; Students' t-test).

As CaV2.2 is expressed on the presynaptic terminals of small diameter sensory neurons {Yamamoto, 2009 1 /id}, a study was carried out to determine if the actions of CBD3 were restricted to the CNS or if they could be extended to the PNS as well. It was shown recently that CRMP-2 expression levels impact release of the neuropeptide transmitter CGRP in sensory neurons. To determine if perturbing the CRMP-2-CaV2.2 interaction with the CBD3 peptide can modulate transmitter release, stimulated release of immunoreactive CGRP (iCGRP) was measured from sensory neurons treated with TAT CBD3 or TAT control. Pretreatment with TAT CBD3, but not TAT control, for 12 h or 20 min reduced stimulated CGRP release (FIG. 8). Total CGRP content was unaffected by the TAT peptides. Cell viability, measured after the 12 h treatment, was not affected by any of the treatments (FIG. 9).

To further examine the effect of CBD3 in the peripheral nervous system, capsaicin-evoked CGRP release was measured from spinal cord slices following incubation with TAT CBD3 or TAT control.

Figure 3C:
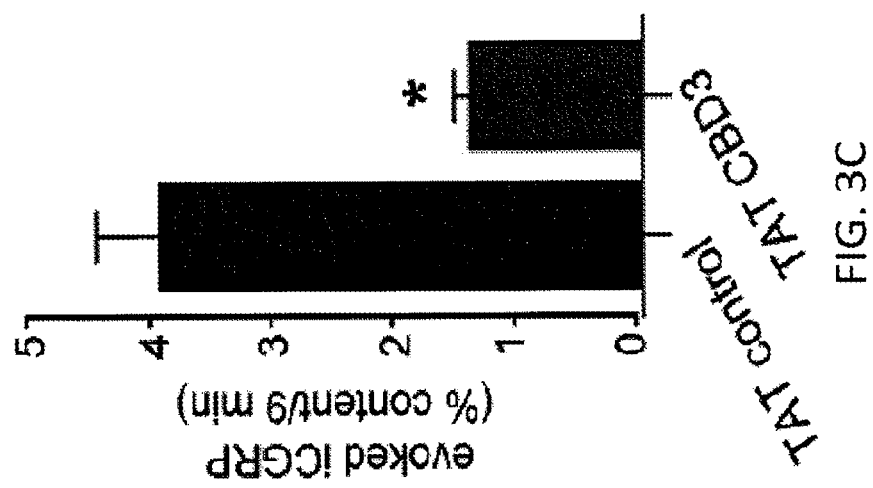
FIG. 3C. Bar graph of evoked iCGRP measured with either TAT control or TAT CBDE.
Figure 3D:
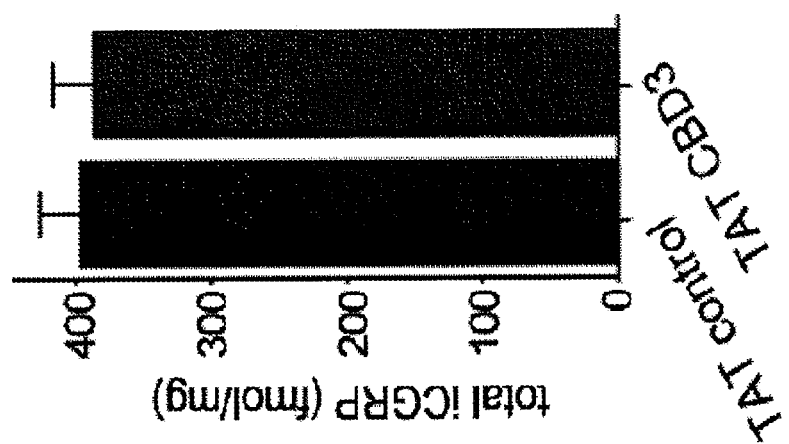
FIG. 3D. Bar graph of total iCGRP measured with either TAT control or TAT CBD3.

Referring now to FIG. 3. CBD3 peptide inhibits capsaicin-stimulated release of iCGRP from spinal cord slices. iCGRP release from spinal cord slices stimulated by three 3-min exposures to Hepes buffer alone (white bars) or Hepes buffer containing 500 nM capsaicin (blue bars (FIG. 3A) or red bars (FIG. 3B) is expressed as mean percent total peptide content of iCGRP in the spinal cord slice±SEM (n=7 animals per condition). TAT control (FIG. 3A) or TAT CBD3 (FIG. 3B), at 20 µM, was included in the six 3-min incubations indicated by lines, for a total exposure time of 18 min. (FIG. 3C) Evoked release, or release due to capsaicin stimulation alone, is compared between TAT treatments. The evoked release was obtained by subtracting iCGRP release during three basal fractions from that during the three capsaicin-stimulated fractions in each treatment group. *, p<0.05 versus basal iCGRP release between treatment groups and the no growth factor condition using an ANOVA with Dunnett's post-hoc test (p<0.05). In all cases, release stimulated by capsaicin was significantly higher than basal release. (FIG. 3D) Total content of iCGRP released during the perfusion and the amount remaining in the tissues measured at the end of the release experiments.

Figure 4A:
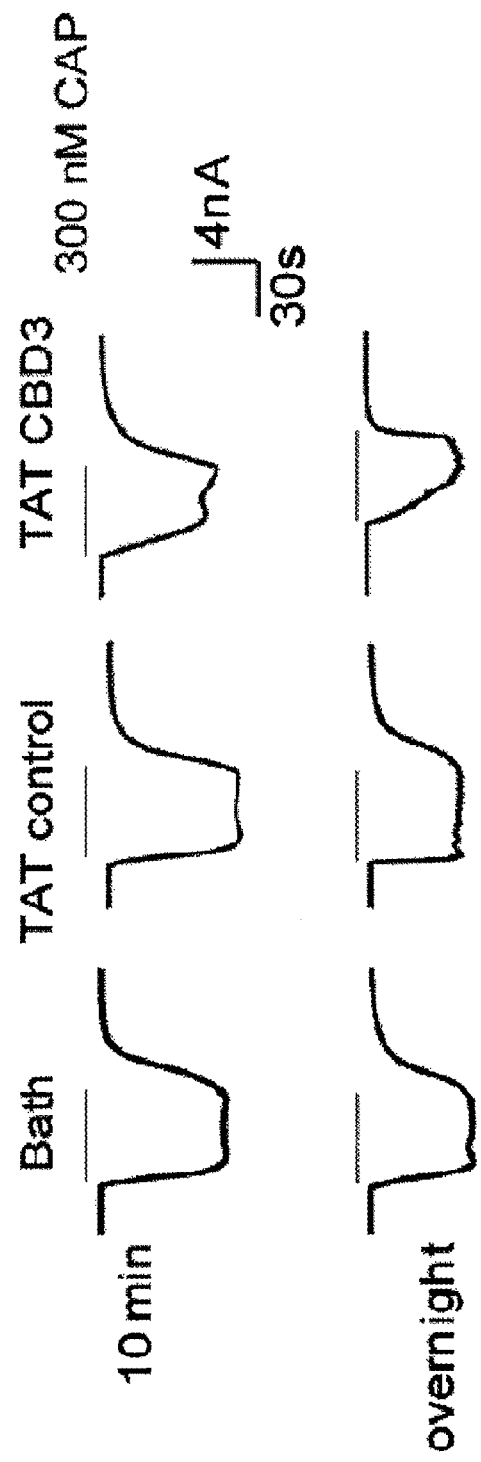
FIG. 4A. Current traces of capsaicin-sensitive currents through TRPV1 channels treated with TAT control or TAT CBD3.
Figure 4B:
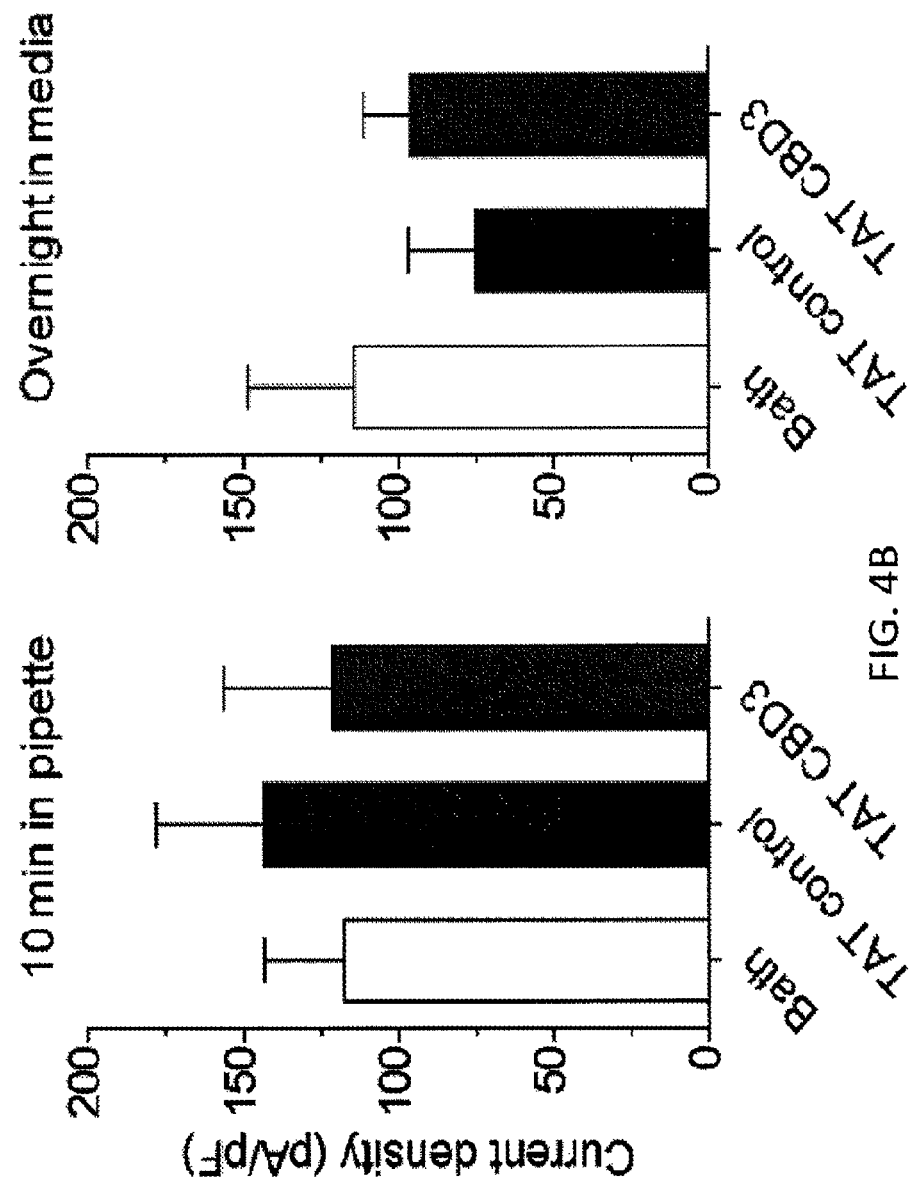
FIG. 4B. Bar graph of peak current density evoked by capsaicin after pre-treatment with TAT control or TAT CBD3.

Referring now to FIG. 4. TAT CBD3 does not activate capsaicin-evoked TRPV1 channels in DRGs. (FIG. 4A) Representative non-desensitizing current traces of TRPV1 in response to 300 nM capsaicin after vehicle control DMSO (bath), TAT control, or TAT CBD3 peptide treatment for 10 minutes (administered via the recording pipettes) or overnight (12-16 hours in culture medium). (FIG. 4B) Cumulative summary data of peak current density (pA/pF) in response to 300 nM capsaicin after 10 minutes (left) or overnight exposure (right) to vehicle control DMSO (white bars), TAT control (blue bars), or TAT CBD3 peptide (red bars).

Incubation with TAT control or TAT CBD3 did not change basal iCGRP release (FIGS. 3A and 3B). However, incubation with TAT CBD3 led to a significant decrease in evoked CGRP release compared to TAT control (FIG. 3C). The total content of iCGRP was not different between the two treatments (FIG. 3D).

Capsaicin-evoked iCGRP release is thought to be mediated through the transient receptor potential vanilloid type 1 (TRPV1) channel. Next investigated was whether the effect of CBD3 on CGRP release was due to inhibition of the TRPV1 channel. Currents were recorded from isolated dorsal root ganglion (DRG) neurons, neurons which had previously shown a functional coupling between CRMP-2 and CaV2.2.

Figure 5A:
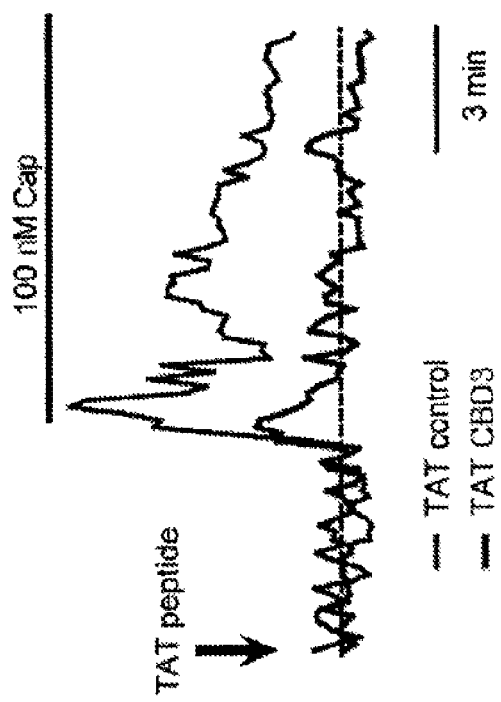
FIG. 5A. Blood flow changes measured after challenge with capsaicin after pre-treatment with TAT control or TAT CBD3.
Figure 5B:
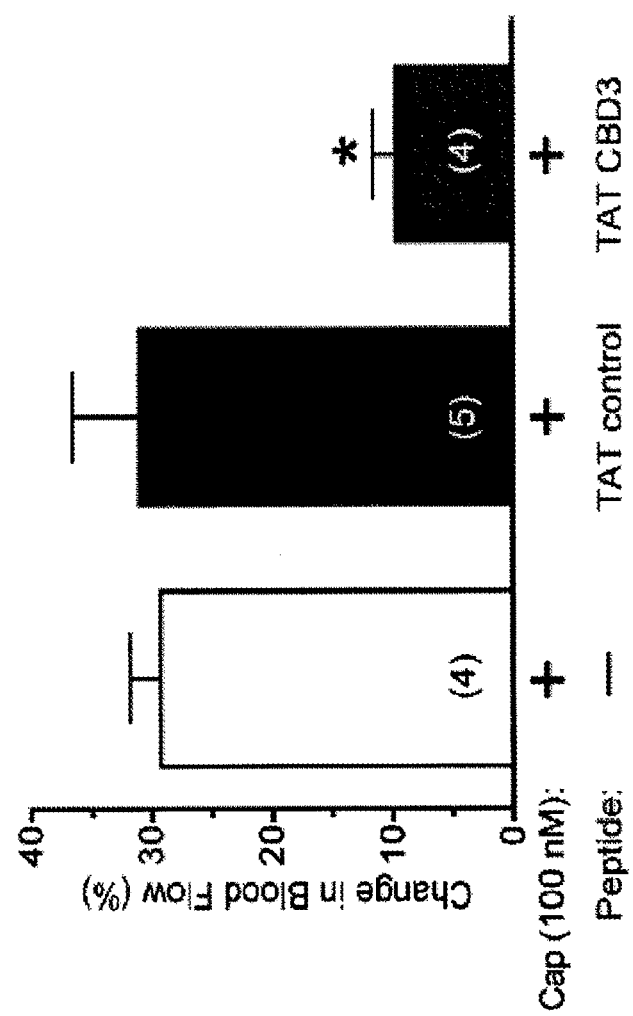
FIG. 5B. Bar graph of change in blood flow measured after challenge with capsaicin and pre-treatment with TAT control or TAT-CBD3.

Referring now to FIG. 5. TAT CBD3 reduces blood flow changes in response to capsaicin-induced activation of the trigeminovascular system. (FIG. 5A) Representative normalized traces of middle meningeal blood flow changes in response to nasally administered capsaicin (Cap, 100 nM) in the presence of TAT control (blue trace) or TAT CBD3 pretreatment (30 µM, applied durally 15 minute prior to Cap administration). Laser Doppler flowmetry measurements were collected at 1 Hz and binned by averaging every 10 samples for graphical representation. The data from each animal was normalized to the first 3 minutes of basal data and the horizontal dashed line indicates the calculated baseline. (FIG. 5B) Summary of blood flow changes following nasal administration of Cap in the absence or presence of previous administration of TAT CBD3 or TAT control to the dura. The capsaicin-induced blood flow changes were CGRP-dependent as they could be blocked by prior topical administration of the CGRP antagonist, $CGRP_{8-37}$ (5±4%, n=3, not shown). Values are mean±S.E.M. *p<0.05 compared to capsaicin-induced blood flow changes in the presence of TAT CBD3 (unpaired Student's t-test). The number of animals tested for each condition is indicated in parentheses.

Figure 10A:
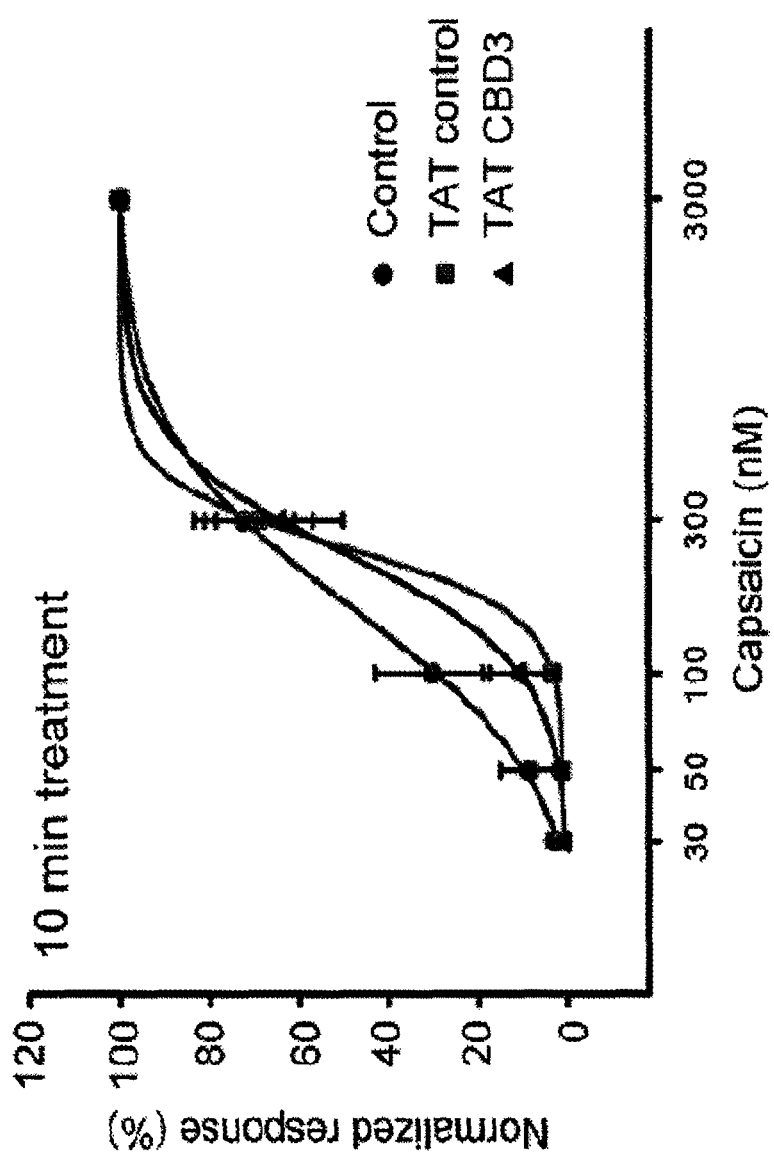
FIG. 10A. TRPV1 response in DRG neurons to different doses of capsaicin after 10 minutes of exposure to control, TAT control or TAT CBD3.
Figure 10B:
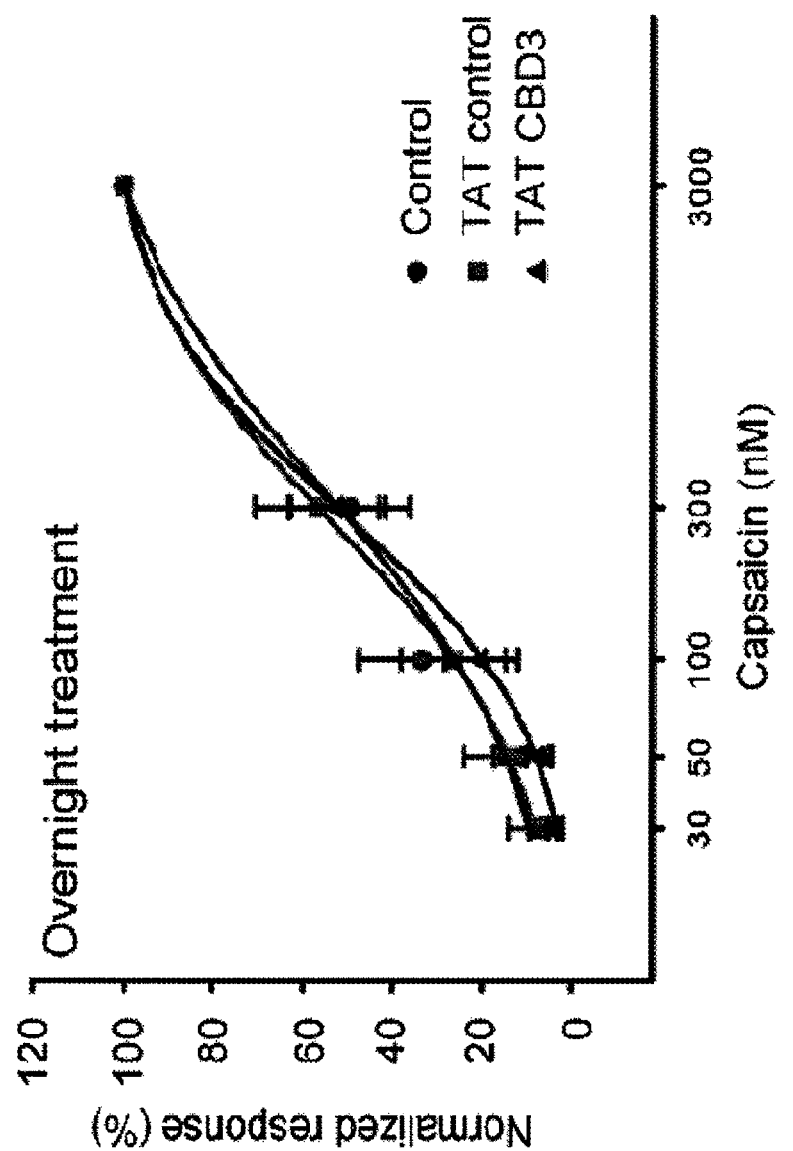
FIG. 10B. TRPV1 response in DRG cells to different doses of capsaicin after overnight exposure to control, TAT control or TAT CBD3.

Referring now to FIG. 10. TAT CBD3 does not activate capsaicin-evoked TRPV1 response in rat dorsal root ganglion (DRG) neurons. Cumulative summary data of peak current density (pA/pF), normalized to the maximum capsaicin-evoked current, in response to various concentrations of capsaicin after 10 minutes (FIG. 10A) or overnight exposure (FIG. 10B) to vehicle control DMSO (red circles), TAT control (green squares), or TAT CBD3 peptide (blue triangles). The numbers of cells recorded were: control (n=6), TAT control (n=7), and TAT CBD3 (n=6). Lines represent best fits of the data. There were no differences in normalized capsaicin response at any of the capsaicin concentrations tested for either peptide.

DRGs exposed to TAT CBD3, administered via the recording pipette or overnight in the cell culture medium, did not exhibit differences in capsaicin-evoked current density when the voltage was held at −60 mV (FIGS. 4 and 10). This is an important negative control, because the lack of an effect of CBD3 on TRPV1 current demonstrates that the inhibitory actions of CBD3 on neurotransmitter release and dural blood flow (see below) and transmitter release are not via inhibition of TRPV1 channels.

CBD3 inhibits capsaicin-evoked vasodilatation in the rat dura mater. The dura mater is innervated by trigeminal capsaicin-sensitive peptidergic nociceptive afferent nerves which mediate meningeal vascular responses. Capsaicin induced a rapid and robust increase in meningeal blood flow (FIG. 5A) which returned toward baseline values within minutes. Dural application of TAT CBD3 prior to capsaicin significantly inhibited the capsaicin-induced blood flow changes (FIG. 5B). The effects of TAT CBD3 administration alone did not differ from saline which was routinely administered as a control. TAT control did not alter basal blood flow or inhibit capsaicin-induced blood flow.

CBD3 suppresses formalin-induced nociception. Since CaV2.2 plays a well-known role in pain, whether the CBD3 peptide could attenuate nociceptive responses in several animal models of pain was examined. First the effects of the CBD3 and control peptides using the formalin test were determined. In animals administered a subcutaneous injection of control peptide 30 minutes prior to intraplantar injection of formalin, the expected biphasic formalin response was observed.

Referring now to FIG. 6. TAT CBD3 peptide reduces inflammatory and antiretroviral toxic neuropathic pain. (FIG. 6A) Time course of number of flinches induced by intraplantar injection of formalin (2.5% in 50 µl) in animals pretreated with TAT control (30 µM intraplantar) or TAT CBD3 (30 µM intraplantar) 30 min before formalin (n=8-9). (FIG. 6B) The effect of TAT control (blue) or TAT CBD3 (red) on the total number of flinches overall (left) or in formalin-induced phase 1 (0-10 min) and phase 2 (15-60 min; right). *, p<0.05 versus the respective phase TAT control. (FIG. 6C) Pretreatment with TAT CBD3 peptide attenuates capsaicin-evoked nocifensive behavior. Vehicle (0.3% DMSO), TAT control (30 µM), or TAT CBD3 (30 µM) in saline (40 µL) was applied in the right eye and nocifensive behavior was noted (white bars). Five minutes after treatment, Cap (3 µM) in saline (40 µL) was applied in the right eye and nocifensive behavior was noted by observers blinded to treatment condition (filled bars). Data are shown as mean±SEM (n=4-6 per group; p<0.01 and *p<0.001, two-way ANOVA). (FIG. 6D) Dose-dependent effect of TAT CBD3 peptide on ddC-induced decreases in paw withdrawal threshold (PWT) in the rat at 1 h and 4 h post injection. Animals subjected to a single ddC injection exhibited a decrease in PWT that was abolished by i.p. administration of TAT CBD3 peptide on post-injection day 7 (PID7) in a dose dependent manner. Data represent means±S.E.M.; *, p<0.01 versus ddC or TAT control (ANOVA with Dunnett's post-hoc test), n=6 per condition.

Immediately after injection, the animals displayed a high degree of flinching (phase 1) which lasted about 10 minutes followed by a second period of flinching (phase 2) which subsided by 60 minutes. Animals injected with CBD3 peptide displayed blunted nociceptive behaviors in both phases (FIGS. 6A and 6B), suggesting that the peptide inhibits nociception mediated by direct activation of the sensory neurons (phase 1) and nociception associated with inflammation and possible spinal involvement (phase 2).

CBD3 attenuates capsaicin-evoked nocifensive behavior. Referring now to FIG. 3 and FIG. 4, it was demonstrated that CBD3 attenuates capsaicin-induced increases in dural blood flow and release of iCGRP from the dorsal spinal cord, respectively. To determine whether CBD3 has similar inhibitory effects on capsaicin-induced nociception in vivo, corneal wipe test was utilized. The cornea is a specialized tissue innervated by trigeminal afferent nerves, of which approximately 25% express TRPV1. Application of noxious substances to the eye induces a transient nocifensive response in awake animals which can be reversed by either peripherally or systemically administered antinociceptives, thus it is a good model for determining the antinociceptive effect of peripherally administered CBD3 peptide on acute trigeminally-mediated nociception. Application of the CBD3 peptide alone did not induce nocifensive behavior. A 30 min pretreatment with the TAT CBD3 peptide, but not control peptide, significantly attenuated the nocifensive behavior induced by capsaicin instillation (FIG. 6C), suggesting that the CBD3 peptide is antinociceptive at a peripheral site of action.

Figure 6A:
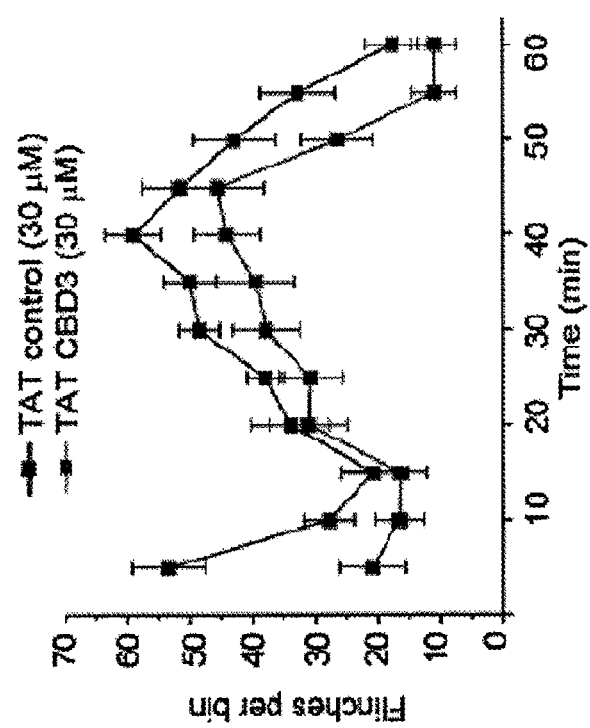
FIG. 6A. Number of flinches measured in animals over time pre-treated with either TAT control or TAT CBD3.
Figure 6B:
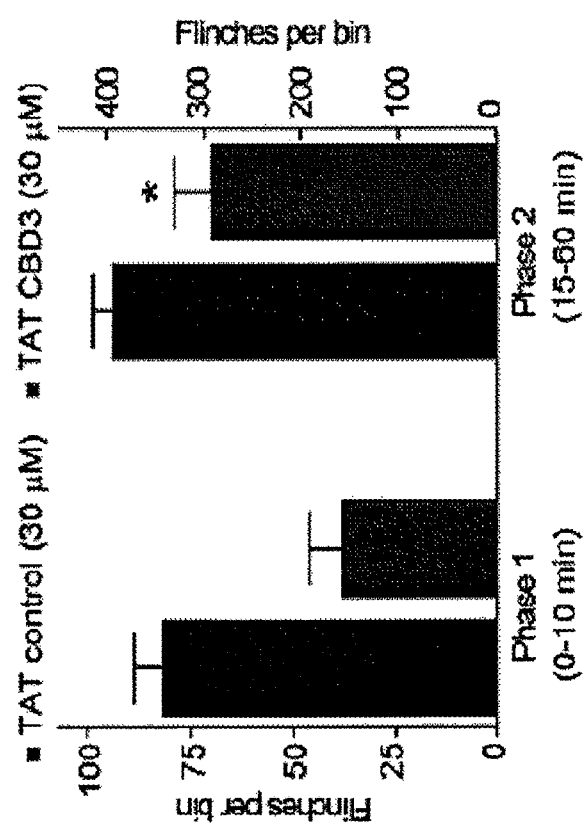
FIG. 6B. Bar graph of total number of Flinches: the animals were pre-treated with either TAT control or TAT CBD3.
Figure 6C:
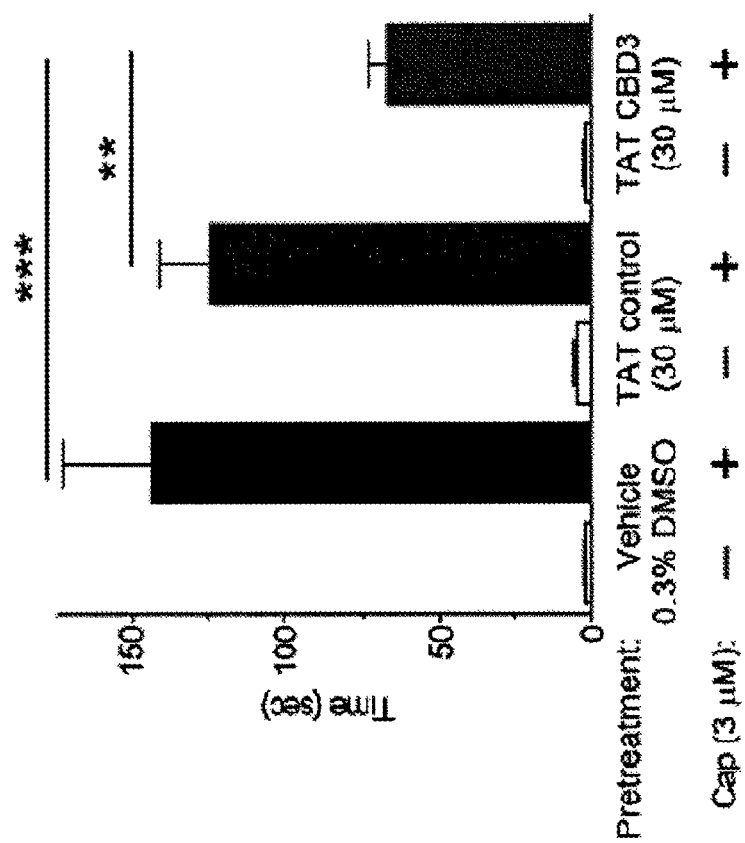
FIG. 6C. Bar graph of capsaicin-evoked nocifensive behaviours measured with: vehicle, TAT control, or TAT CBD3.
Figure 6D:
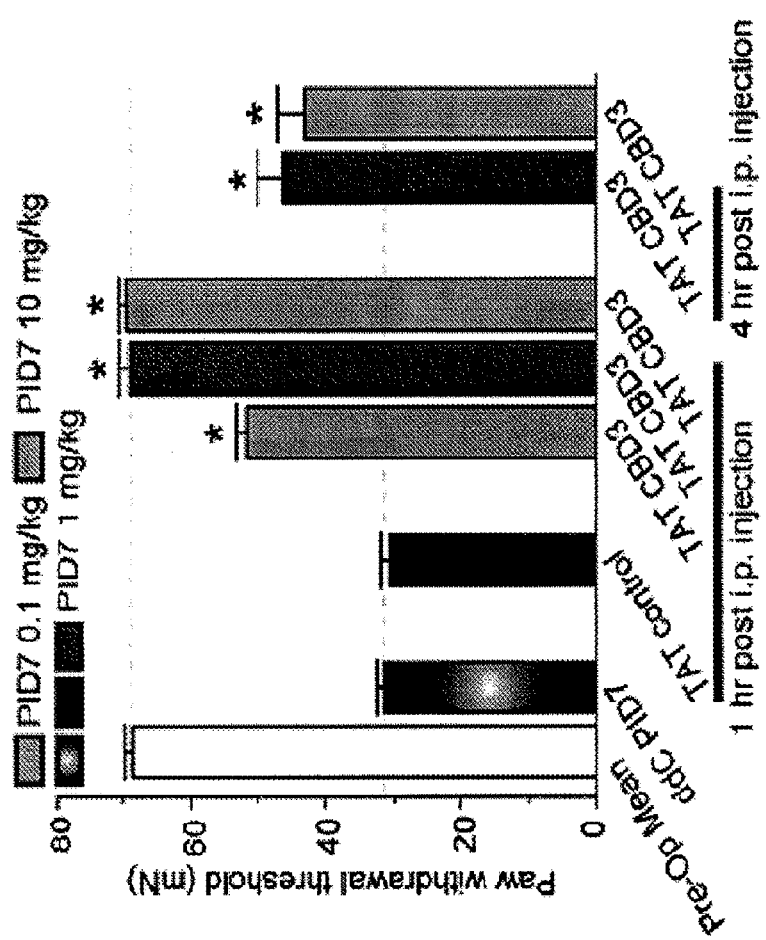
FIG. 6D. Bar graph of paw withdraw threshold tested in the ddC model of chronic neuropathic pain measured post-treatment with either TAT control or TAT-CBD3 either 1 or 4 hours post-treatment.
Figure 7A:
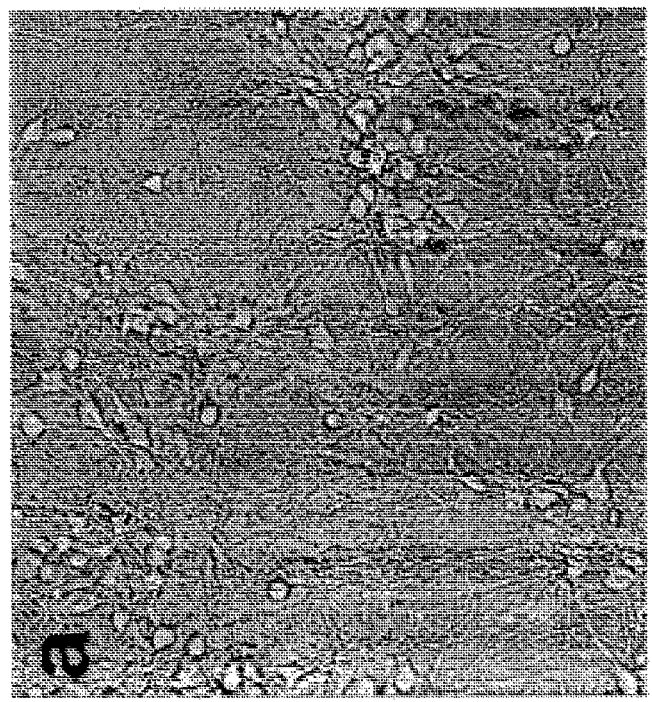
FIG. 7A. Photomicrograph, bright field image of neuron expressing control plasmid.
Figure 7B:
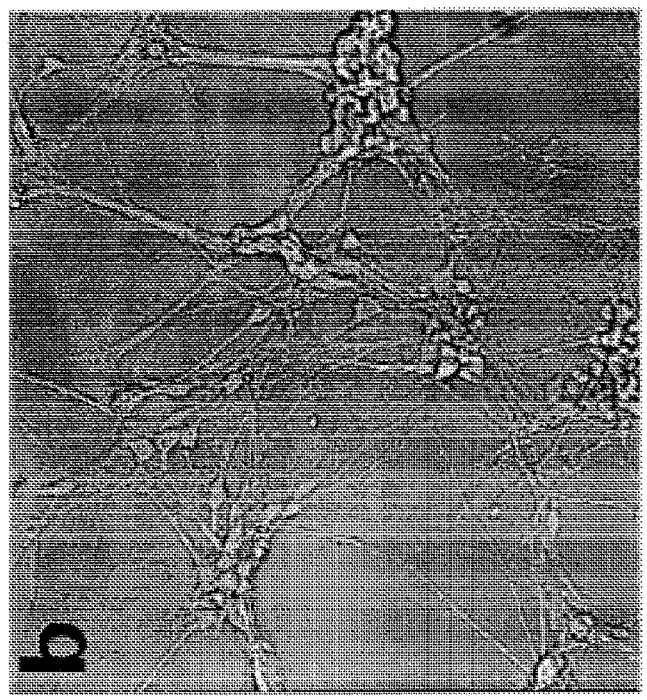
FIG. 7B. Photomicrograph, bright field image of neuron expressing CBD3 plasmid.
Figure 7C:
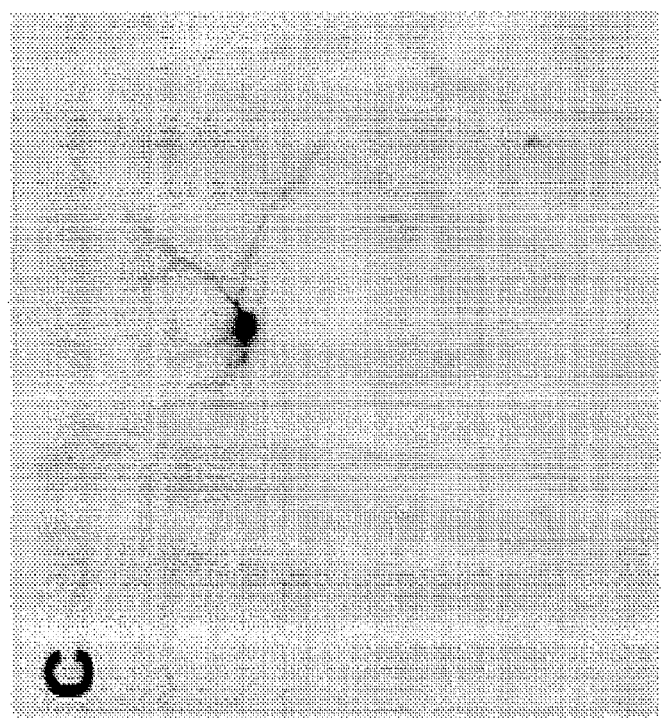
FIG. 7C. Photomicrograph, black and white version of green fluorescent (EGFP) protein of neuron expressing control.
Figure 7D:
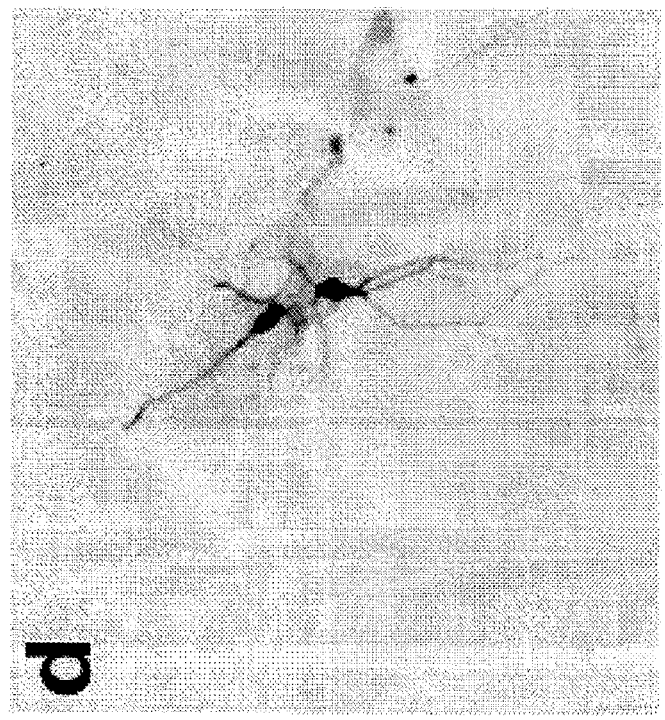
FIG. 7D. Photomicrograph: black and white version of EGFP of neuron expressing CBD3.
Figure 7E:
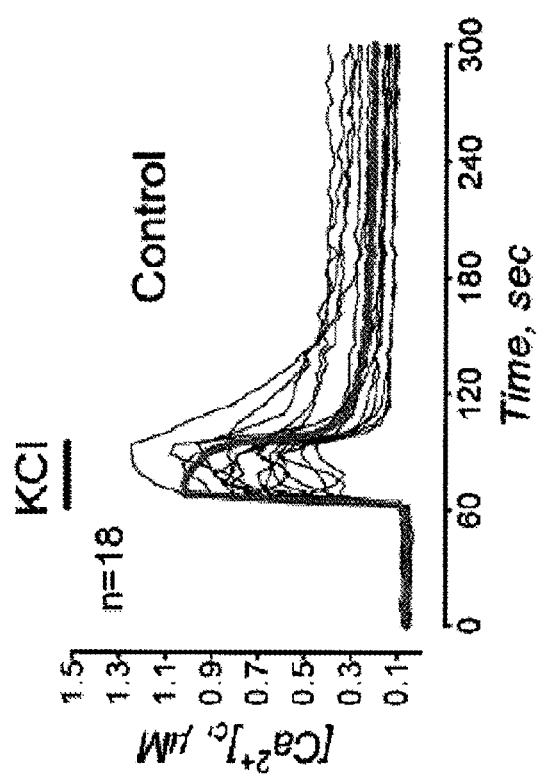
FIG. 7E. Depolarization traces of individual neurons expressing CBD3.
Figure 7F:
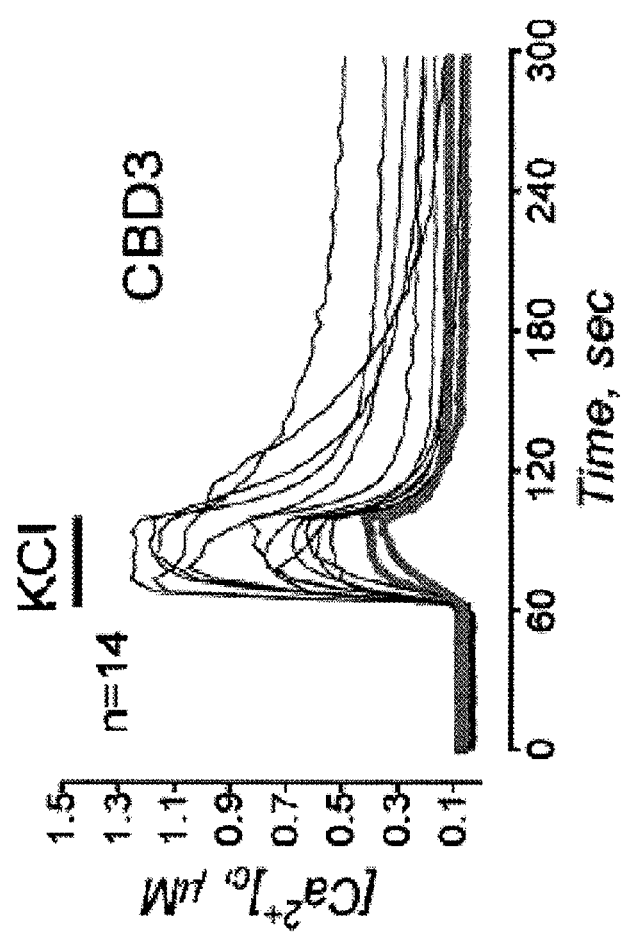
FIG. 7F. Depolarization traces of individual neurons expressing control.

6CBD3 reverses ddC-induced neuropathic pain behavior. Nucleoside reverse transcriptase inhibitors (NRTIs), commonly used for AIDS treatment, are known to produce serious adverse side effects including painful neuropathies. As the nucleoside analog reverse transcriptase inhibitor, 2',3'-dideoxycytidine (ddC) and other anti-retroviral nucleoside analogs are thought to alter regulation of intracellular calcium, whether TAT CBD3 peptide could reverse AIDS therapy-induced painful peripheral neuropathy was evaluated. The ability of TAT CBD3 peptide and TAT control peptide to reverse tactile hyperalgesia was evaluated seven days after injection of ddC. It was found that TAT CBD3 peptide, but not TAT control peptide, caused a dose-dependent increase in paw withdrawal threshold when administered i.p. (FIG. 6D). Maximal reversal of tactile hyperalgesia (100%) was observed at the 1 mg/kg dose 1 h after intraperitoneal injection. Four hours after injection, TAT CBD3 was less than 50% effective in the reversal of hyperalgesia. To explore the sites of distribution of the peptides after i.p. injection, tissue samples from animals injected with TAT peptide control were collected. Within 15 min after the injection the peptide was detected in the DRG and spinal cord while 1 h following the injection, the peptide was also observed in the brain (FIG. 11).

Figure 11:
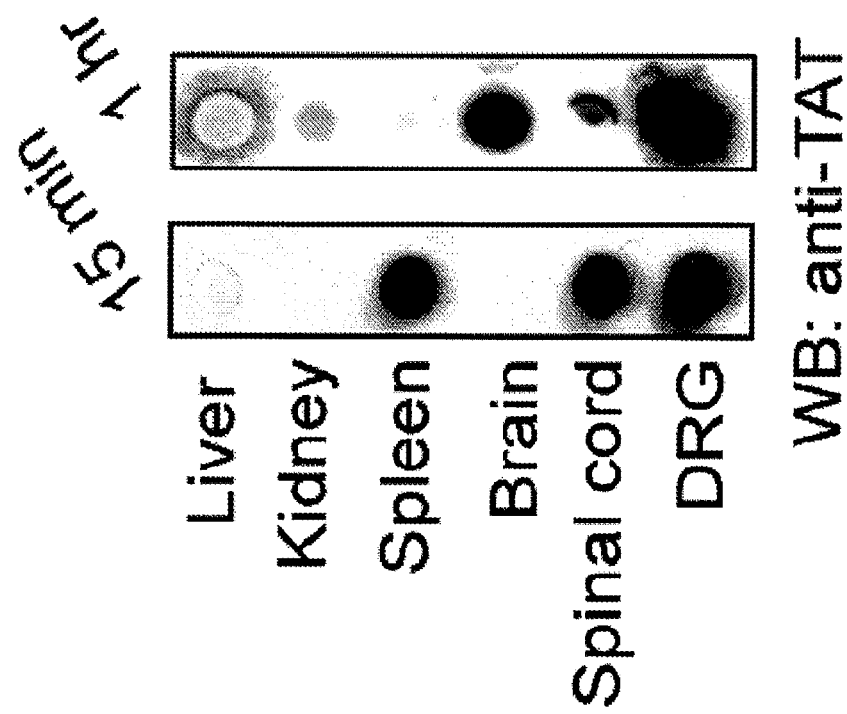
FIG. 11. Immunoblots of rat tissue showing distribution of TAT.

Referring now to FIG. 11. Distribution of TAT peptide in rat tissues following intraparitoneal administration. Dot blot analysis of indicated tissues from rats injected i.p. with 25 mg/kg of TAT control peptide. Rats were euthanized at 15 or 60 min post injection and tissues were frozen in liquid N2. Lysates, 60 µg, of each tissue were bound to a membrane and immunoblotted with an antibody against the TAT protein, which contains the transduction domain present in the TAT control peptide. At 15 min, TAT peptide was detected in spleen and largely concentrated in lumbar dorsal root ganglion (DRG) and lumbar section of the spinal cord. At 1 h, the TAT peptide was also detected in kidney, brain, spinal cord and was abundant in the DRG.

These results indicate that using CBD3 to interfere with CaV2.2 and CRMP-2 interactions can suppress inflammatory and neuropathic pain behaviors.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

I claim:

1. A compound that uncouples collapsin response mediator protein 2 ("CRMP-2") and N-type voltage-gated calcium channels ("CaV2.2"), comprising:
   a compound of the formula X-Z,
   wherein X is a polypeptide having at least 80 percent identity to at least one polypeptide selected from the group consisting of: SEQ ID NO.: 12 and SEQ ID NO.: 13;
   Z is at least one polypeptide having at least 80 percent identity to at least one polypeptide selected from the group consisting of: SEQ ID NO.: 1, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, and SEQ ID NO.: 10, wherein X and Z are fused to one another;
   wherein X retains the function of transducing Z into cells, and wherein Z binds to the CaV2.2 via its first intracellular loop ("L1") and/or the end of the C-terminus ("Ct-dis") regions.

2. The compound according to claim 1, wherein the X and Z are fused to one another via a peptide bond.

3. The compound according to claim 1, wherein X is polypeptide that has at least 90 percent identity to at least one polypeptide selected from the group consisting of SEQ. ID NO.: 11 and SEQ. ID NO.: 12.

4. The compound according to claim 1, wherein Z is a polypeptide that has at least 90 percent identity to at least one polypeptide selected from the group consisting of SEQ. ID NO.: 1, SEQ. ID NO.: 3, SEQ. ID NO.: 4, SEQ. ID NO.: 5, SEQ. ID NO.: 6, SEQ. ID NO.: 7, SEQ. ID NO).: 8, SEQ. ID NO.: 9, and SEQ. ID NO.: 10.

5. The compound according to claim 1, wherein X is at least one polypeptide that has at least 95 percent identity to at least one polypeptide selected from the group consisting of SEQ. ID NO.: 11 and SEQ. ID NO.: 12.

6. The compound according to claim 1, wherein
   X is a polypeptide having at least 90 percent homology to at least one polypeptide selected from the group consisting of: SEQ. ID NO.: 12 and SEQ. ID NO.: 13 and
   Z is a polypeptide having at least 90 percent homology to at least one polypeptide selected from the group consisting: of SEQ. ID NO.: 1, SEQ. ID NO.: 3, SEQ. ID NO.4: SEQ. ID NO.: 5, SEQ. ID NO.: 6, SEQ. ID NO.: 7, SEQ. ID NO.: 8, SEQ. ID NO.: 9, and SEQ. ID NO.: 10, wherein X and Z are fused to one another.

7. The compound according to claim 1, wherein
   X is a polypeptide having at least 95 percent homology to at least one polypeptide selected from the group consisting of: SEQ. ID NO.: 12 and SEQ. ID NO.: 13 and
   Z is a polypeptide having at least 95 percent homology to at least one polypeptide selected from the group consisting: of SEQ. ID NO.: 1, SEQ. ID NO.: 3, SEQ. ID NO.4, SEQ. ID NO.: 5, SEQ. ID NO.: 6, SEQ. ID NO.: 7, SEQ. ID NO.: 8, SEQ. ID NO.: 9, and SEQ. ID NO.: 10, wherein X and Z are fused to one another.

8. The compound according to claim 1, wherein X is at least one polypeptide selected from the group consisting of SEQ. ID NO.: 12 and SEQ. ID NO.: 13.

9. The compound according to claim 1, wherein Z is a polypeptide selected from the group consisting: of SEQ. ID NO.: 1, SEQ. ID NO.: 3, SEQ. ID NO.4, SEQ. ID NO.: 5, SEQ. ID NC).: 6, SEQ. ID NO.: 7, SEQ. ID NO.: 8, SEQ. :ID NO.: 9, and SEQ. ID NO.: 10.

10. The compound according to claim 1, wherein the compound is SEQ. ID NO. 11.

11. A method of treating a patient suffering from AIDS therapy-induced neuropathy, comprising the steps of:
    providing at least one compound according to claim 1 or a pharmaceutically acceptable salt thereof; and
    administering at least one therapeutically effective dose of said compound to the patient.

12. The method of according to claim 11, wherein the dose is between about 1 mg to about 100 mg of said compound per about 1 kilogram of the patient's body weight.

13. The method of according to claim 11, wherein the dose is between about 1 mg to about 20 mg of said compound per about 1 kilogram of the patient's body weight.

14. The method of according to claim 11, wherein the patient is a mammal.

15. The method of according to claim 11, wherein the patient is a human being.

16. A kit for treating a patient, comprising;
    at least one therapeutically effective dose of the compound according to claim 1 or a pharmaceutically acceptable salt thereof.

17. The kit according to claim 16, wherein said compound in the kit is formulated for injection.

18. The kit according to claim 16, wherein said compound in the kit is formulated with at least one additional material that helps to preserve the activity of said compound.

* * * * *